(12) United States Patent
Jang

(10) Patent No.: US 7,766,956 B2
(45) Date of Patent: Aug. 3, 2010

(54) INTRAVASCULAR STENT AND ASSEMBLY

(75) Inventor: G. David Jang, Redlands, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1208 days.

(21) Appl. No.: 10/723,644

(22) Filed: Nov. 26, 2003

(65) Prior Publication Data

US 2004/0133271 A1    Jul. 8, 2004

Related U.S. Application Data

(63) Continuation-in-part of application No. 09/960,861, filed on Sep. 21, 2001, now abandoned, and a continuation-in-part of application No. 09/942,077, filed on Aug. 28, 2001, now abandoned, application No. 10/723,644, which is a continuation-in-part of application No. 09/960,861, filed on Sep. 21, 2001, now abandoned, application No. 10/723,644, which is a continuation-in-part of application No. 09/963,125, filed on Sep. 24, 2001, now abandoned, application No. 10/723,644, which is a continuation-in-part of application No. 09/960,868, filed on Sep. 21, 2001, now abandoned, application No. 10/723,644, which is a continuation-in-part of application No. 09/962,792, filed on Sep. 24, 2001, now abandoned.

(60) Provisional application No. 60/235,164, filed on Sep. 23, 2000, provisional application No. 60/234,614, filed on Sep. 22, 2000, provisional application No. 60/235,167, filed on Sep. 23, 2000, provisional application No. 60/235,115, filed on Sep. 25, 2000, provisional application No. 60/235,180, filed on Sep. 25, 2000.

(51) Int. Cl.
*A61F 2/06* (2006.01)
*A61M 29/00* (2006.01)

(52) U.S. Cl. ..................... 623/1.15; 606/195
(58) Field of Classification Search ............... 623/1.15; 606/191, 194, 195
See application file for complete search history.

(56) References Cited

U.S. PATENT DOCUMENTS

| | | | |
|---|---|---|---|
| 2,836,181 A | 5/1958 | Tapp | 128/334 |
| 3,105,492 A | 10/1963 | Jeckel | 128/334 |
| 3,272,204 A | 9/1966 | Artandi et al. | 128/334 |
| 3,490,975 A | 1/1970 | Lightwood et al. | 156/167 |

(Continued)

FOREIGN PATENT DOCUMENTS

EP      0 709 067 A2    1/1996

(Continued)

OTHER PUBLICATIONS

U.S. Appl. No. 09/999,279, filed Nov. 30, 2001, Jansen et al.

(Continued)

*Primary Examiner*—Vy Q Bui
(74) *Attorney, Agent, or Firm*—Vidas, Arrett & Steinkraus

(57) ABSTRACT

Various intravascular stents, such as intracoronary stents, include improved expansion and connecting strut designs. Such stents can be both very flexible and fully cover vessel surface inside the vascular lumen, and be well designed for both the delivery phase and the deployed phase of the stent life cycle.

20 Claims, 39 Drawing Sheets

U.S. PATENT DOCUMENTS

| | | | |
|---|---|---|---|
| 3,509,883 A | 5/1970 | Dibelius et al. ............. 128/348 |
| 3,526,228 A | 9/1970 | Lyng ........................ 128/334 |
| 3,562,820 A | 2/1971 | Braun et al. ..................... 3/1 |
| 3,635,215 A | 1/1972 | Shea et al. ................. 128/130 |
| 3,771,526 A | 11/1973 | Rudle ........................ 128/334 |
| 3,868,956 A | 3/1975 | Alfidi et al. ................ 128/345 |
| 3,993,078 A | 11/1976 | Bergentz et al. ............ 128/334 |
| 4,078,167 A | 3/1978 | Banas et al. ................ 219/121 |
| 4,127,761 A | 11/1978 | Pauley et al. ............ 219/121 L |
| 4,130,904 A | 12/1978 | Whalen ........................ 3/1.4 |
| 4,140,126 A | 2/1979 | Choudhury ................ 128/325 |
| 4,141,364 A | 2/1979 | Schultze .................... 128/349 |
| 4,164,045 A | 8/1979 | Bokros et al. ................... 3/1.4 |
| 4,214,587 A | 7/1980 | Sakura, Jr. ............. 128/334 R |
| 4,300,244 A | 11/1981 | Bokros ........................ 3/1.4 |
| 4,313,231 A | 2/1982 | Koyamada ................... 3/1.4 |
| 4,319,363 A | 3/1982 | Ketharanathan ................ 3/1.4 |
| 4,425,908 A | 1/1984 | Simon ........................ 128/1 R |
| 4,441,215 A | 4/1984 | Kaster ........................... 3/1.4 |
| 4,470,407 A | 9/1984 | Hussein ........................ 128/6 |
| 4,501,264 A | 2/1985 | Rockey ........................ 128/1 R |
| 4,503,569 A | 3/1985 | Dotter ........................... 3/1.4 |
| 4,512,338 A | 4/1985 | Balko et al. ................. 128/1 R |
| 4,535,770 A | 8/1985 | Lemole ........................ 128/327 |
| 4,550,447 A | 11/1985 | Seiler, Jr. et al. ............... 623/1 |
| 4,553,545 A | 11/1985 | Maass et al. ................ 128/341 |
| 4,560,374 A | 12/1985 | Hammerslag ................ 604/49 |
| 4,580,568 A | 4/1986 | Gianturco ................... 128/345 |
| 4,597,389 A | 7/1986 | Ibrahim et al. ............. 128/328 |
| 4,647,416 A | 3/1987 | Seiler, Jr. et al. ............ 264/118 |
| 4,649,922 A | 3/1987 | Wiktor ........................ 128/344 |
| 4,655,771 A | 4/1987 | Wallsten ........................ 623/1 |
| 4,655,776 A | 4/1987 | Lesinski ........................ 623/10 |
| 4,665,918 A | 5/1987 | Garza et al. ................. 128/348 |
| 4,681,110 A | 7/1987 | Wiktor ........................ 128/348 |
| 4,693,721 A | 9/1987 | Ducheyne ................... 623/16 |
| 4,733,665 A | 3/1988 | Palmaz ........................ 128/343 |
| 4,739,762 A | 4/1988 | Palmaz ........................ 128/343 |
| 4,740,207 A | 4/1988 | Kreamer ........................ 623/1 |
| 4,760,849 A | 8/1988 | Kropf ........................ 128/341 |
| 4,762,128 A | 8/1988 | Rosenbluth ................ 128/343 |
| 4,768,507 A | 9/1988 | Fischell .................. 128/303 R |
| 4,769,029 A | 9/1988 | Patel ........................... 623/1 |
| 4,771,773 A | 9/1988 | Kropf .................... 128/303 R |
| 4,776,337 A | 10/1988 | Palmaz ........................ 128/343 |
| 4,787,899 A | 11/1988 | Lazarus ........................ 623/1 |
| 4,795,458 A | 1/1989 | Regan ........................... 623/1 |
| 4,795,465 A | 1/1989 | Marten ........................ 623/9 |
| 4,800,882 A | 1/1989 | Gianturco ................... 128/343 |
| 4,820,298 A | 4/1989 | Leveen et al. ................... 623/1 |
| 4,830,003 A | 5/1989 | Wolff et al. ................. 128/343 |
| 4,842,575 A | 6/1989 | Hoffman, Jr. et al. ......... 600/36 |
| 4,848,343 A | 7/1989 | Wallsten et al. ............. 128/343 |
| 4,851,009 A | 7/1989 | Pinchuk ........................ 623/66 |
| 4,856,516 A | 8/1989 | Hillstead ..................... 128/343 |
| 4,872,874 A | 10/1989 | Taheri ........................... 623/1 |
| 4,877,030 A | 10/1989 | Beck et al. ................. 128/343 |
| 4,878,906 A | 11/1989 | Lindemann et al. ............ 623/1 |
| 4,886,062 A | 12/1989 | Wiktor ........................ 128/343 |
| 4,913,141 A | 4/1990 | Hillstead ..................... 606/108 |
| 4,922,905 A | 5/1990 | Strecker ..................... 606/195 |
| 4,950,227 A | 8/1990 | Savin et al. ..................... 604/8 |
| 4,950,258 A | 8/1990 | Kawai et al. ................ 604/281 |
| 4,994,071 A | 2/1991 | MacGregor ................. 606/194 |
| 5,015,253 A | 5/1991 | MacGregor ................... 621/1 |
| 5,019,090 A | 5/1991 | Pinchuk ..................... 606/194 |
| 5,035,706 A | 7/1991 | Gianturco et al. ........... 606/198 |
| 5,037,392 A | 8/1991 | Hillstead ..................... 604/96 |
| 5,059,211 A | 10/1991 | Stack et al. ................. 606/198 |
| 5,064,435 A | 11/1991 | Porter ........................ 623/12 |
| 5,092,877 A | 3/1992 | Pinchuk ........................ 623/1 |
| 5,102,417 A | 4/1992 | Palmaz ........................ 606/195 |
| 5,104,399 A | 4/1992 | Lazarus ........................ 623/1 |
| 5,104,404 A | 4/1992 | Wolff ........................... 623/1 |
| 5,108,417 A | 4/1992 | Sawyer ........................ 606/198 |
| 5,122,154 A | 6/1992 | Rhodes ........................ 606/198 |
| 5,133,732 A | 7/1992 | Wiktor ........................ 606/195 |
| 5,135,536 A | 8/1992 | Hillstead ..................... 606/195 |
| 5,139,480 A | 8/1992 | Hickle et al. ................... 604/8 |
| 5,147,385 A | 9/1992 | Beck et al. ................... 623/1 |
| 5,147,400 A | 9/1992 | Kaplan et al. ................ 623/13 |
| 5,158,548 A | 10/1992 | Lau et al. ....................... 604/96 |
| 5,163,952 A | 11/1992 | Froix ........................... 623/1 |
| 5,195,984 A | 3/1993 | Schatz ........................ 606/195 |
| 5,197,978 A | 3/1993 | Hess ............................ 623/1 |
| 5,217,483 A | 6/1993 | Tower ........................ 606/198 |
| 5,226,913 A | 7/1993 | Pinchuk ........................ 623/1 |
| 5,282,823 A | 2/1994 | Schwartz et al. ............. 606/198 |
| 5,282,824 A | 2/1994 | Gianturco ................... 606/198 |
| 5,292,331 A | 3/1994 | Boneau ........................ 606/198 |
| 5,304,200 A | 4/1994 | Spaulding ................... 606/198 |
| 5,312,430 A | 5/1994 | Rosenbluth et al. ......... 606/192 |
| 5,314,472 A | 5/1994 | Fontaine ..................... 623/12 |
| 5,344,425 A | 9/1994 | Sawyer ........................ 606/198 |
| 5,354,308 A | 10/1994 | Simon et al. ................ 606/198 |
| 5,383,892 A | 1/1995 | Cardon et al. .............. 606/198 |
| 5,389,106 A | 2/1995 | Tower ........................ 606/198 |
| 5,405,377 A | 4/1995 | Cragg ........................... 623/1 |
| 5,449,373 A | 9/1995 | Pinchasik et al. ........... 606/198 |
| 5,507,767 A | 4/1996 | Maeda et al. ................ 606/198 |
| 5,527,354 A | 6/1996 | Fontaine et al. ................ 623/1 |
| 5,545,210 A | 8/1996 | Hess et al. ...................... 623/1 |
| 5,549,663 A | 8/1996 | Cottone, Jr. ..................... 623/1 |
| 5,591,197 A | 1/1997 | Orth et al. ................... 606/198 |
| 5,593,442 A | 1/1997 | Klein ........................... 623/12 |
| 5,607,442 A | 3/1997 | Fischell et al. .............. 606/191 |
| 5,613,981 A | 3/1997 | Boyle et al. ................. 606/198 |
| 5,653,727 A | 8/1997 | Wiktor ........................ 606/195 |
| 5,669,924 A | 9/1997 | Shaknovich ................ 606/108 |
| 5,676,671 A | 10/1997 | Inoue ........................ 606/108 |
| 5,695,516 A | 12/1997 | Fischell et al. .............. 606/198 |
| 5,697,971 A | 12/1997 | Fischell et al. ................. 623/1 |
| 5,707,386 A | 1/1998 | Schnepp-Pesch et al. ... 606/194 |
| 5,713,949 A | 2/1998 | Jayaraman ..................... 623/1 |
| 5,718,713 A | 2/1998 | Frantzen ..................... 606/198 |
| 5,733,301 A | 3/1998 | Forman ........................ 606/192 |
| 5,733,303 A | 3/1998 | Israel et al. .................. 606/198 |
| 5,735,871 A | 4/1998 | Sgro ........................... 606/198 |
| 5,735,893 A | 4/1998 | Lau et al. ........................ 623/1 |
| 5,741,327 A | 4/1998 | Frantzen ........................ 623/1 |
| 5,755,776 A | 5/1998 | Al-Saadon ..................... 623/1 |
| 5,755,781 A | 5/1998 | Jayaraman ..................... 623/1 |
| 5,759,192 A | 6/1998 | Saunders ..................... 606/194 |
| 5,772,864 A | 6/1998 | Moller et al. .................. 205/73 |
| 5,776,161 A | 7/1998 | Globerman ................. 606/194 |
| 5,776,181 A | 7/1998 | Lee et al. ....................... 623/1 |
| 5,776,183 A | 7/1998 | Kanesaka et al. ............... 623/1 |
| 5,807,404 A | 9/1998 | Richter ........................... 623/1 |
| 5,810,767 A | 9/1998 | Klein ........................... 604/53 |
| 5,810,872 A | 9/1998 | Kanesaka et al. ........... 606/198 |
| 5,824,043 A | 10/1998 | Cottone, Jr. ..................... 623/1 |
| 5,824,059 A | 10/1998 | Wijay ........................... 623/1 |
| 5,827,321 A | 10/1998 | Roubin et al. ............... 606/195 |
| 5,836,951 A | 11/1998 | Rosenbluth et al. ......... 606/108 |
| 5,836,964 A | 11/1998 | Richter et al. ............... 606/194 |
| 5,843,120 A | 12/1998 | Israel et al. ................... 606/98 |
| 5,843,172 A | 12/1998 | Yan ............................... 623/1 |
| 5,861,027 A | 1/1999 | Trapp ........................... 623/1 |
| 5,876,449 A | 3/1999 | Starck et al. ................. 623/12 |
| 5,879,370 A | 3/1999 | Fischell et al. .............. 606/198 |
| 5,895,406 A | 4/1999 | Gray et al. ................... 606/198 |
| 5,897,588 A | 4/1999 | Hull et al. ...................... 623/1 |
| 5,902,317 A | 5/1999 | Kleshinski et al. ........... 606/198 |
| 5,902,332 A | 5/1999 | Schatz ........................... 623/1 |

| | | | |
|---|---|---|---|
| 5,911,754 A | 6/1999 | Kanesaka et al. | 623/1 |
| 5,913,895 A | 6/1999 | Burpee et al. | 623/1 |
| 5,922,019 A | 7/1999 | Hankh et al. | 623/1 |
| 5,922,020 A | 7/1999 | Klein et al. | 623/1 |
| 5,922,021 A | 7/1999 | Jang | 623/1 |
| 5,938,682 A | 8/1999 | Hojeibane et al. | 606/198 |
| 5,939,227 A | 8/1999 | Smith | 430/5 |
| 5,948,016 A | 9/1999 | Jang | 623/1 |
| 5,953,743 A | 9/1999 | Jeddeloh | 711/158 |
| 5,954,743 A | 9/1999 | Jang | 606/198 |
| 5,964,798 A | 10/1999 | Imran | 623/1 |
| 5,968,093 A | 10/1999 | Kranz | 623/1 |
| 5,972,027 A | 10/1999 | Johnson | 623/1 |
| 5,980,553 A | 11/1999 | Gray et al. | 606/198 |
| 6,033,433 A | 3/2000 | Ehr et al. | 623/1.16 |
| 6,039,756 A | 3/2000 | Jang | 623/1 |
| 6,042,606 A | 3/2000 | Frantzen | 623/1 |
| 6,053,940 A | 4/2000 | Wijay | 623/1 |
| 6,066,169 A | 5/2000 | McGuinness | 623/1.16 |
| 6,106,548 A | 8/2000 | Roubin et al. | 623/1.15 |
| 6,113,627 A | 9/2000 | Jang | 623/1 |
| 6,117,165 A | 9/2000 | Becker | 623/1 |
| 6,123,721 A | 9/2000 | Jang | 623/1 |
| 6,129,755 A | 10/2000 | Mathis et al. | 623/1.15 |
| 6,152,957 A | 11/2000 | Jang | 623/1.37 |
| 6,156,052 A | 12/2000 | Richter et al. | 606/191 |
| 6,162,243 A | 12/2000 | Gray et al. | 623/1.11 |
| 6,179,868 B1 | 1/2001 | Burpee et al. | 623/1.17 |
| 6,183,506 B1 | 2/2001 | Penn et al. | 623/1.15 |
| 6,190,403 B1 | 2/2001 | Fischell et al. | 623/1 |
| 6,190,404 B1 | 2/2001 | Palmaz et al. | 623/1.15 |
| 6,190,406 B1 | 2/2001 | Duerig et al. | 623/1.2 |
| 6,192,747 B1 | 2/2001 | Fennel | 73/146.2 |
| 6,193,744 B1 | 2/2001 | Ehr et al. | 623/1 |
| 6,193,747 B1 * | 2/2001 | von Oepen | 623/1.15 |
| 6,200,334 B1 | 3/2001 | Jang | 623/1.1 |
| 6,200,337 B1 | 3/2001 | Moriuchi et al. | 623/1.16 |
| 6,203,569 B1 | 3/2001 | Wijay | 623/1.15 |
| 6,206,911 B1 | 3/2001 | Milo | 623/1.15 |
| 6,206,915 B1 | 3/2001 | Fagan et al. | 623/1.42 |
| 6,206,916 B1 | 3/2001 | Furst | 623/1.46 |
| 6,217,608 B1 | 4/2001 | Penn et al. | 623/1.16 |
| 6,231,598 B1 | 5/2001 | Berry et al. | 623/1.15 |
| 6,235,053 B1 | 5/2001 | Jang | 623/1.15 |
| 6,241,760 B1 | 6/2001 | Jang | 623/1.12 |
| 6,251,134 B1 | 6/2001 | Alt et al. | 623/1.16 |
| 6,254,632 B1 | 7/2001 | Wu et al. | 623/1.15 |
| 6,258,121 B1 | 7/2001 | Yang et al. | 623/1.46 |
| 6,261,319 B1 | 7/2001 | Kveen et al. | 623/1.15 |
| 6,261,320 B1 | 7/2001 | Tam et al. | 623/1.15 |
| 6,270,524 B1 | 8/2001 | Kim | 623/1.15 |
| 6,273,908 B1 | 8/2001 | Ndondo-Lay | 623/1 |
| 6,273,911 B1 | 8/2001 | Cox et al. | 623/1.15 |
| 6,273,913 B1 | 8/2001 | Wright et al. | 623/1.42 |
| 6,280,413 B1 | 8/2001 | Clark et al. | 604/104 |
| 6,331,189 B1 | 12/2001 | Wolinsky et al. | 623/1.15 |
| 6,348,065 B1 | 2/2002 | Brown et al. | 623/1.16 |
| 6,355,059 B1 | 3/2002 | Richter et al. | 623/1.17 |
| 6,379,381 B1 | 4/2002 | Hossainy et al. | 623/1.42 |
| 6,409,761 B1 | 6/2002 | Jang | 623/6.12 |
| 6,416,538 B1 | 7/2002 | Ley et al. | 623/1.15 |
| 6,423,090 B1 | 7/2002 | Hancock | 623/1.15 |
| 6,432,133 B1 | 8/2002 | Lau et al. | 623/1.15 |
| 6,443,982 B1 | 9/2002 | Israel et al. | 623/1.17 |
| 6,451,049 B2 | 9/2002 | Vallana et al. | 623/1.15 |
| 6,461,380 B1 | 10/2002 | Cox | 623/1.17 |
| 6,461,381 B2 | 10/2002 | Israel et al. | 623/1.17 |
| 6,464,720 B2 | 10/2002 | Boatman et al. | 623/1.15 |
| 6,464,722 B2 | 10/2002 | Israel et al. | 623/1.17 |
| 6,468,302 B2 | 10/2002 | Cox et al. | 623/1.15 |
| 6,471,720 B1 | 10/2002 | Ehr et al. | 623/1.15 |
| 6,475,236 B1 | 11/2002 | Roubin et al. | 623/1.15 |
| 6,478,816 B1 | 11/2002 | Kveen et al. | 623/1.15 |
| 6,485,508 B1 | 11/2002 | McGuinness | 623/1.15 |
| 2001/0010013 A1 | 7/2001 | Cox et al. | 623/1.15 |
| 2001/0020183 A1 | 9/2001 | Jang | 623/1.15 |
| 2001/0035783 A1 | 11/2001 | Kanba | 327/202 |
| 2002/0038145 A1 | 3/2002 | Jang | 623/1.15 |
| 2002/0042647 A1 | 4/2002 | Jang | 623/1.15 |
| 2002/0045933 A1 | 4/2002 | Jang | 623/1.15 |
| 2002/0045934 A1 | 4/2002 | Jang | 623/1.15 |
| 2002/0045935 A1 | 4/2002 | Jang | 623/1.16 |
| 2002/0049493 A1 | 4/2002 | Jang | 623/1.16 |
| 2002/0058990 A1 | 5/2002 | Jang | 623/1.15 |
| 2002/0161429 A1 | 10/2002 | Jang | 623/1.15 |
| 2002/0193870 A1 | 12/2002 | Jang | 623/1.16 |
| 2003/0028242 A1 | 2/2003 | Vallana et al. | 623/1.15 |
| 2004/0153141 A1 | 8/2004 | Penn et al. | 623/1.16 |

FOREIGN PATENT DOCUMENTS

| | | |
|---|---|---|
| EP | 0 734 698 A2 | 2/1996 |
| EP | 0 821 920 A1 | 2/1998 |
| EP | 0 875 215 A1 | 11/1998 |
| EP | 0 980 694 A2 | 2/2000 |
| FR | 2 785 174 A1 | 5/2000 |
| WO | WO 95/08975 A1 | 2/1996 |
| WO | WO 00/03661 A1 | 1/2000 |
| WO | WO 00/13611 A1 | 3/2000 |
| WO | WO 00/30563 A1 | 6/2000 |
| WO | WO 00/62710 A1 | 10/2000 |
| WO | WO 01/26584 A1 | 4/2001 |
| WO | WO 01/66036 A2 | 9/2001 |
| WO | WO 01/91918 | 12/2001 |
| WO | WO 01/93781 A2 | 12/2001 |
| WO | WO 02/24112 A2 | 3/2002 |
| WO | 2004/026180 | 4/2004 |

OTHER PUBLICATIONS

U.S. Appl. No. 10/297,372, filed Dec. 5, 2002, Jang.
U.S. Appl. No. 10/321,005, filed Dec. 17, 2002, Jang.
U.S. Appl. No. 60/073,412, filed Feb. 2, 1998, Jang.
U.S. Appl. No. 60/073,509, filed Feb. 3, 1998, Jang.
U.S. Appl. No. 60/234,614, filed Sep. 22, 2000, Jang.
U.S. Appl. No. 60/235,115, filed Sep. 25, 2000, Jang.
U.S. Appl. No. 60/235,164, filed Sep. 23, 2000, Jang.
U.S. Appl. No. 60/017,484, filed Apr. 26, 1996, Jang.
U.S. Appl. No. 09/574,077, filed May 18, 2000, Jang.
U.S. Appl. No. 60/235,167, filed Sep. 23, 2000, Jang.
U.S. Appl. No. 60/235,180, filed Sep. 25, 2000, Jang.
U.S. Appl. No. 08/845,734, filed Apr. 25, 1997, Jang.
Continued videotaped deposition of James E. Moore, Jr., Ph.D., held at the offices of Kirkland & Ellis, LLP, 153 East 53$^{rd}$ Street, New York, New York, pursuant to adjournment , before Cary N. Bigelow, RPR, a Notary Public of the State of New York, dated Mar. 18, 2005, 8:33 a.m. (Case No. 03-027-SLR).
Videotaped deposition of James E. Moore, Jr., Ph.D., held at the offices of Kirkland & Ellis, LLP, 153 East 53$^{rd}$ Street, New York, New York, pursuant to notice, before Cary N. Bigelow, RPR, a Notary Public of the State of New York, dated Mar. 17, 2005, 9:32 a.m. (Case No. 03-027-SLR).
Corrected Rebuttal Expert Report of Professor James E. Moore Jr., Ph.D., dated Mar. 14, 2005 (Case No. 03-027-SLR).
Corrected Expert Report of Professor James E. Moore Jr., Ph.D., dated Feb. 11, 2005 (Case No. 03-027-SLR).
Opening Expert Report of Nigel Buller, B.SC, M.B., F.R.C.P. regarding Validity of the Jang Patent (Case No. 03-027-SLR).
Deposition of Nigel Buller, held at the offices of Patterson, Belknap, Webb & Tyler, 1133 Avenue of the Americas, New York, New York, before Laurie A. Collins, a Registered Professional Reporter and Notary Public of the State of New York, dated Mar. 2, 2005, 9:32 a.m. (Case No. 03-027-SLR).
Continued deposition of Nigel Buller, held at the offices of Patterson, Belknap, Webb & Tyler, 1133 Avenue of the Americas, New York, New York, before Laurie A. Collins, a Registered Professional Reporter and Notary Public of the State of New York, dated Mar. 3, 2005, 8:45 a.m. (Case No. 03-027-SLR).

Rebuttal Expert Report of Nigel Buller, B.SC., M.B., F.R.C.P., dated Feb. 25, 2005 (Case No. 03-027-SLR).

Videotaped Deposition of the David Morre Parks, Ph.D., a witness called on behalf of the Defendants, pursuant to the Federal Rules of Civil Procedure, before Judith McGovern Williams, Certified Shorthand Reporter No. 130993, Registered Professional Reporter, Certified Realtime Reporter, and Notary Public in and for the Commonwealth of Massachusetts, at the Hyatt Regency, 575 Memorial Drive, Cambridge, Massachusetts, on Monday, Mar. 21, 2005, commencing at 9:32 a.m. (Case No. 03-027-SLR).

Opening Expert Report of David M. Parks, Ph.D. Regarding Validity of the Jang Patent, dated Jan. 28, 2005 (Case No. 03-027-SLR).

Rebuttal Expert Report of David M. Parks, Ph.D., dated Feb. 25, 2005 (Case No. 03-027-SLR).

BSC's Opposition to Cordis' Motion for Summary Judgment of Noninfringement of Claim 36 of the Jang '021 Patent, dated Apr. 14, 2005 (Case No. 03-027-SLR).

Redacted Version—Publicly Filed BSC's Opposition to Cordis' Motion for Summary Judgment of Noninfringement of Claim 36 of the Jang '021 Patent, dated Apr. 14, 2005 (Case No. 03-027-SLR).

Redacted Public Version: Opening Brief in Support of Cordis' Motion for Summary Judgement of Noninfringement of Claim 36 of the Jang '021 Patent, dated Mar. 31, 2005 (Case No. 03-027-SLR).

Opening Brief in Support of Cordis' Motion for Summary Judgment of Noninfringement of Claim 36 of the Jang '021 Patent, dated Mar. 24, 2005 (Case No. 03-027-SLR).

Reply Brief in Support of Cordis' Motion for Summary Judgment of Noninfringement of the Jang '021 Patent, dated Apr. 21, 2005 (Case No. 03-027-SLR).

Order, dated Jun. 3, 2005 (Case No. 03-027-SLR).

Jury Verdict, dated Jul. 1, 2005 (Case No. 03-027-SLR and Case No. 03-283-SLR).

Jury Trial—vol. H, *BSC v. Cordis & J&J*, CA #03-27 & 03-283 (SLR), dated Friday, Jul. 1, 2005, pp. 1816-1857 and Index pp. 1-7.

Jury Trial—vol. A, *BSC v. Cordis & J&J*, CA #03-27 & 03-283 (SLR), dated Tuesday, Jun. 21, 2005, pp. 1-107 and Index pp. 1-12.

Jury Trial—vol. B, *BSC v. Cordis & J&J*, CA #03-27 & 03-283 (SLR), dated Wednesday, Jun. 22, 2005, pp. 108-407 and Index pp. 1-32.

Jury Trial—vol. C, *BSC v. Cordis & J&J*, CA #03-27 & 03-283 (SLR), dated Thursday, Jun. 23, 2005, pp. 408-691 and Index pp. 1-29.

Jury Trial—vol. D, *BSC v. Cordis & J&J*, CA #03-27 & 03-283 (SLR), dated Friday, Jun. 24, 2005, pp. 693-930 and Index pp. 1-23.

Jury Tria—vol. E, *BSC v. Cordis & J&J*, CA #03-27 & 03-283 (SLR), dated Jun. 28, 2005, pp. 931-1223.

Under Seal—vol. EE, *BSC v. Cordis & J&J*, CA #03-27 & 03-283 (SLR), dated Tuesday Jun. 28, 2005, pp. 1-61 and Index pp. 1-8.

Jury Trial—vol. F, *BSC v. Cordis & J&J*, CA #03-27 & 03-283 (SLR), dated Wednesday, Jun. 29, 2005, pp. 1224-1537 and Index pp. 1-32.

Jury Trial —vol. G, *BSC v. Cordis & J&J*, CA #03-27 & 03-283 (SLR), dated Thursday, Jun. 30, 2005, pp. 1528-1815 and Index pp. 1-30.

\* cited by examiner

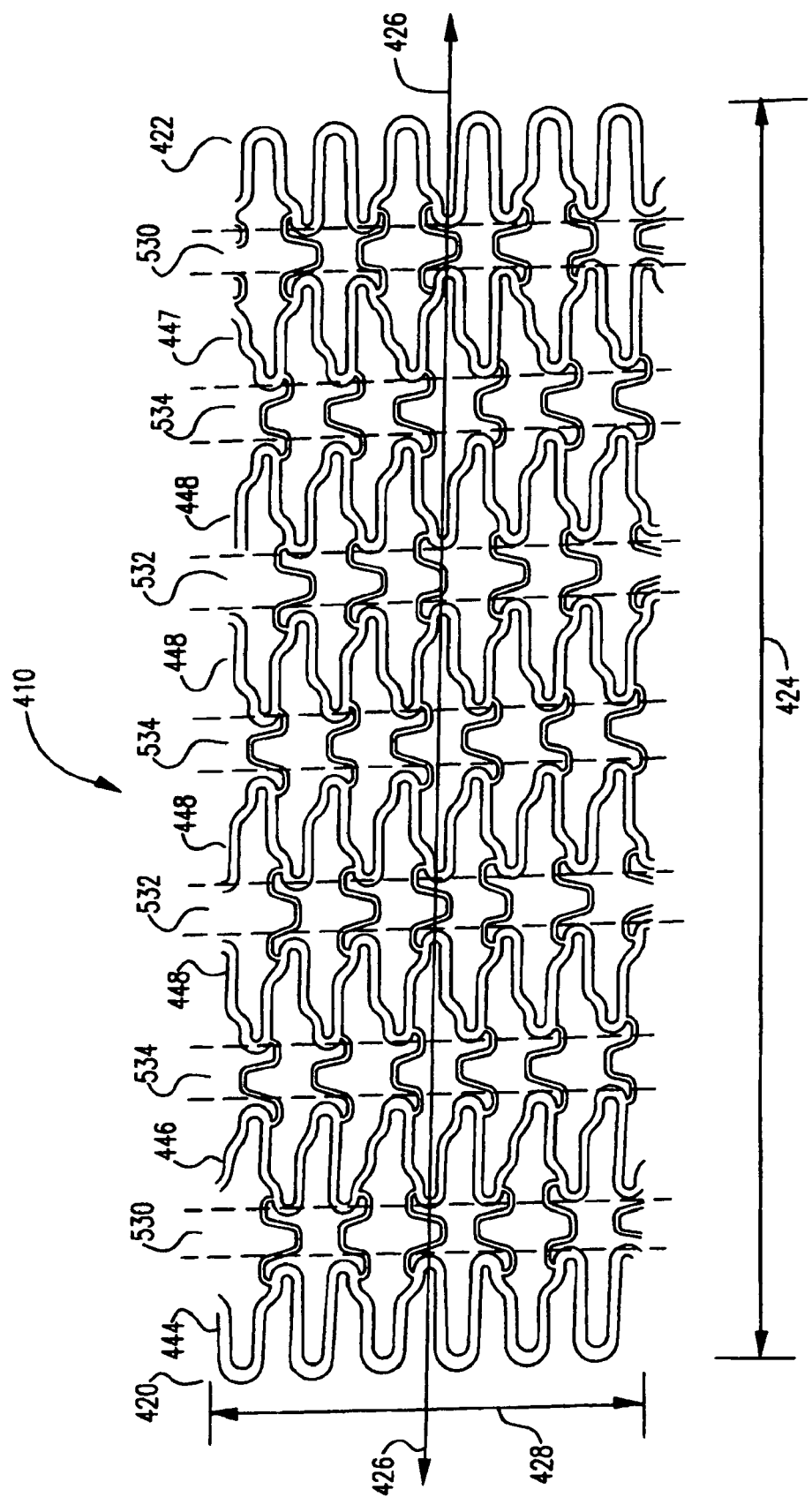

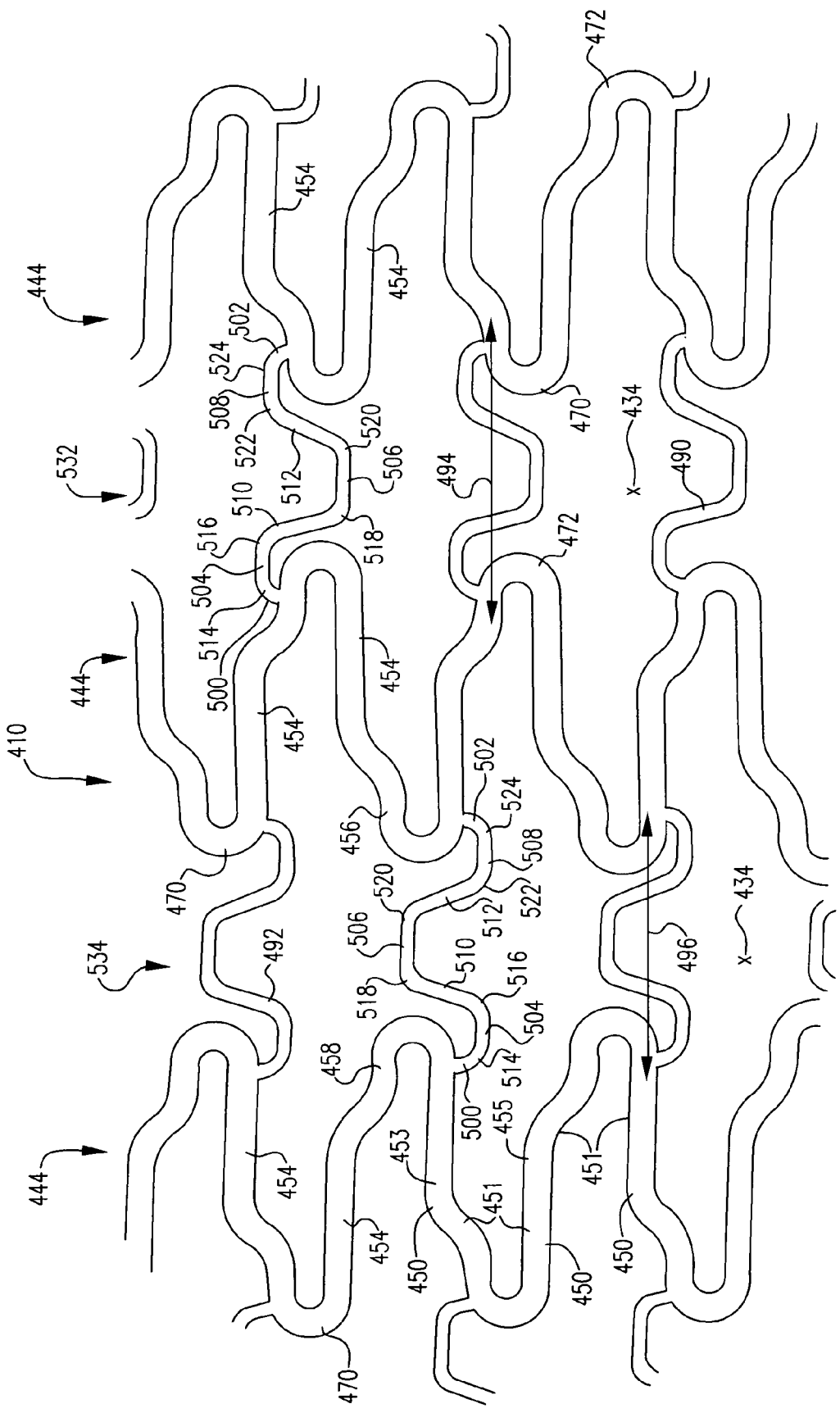

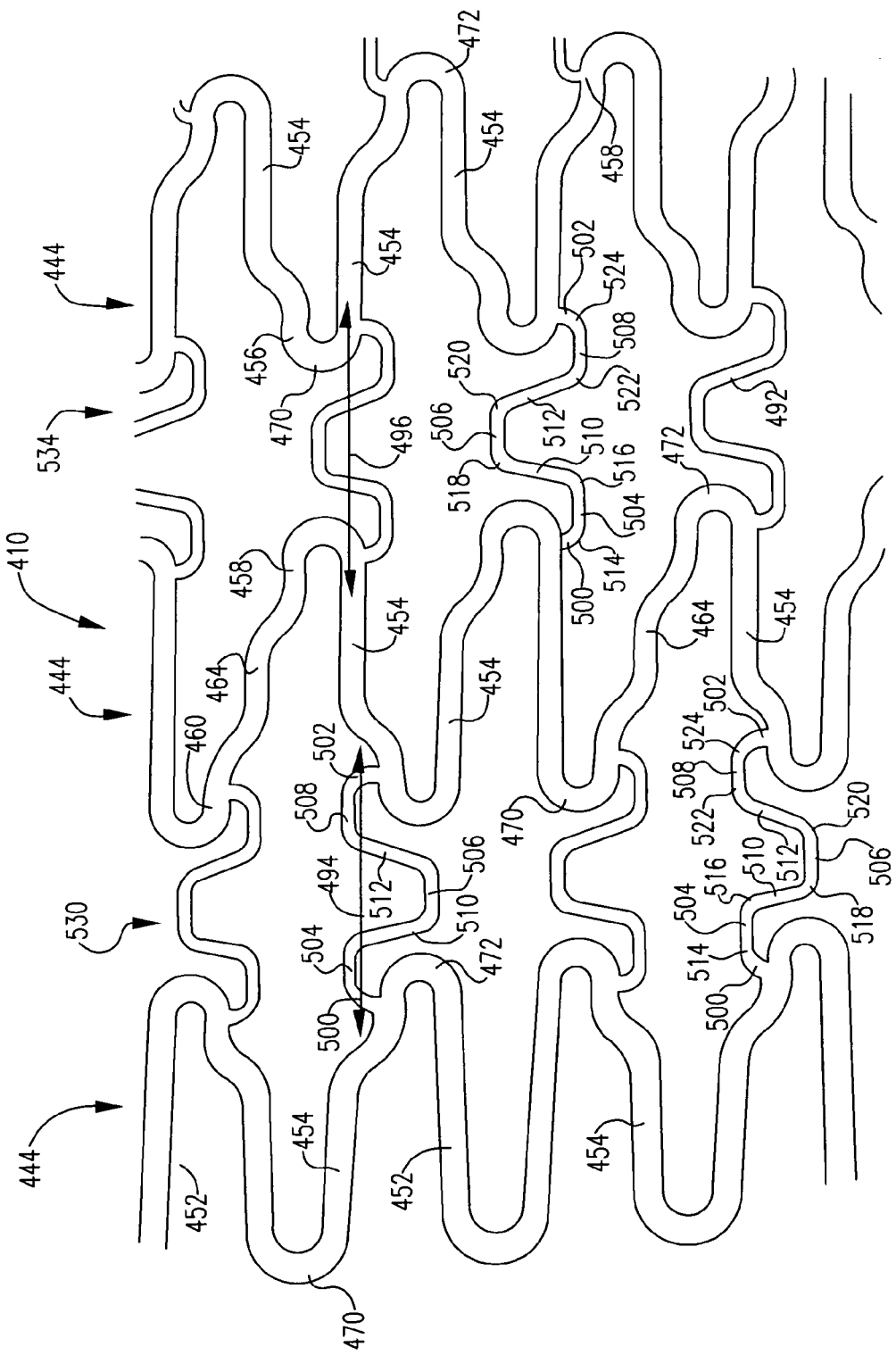

INTRAVASCULAR STENT AND ASSEMBLY

CROSS REFERENCE TO RELATED APPLICATION

This application is a continuation-in-part (CIP) of U.S. application Ser. No. 09/960,861, filed Sep. 21, 2001, which claims the benefit of U.S. Provisional Application 60/234,614, filed Sep. 22, 2000.

This application is also a continuation-in-part (CIP) of U.S. application Ser. No. 09/963,125, filed Sep. 24, 2001, which claims the benefit of U.S. Provisional Application 60/235,167, filed Sep. 23, 2000.

This application is also a continuation-in-part (CIP) of U.S. application Ser. No. 09/960,868, filed Sep. 21, 2001, which claims the benefit of U.S. Provisional Application 60/235,115, filed Sep. 23, 2000.

This application is also a continuation-in-part (CIP) of U.S. application Ser. No. 09/962,792, filed Sep. 24, 2001, which claims the benefit of U.S. Provisional Application 60/235,180, filed Sep. 25, 2000.

This application is also a continuation-in-part (CIP) of U.S. application Ser. No. 09/942,077, filed Aug. 28, 2001, which claims the benefit of U.S. Provisional Application 60/235,164, filed Sep. 23, 2000.

Each of the above referenced Applications being incorporated in their entirety by reference.

BACKGROUND OF THE INVENTION

1. Field of Invention

This invention relates to intravascular stents in general, and more particularly to intracoronary stents.

2. Description of the Related Art

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, mechanically expandable or hybrid expandable.

Stents are generally tubular devices for insertion into body lumens. However, it should be noted that stents may be provided in a wide variety of sizes and shapes. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

Due to the branching nature of the human vasculature it is not uncommon for stenoses to form at any of a wide variety of vessel bifurcations. A bifurcation is an area of the vasculature or other portion of the body where a first (or parent) vessel is bifurcated into two or more branch vessels. In some cases it may be necessary to implant multiple stents at the bifurcation in order to address a stenosis located thereon. Alternatively, a stent may be provided with multiple sections or branches that may be deployed within the branching vessels of the bifurcation.

Stents may be constructed from a variety of materials such as stainless steel, Elgiloy, nickel, titanium, nitinol, shape memory polymers, etc. Stents may also be formed in a variety of manners as well. For example a stent may be formed by etching or cutting the stent pattern from a tube or section of stent material; a sheet of stent material may be cut or etched according to a desired stent pattern whereupon the sheet may be rolled or otherwise formed into the desired substantially tubular, bifurcated or other shape of the stent; one or more wires or ribbons of stent material may be woven, braided or otherwise formed into a desired shape and pattern.

Typically, a stent is implanted in a blood vessel or other body lumen at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to expand to a predetermined diameter in the vessel.

Some of the best selling current, second generation, stents can be divided into two categories. One category is a stent with flexibility and the other with good vessel coverage. The flexible current stents generally have poor vessel coverage, tissue prolapse, rough surface modulation and increased restenosis rate. On the other hand, a good vessel coverage stent in the current state of art has better vessel coverage but not flexible enough for easy delivery and efficient procedure. This means that an ideal stent that has good flexibility and good vessel coverage remains as the gold standard that has not yet been reached.

To further reduce the restenosis rate after stent implant, numerous means has been tried, including laser, atherectomy, high frequency ultrasound, radiation device, local drug delivery, etc. Although the brachytherapy (radiation treatment) has proved to be reasonably effective in further reducing restenosis after stent implant, using brachytherpy is very cumbersome, inconvenient and costly. Mainly because it is radioactive device and radiation therapy specialist from another department has to be involved with the interventional cardiologist in the cardiac catheterization laboratory. The laser and atherectomy devices proved to be marginally useful in this purpose with added costs. Even if these measures would reduce the restenosis rate in theory or in real terms, an ideal stent that has good vessel coverage and flexibility would produce even better outcomes.

Despite the wide variety of stents presently available, there remains a desire to provide stents and stent designs which provide a more optimized combination of improved flexibility and good vessel coverage.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

In light of the above the present invention is directed to a variety of embodiments. In at least one embodiment a stent is provided that provides a more optimized combination of flexibility and vessel coverage. In some embodiments the stent is balloon expandable. In some embodiments the stent is self-expandable. In some embodiments the stent is hybrid expandable.

Various embodiments of a stent include a combination of maximum possible flexibility and conformability in the stent, full vessel coverage with optimal metal fraction, evenly expanding stent struts, excellent radial strength and radiopacity, and smooth surface modulations in both delivery and deployed phases of the stent life cycle. To arrive at these goals, many detailed new innovations are added to the expansion and connecting strut designs of the stent. Expansion strut design is largely responsible for radial strength and radiopacity, while connecting strut design is largely responsible for flexibility and smooth surface modulations. Full vessel coverage and uniform stent expansion are largely from interaction between expansion and connecting struts. Various embodiments of the stent demonstrate a balance among these multiple qualities, using smart expansion struts and flexible connecting struts in a seamlessly integrated stent network.

Various embodiments of the stent are specifically designed to be both very flexible and fully cover vessel surface inside the vascular lumen. The stent can have both characteristics of vessel coverage and flexibility, particularly for coronary use.

Various embodiments of the stent are well designed for both the delivery phase and the deployed phase of the stent life cycle. Both flexibility and good vessel coverage are in a right balance in various embodiments of the stent have. Various embodiments of the stent include certain configurations in expansion and connecting struts of the stent.

Some embodiments of the stent include a stent in a non-expanded state, which comprises a first expansion column and a second expansion column and a connecting strut column extending therebetween. In some embodiments each expansion column includes individual expansion struts that form a plurality of expansion strut pairs. At least a portion of each first expansion strut defines a stair-step region or pattern. Two adjacent first expansion strut pairs share a common strut.

In some embodiments the connecting strut column includes a plurality of non-intersecting-individual first connecting struts that couple only the adjacent expansion columns. Each connecting strut includes a proximal section and a distal section, wherein at least a portion of the proximal section of each connecting strut extends from a portion of the stair-step region of the expansion struts of the first expansion column and at least a portion of the distal section of each connecting strut extends from a portion of the stair-step region of one of the second expansion struts. In some embodiments each proximal section has a longitudinal axis and each distal section has a longitudinal axis, at least one of the longitudinal axis of each proximal section and the longitudinal axis of the distal section is parallel with at least one of a longitudinal axis of each expansion strut of one or both expansion strut columns.

In at least one embodiment each connecting strut of one or both columns has a stair-step configuration.

In at least one embodiment one expansion strut of an expansion strut pair has a stair-step segment at a proximal end and a stair-step segment at a distal end.

In at least one embodiment one expansion strut of an expansion strut pair is a straight segment.

In at least one embodiment a section of one or more connecting struts has an edge that is a linear extension of an edge of one or both expansion struts to which the connecting strut connects.

In at least one embodiment a strain relief notch is formed where the edge of the connecting strut is conjoined with the edge of an expansion strut.

In at least one embodiment the distal section of one or more connecting struts of one or more connecting strut columns has a greater length than its proximal section.

In at least one embodiment each connecting struts is ipsilaterally conjoined to the first and second expansion columns.

In at least one embodiment each connecting strut is contralaterally conjoined to the first and second expansion columns.

In at least one embodiment the longitudinal axis of the proximal section of each connecting strut is non-parallel to the longitudinal axis of its distal section.

In at least one embodiment each connecting strut includes an intermediate section coupled to the proximal and distal sections. In some embodiments the intermediate section of each connecting strut has a greater length than a length of its proximal section and/or distal section. In some embodiments at least a portion of the intermediate section of each connecting strut has a curvilinear geometric configuration. In some embodiments at least a portion of the proximal and distal sections of each connecting strut have a curvilinear geometric configuration. In some embodiments the intermediate section of each connecting strut has a longitudinal axis that is non-parallel to a longitudinal axis of the stent. In some embodiments the intermediate section of each connecting strut has a longitudinal axis that is positioned diagonally relative to a longitudinal axis of the stent. In some embodiments the intermediate section of each connecting strut has a longitudinal axis that extends in a vertically diagonal direction relative to a longitudinal axis of the stent. In some embodiments at least a portion of the intermediate section of each connecting strut is in close proximity to an expansion strut pair of the first expansion column.

In at least one embodiment a width of the proximal section of each connecting strut is less than a width of an expansion strut.

In at least one embodiment the stent further comprises a plurality of expansion columns coupled by a plurality of connecting strut columns.

In at least one embodiment the stent is a bifurcated stent.

In at least one embodiment at least a portion of the stent is coated with at least one therapeutic agent.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF DRAWINGS

A detailed description of the invention is hereafter described with specific reference being made to the drawings.

FIG. 18 shows a cut-open view of an embodiment of a stent. Various expansion columns and connecting strut columns are shown.

FIG. 19B shows a magnified view of a middle section of an embodiment of a stent, such as a stent of FIGS. 16, 17, and/or 18. Some details are shown of connecting strut columns conjoined with expansion columns.

FIG. 20B shows a magnified view of an end section of one embodiment of a stent, such as a stent of FIGS. 16, 17, and/or 18. of present invention in a two-dimensional view. Some details are shown of different connecting strut columns conjoined with expansion columns.

DETAILED DESCRIPTION OF DRAWINGS

Figure 1:
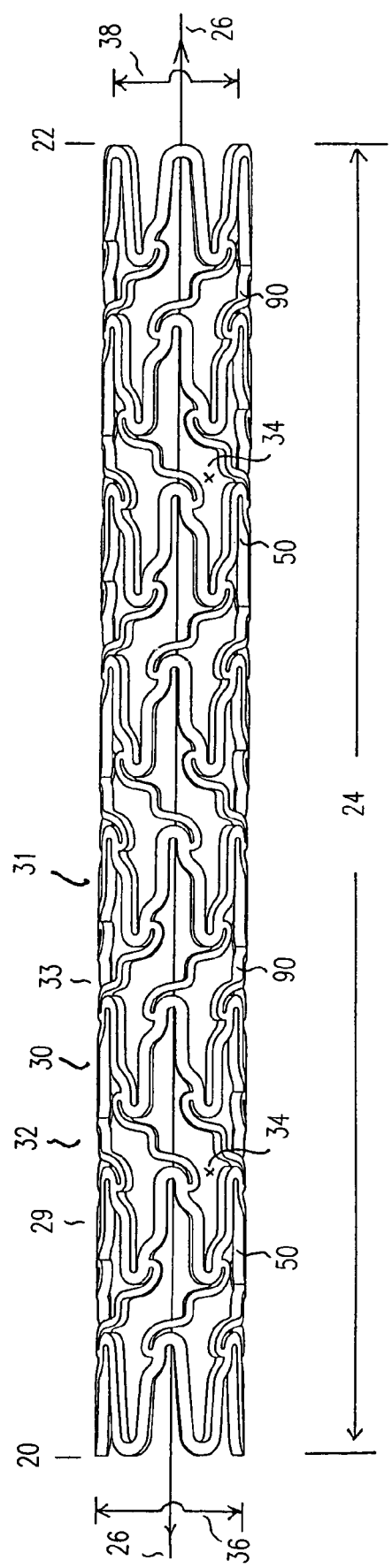
FIG. 1 shows a side elevation view of an embodiment of a stent, such as a tubular stent.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Some embodiments of stents can be in a state, such as one or more of a non-expanded state, an expanded state, a crimped state, and a non-crimped state.

Some embodiments of stents can include one or more of a first expansion column, a second expansion column, a third expansion column, a first connecting strut column, and a second connecting strut column.

Figure 4:
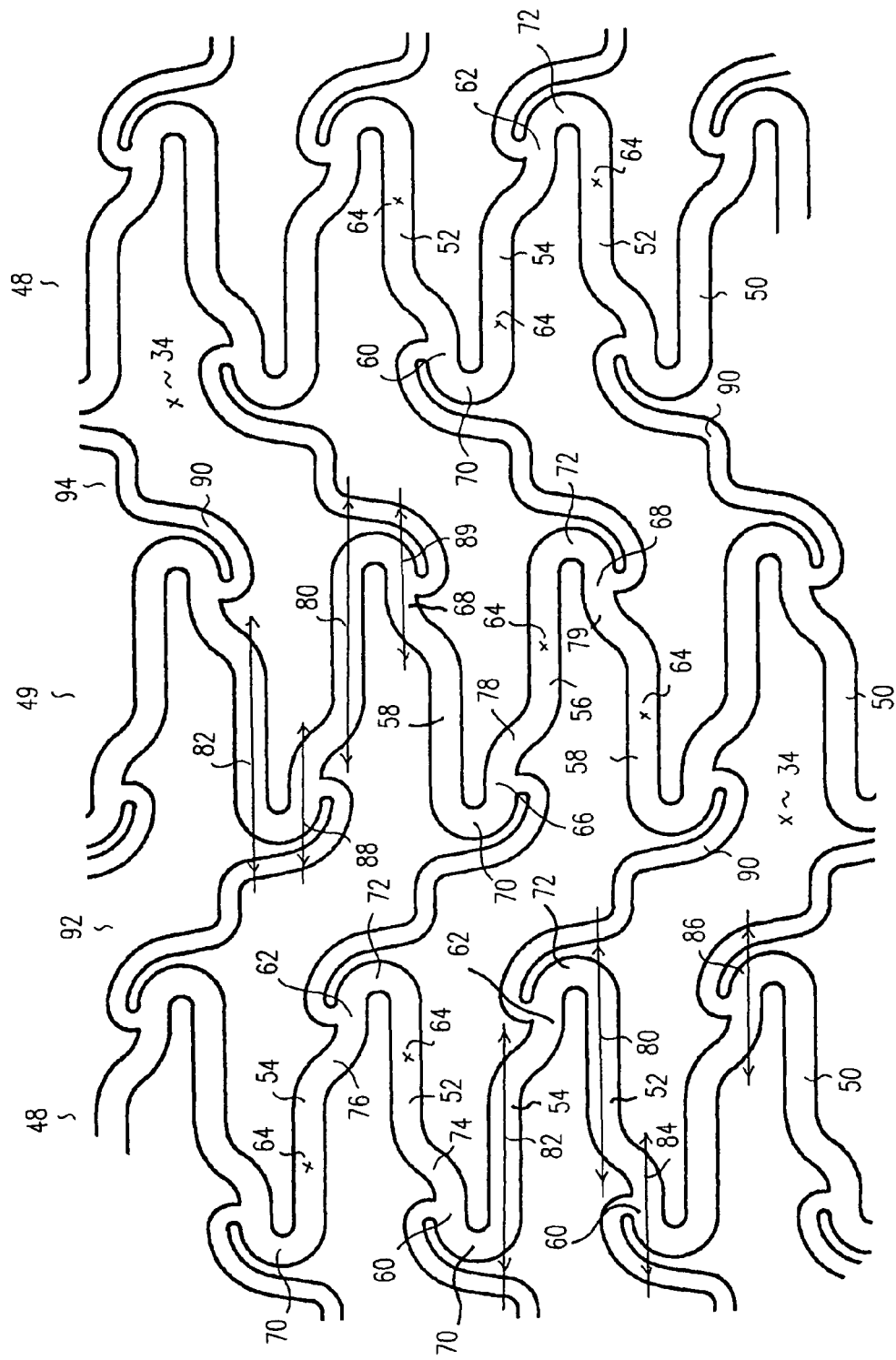
FIG. 4 shows a magnified view of a middle section of an embodiment of a stent, such as a stent of FIGS. 1, 2, and/or 3. Some details are shown of expansion columns.

In at least one embodiment of the invention shown in FIG. 4, the first expansion column, represented at (4A), the second expansion column, represented at (4B), and/or the third expansion column, represented at (4C), may include individual expansion struts forming a plurality of expansion strut pairs. FIG. 4 shows examples of individual expansion struts 50 forming a plurality of expansion strut pairs 51. In some embodiments of the stent, one expansion strut of an expansion strut pair has a stair-step segment at a proximal end and/or a stair-step segment at a distal end. The other expansion strut of the expansion strut pair can be a straight segment.

FIG. 4 also shows examples of one expansion strut 54 of an expansion strut pair having a stair-step segment at a proximal end or a stair-step segment at a distal end. FIG. 4 also shows examples of the other expansion strut 52 of the expansion strut pair being a straight segment. In some embodiments of the stent, distal ends of expansion strut pairs of the first expansion column are coupled to proximal ends of expansion strut pairs of the second expansion column in a vertically or circumferentially offset fashion. In many embodiments of the stent, two adjacent expansion strut pairs share a common strut.

The first connecting strut column and the second connecting strut column include a plurality of individual connecting struts. The first connecting strut column can include individual first connecting struts and the second connecting strut column can include individual second connecting struts. The individual first connecting column couples the first and second expansion columns. The second connecting column couples the second and third expansion columns.

In various embodiments of the stent, each connecting strut can have a stair-step configuration, at least some number of pivot points, a same longitudinal axis as other connecting struts in the same connecting column, and various sections such as a proximal section, an intermediate section, and a distal section. A connecting strut can have at least two pivot points. Each pivot point can include a radius of curvature. In the embodiment shown in FIG. 5 for example, connecting struts are shown with pivot points having radii of curvature 106 and 108. The longitudinal axes of connecting struts in a connecting column have the same direction.

Figure 5:
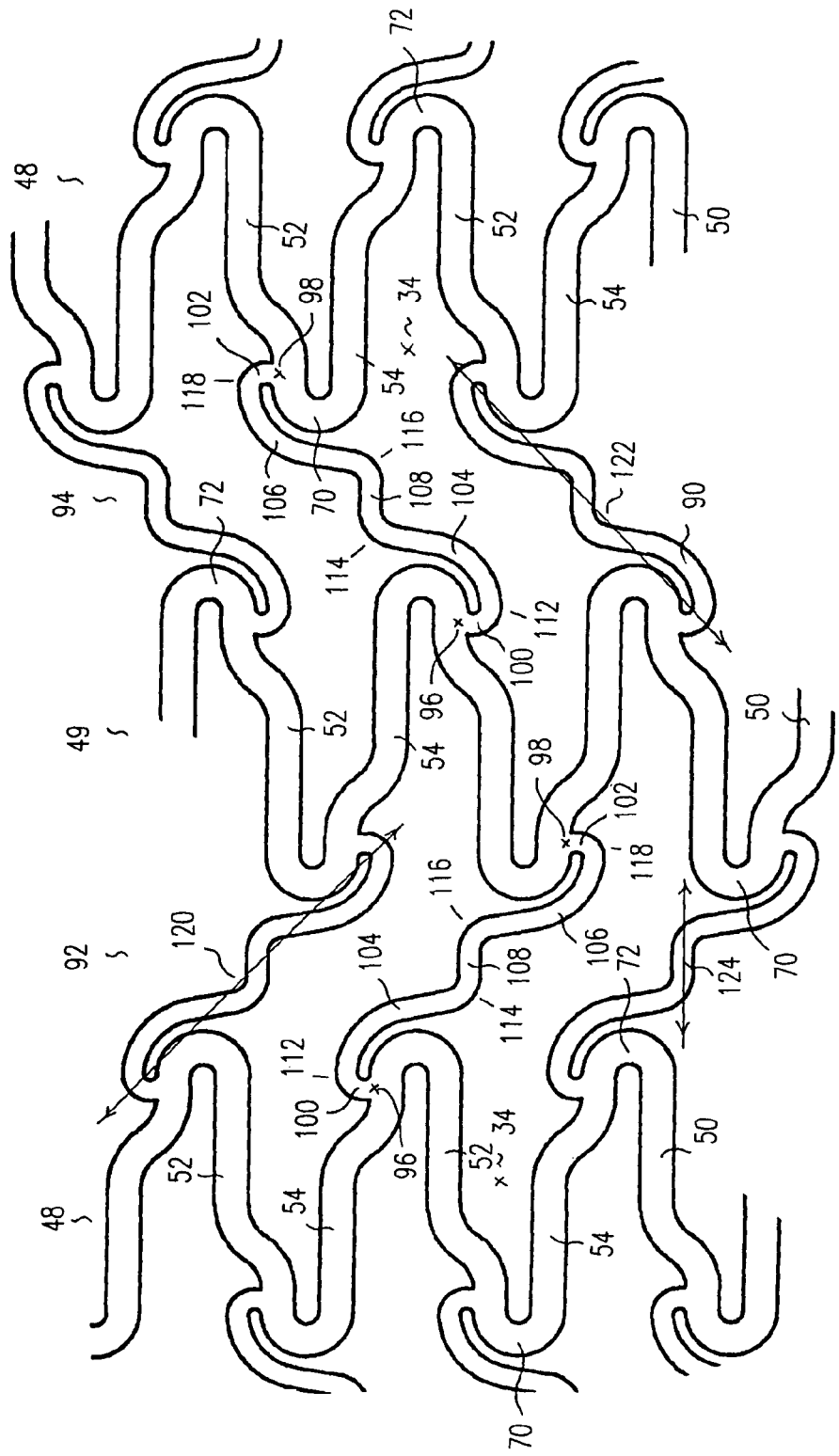
FIG. 5 shows a magnified view of a middle section of an embodiment of a stent, such as a stent of FIGS. 1, 2, and/or 3. Some details are shown of connecting strut columns.

FIG. 5 shows examples of a longitudinal axis 110 of a connecting strut which has the same longitudinal axis as other connecting struts in the same column, and a longitudinal axis 112 which has the same longitudinal axis as other connecting struts in the same connecting column.

In various embodiments of the stent, the proximal section of each first connecting strut in a connecting column, indicated at (5A) and (5B) in FIG. 5, has a terminal end 96 conjoined to an expansion strut in the first expansion column. A surface of the connecting strut can be conjoined to at least one surface of an expansion strut in the first expansion column. An edge of a connecting strut can be a linear extension of an edge of an expansion strut in the first expansion column. A strain relief notch can be formed where the edge of the proximal section is conjoined with the edge of the expansion strut of the first expansion column. FIG. 5 shows an example of a strain relief notch 119 formed where the edge of the terminal end 96 of the proximal section is conjoined with the edge of the expansion strut of the first expansion column. At least one proximal section of a connecting strut can be a direct extension of an expansion strut pair of the first expansion column.

FIG. 5 shows an example of a proximal section 100 which can be a direct extension of an expansion strut pair that includes expansion strut 53. The longitudinal axis can be non-parallel to the longitudinal axis of the distal section. FIG. 5 shows an example of a longitudinal axis 115 of a proximal section is non-parallel to the longitudinal axis 117 of the distal section. The longitudinal axis can be parallel to the longitudinal axis of an expansion strut in the first expansion column. FIG. 5 shows an example of a longitudinal axis 115 of a proximal section, which is parallel to the longitudinal axis 82 of an expansion strut of the first expansion column. The width of a connecting strut column in a connecting strut can be less than a width of the expansion strut in an expansion column. FIG. 5 shows an example of a width of a proximal section 100, which is less than a width of an expansion strut 54 of the first expansion column.

In various embodiments of the stent, the proximal section of each second connecting strut can include one or more of a terminal end conjoined to an expansion strut in the second expansion column, a surface conjoined to at least one surface of an expansion strut in the second expansion column, an edge that is a linear extension of an edge of an expansion strut in the second expansion column, a longitudinal axis, and a width. A strain relief notch can be formed where the edge of the proximal section is conjoined with the edge of the expansion strut of the second expansion column. FIG. 5 shows an example of a strain relief notch 121 formed where the edge of the proximal section is conjoined with the edge of the expansion strut of the second expansion column. At least one proximal section can be a direct extension of an expansion strut pair of the first expansion column and/or the second expansion column. FIG. 5 shows an example of a proximal section 101, which is a direct extension of either expansion strut pair including expansion strut 55. The longitudinal axis can be non-parallel to the longitudinal axis of the distal section. FIG. 5 shows an example of a longitudinal axis 114, which is non-parallel to the longitudinal axis 116 of the distal section. The longitudinal axis can be parallel to the longitudinal axis of an expansion strut in the second expansion column. FIG. 5 shows an example of a longitudinal axis 114, which is parallel to the longitudinal axis 83 of an expansion strut of the second expansion column. The width can be less than a width of the expansion strut of the second expansion column. FIG. 5 shows an example of a width of a proximal section 101, which is less than a width of an expansion strut 55 of the second expansion column.

In various embodiments of the stent, the distal section 102 of a connecting strut can include a terminal end 98 conjoined to an expansion strut in the second expansion column. A surface of a connecting strut can be conjoined to an end of an expansion strut in the second expansion column. An edge of a connecting strut can be a linear extension of an edge of an expansion strut in the second expansion column. A strain relief notch can be formed where the edge of the distal section 102 is conjoined with the edge of the expansion strut of the second expansion column. FIG. 5 shows an example of a strain relief notch 120 formed where the edge of the distal section 102 is conjoined with the edge of the expansion strut of the second expansion column. At least one end of a connecting strut can be a direct extension of an expansion strut pair of the first expansion column or the second expansion column. FIG. 5 shows an example of a distal section 102, which is a direct extension of an expansion strut pair that includes an expansion strut 54. FIG. 5 shows an example of a longitudinal axis 117, which is parallel to the longitudinal axis 83 of an expansion strut of the second expansion column. The width of a connecting strut can be less than a width of the expansion strut of the second expansion column. FIG. 5 shows an example of a width of a distal section 103, which is less than a width of an expansion strut 54 of the second expansion column. The length of the distal section of a connecting strut can be greater than a proximal section. FIG. 5 shows an example of a distal section 102 having a length greater than a proximal section 100.

In various embodiments of the stent, the distal section of each second connecting strut can include one or more of: a terminal end conjoined to an expansion strut in the third expansion column, at least one surface conjoined to an end of an expansion strut in the third expansion column, an edge that is a linear extension of an edge of an expansion strut in the third expansion column, a longitudinal axis, a width, and a length. A strain relief notch can be formed where the edge of the distal section is conjoined with the edge of the expansion strut of the third expansion column. FIG. 5 shows an example of a strain relief notch 122 formed where the edge of the distal section is conjoined with the edge of the expansion strut of the third expansion column. The distal section can be a direct extension of an expansion strut pair of the third expansion column. FIG. 5 shows an example of a distal section 105, which is a direct extension of either expansion strut pair including expansion strut 57. The longitudinal axis can be parallel to the longitudinal axis of an expansion strut in the third expansion column. FIG. 5 shows an example of a longitudinal axis 116, which is parallel to the longitudinal axis 85 of an expansion strut of the third expansion column. The width can be less than a width of the expansion strut of the third expansion column. FIG. 5 shows an example of a width of a distal section 105, which is less than a width of an expansion strut 57 of the third expansion column. The length can be greater than a proximal section. FIG. 5 shows an example of a distal section 105 having a length greater than a proximal section 101.

In various embodiments of the stent, the intermediate section 104 of each second connecting strut can be coupled to the proximal and distal sections of a second connecting strut, and the intermediate section 104 have a length greater than a length of the proximal section 100 of a second connecting strut. The longitudinal axis of the intermediate section extends in a vertically diagonal direction relative to a longitudinal axis of the stent and is non-parallel to a longitudinal axis of the stent. At least a portion of the intermediate section is placed in close proximity to an expansion strut pair of the second expansion column. For example, close proximity can be in the range of 0.001 to 0.050 of an inch, in the range of 0.001 to 0.040 of an inch, and/or in the range of 0.001 to 0.030 of an inch.

In various embodiments of the stent, the intermediate section 104 of each first connecting strut in a first connecting column is coupled to the proximal and distal sections of the first connecting strut, and has a length greater than a length of the proximal section of the first connecting strut. The longitudinal axis of the intermediate section extends in a vertically diagonal direction relative to a longitudinal axis of the stent and is non-parallel to a longitudinal axis of the stent. The diagonal direction of the longitudinal axis of the intermediate section of a second connecting strut in a second connecting column extends in an opposing direction of the diagonal direction of the longitudinal axis of the intermediate section of the first connecting strut in a first connecting column. At least a portion of the intermediate section is placed in close proximity to an expansion strut pair of the first expansion column. For example, close proximity can be in the range of 0.001 to 0.050 of an inch, in the range of 0.001 to 0.040 of an inch, and/or in the range of 0.001 to 0.030 of an inch.

In various embodiments of the stent, first connecting struts and second connecting struts can be conjoined to the first and second expansion columns on the ipsilateral or contralateral sides. In various embodiments of the stent, at least a portion of proximal and distal sections of first connecting struts and second connecting struts can have a curvilinear geometric configuration, particularly near a radius of curvature. In various embodiments of the stent, at least a portion of first connecting struts and second connecting struts can have asymmetrical or symmetrical geometric configurations. In various embodiments of the stent, all first connecting struts and all second connecting struts have parallel longitudinal axes.

In some embodiments of the stent, both terminal ends of the first connecting strut are conjoined to an expansion strut in the first expansion column and the second expansion column. Some embodiments of the stent include a plurality of expansion columns coupled by a plurality of connecting strut columns.

Figure 3:
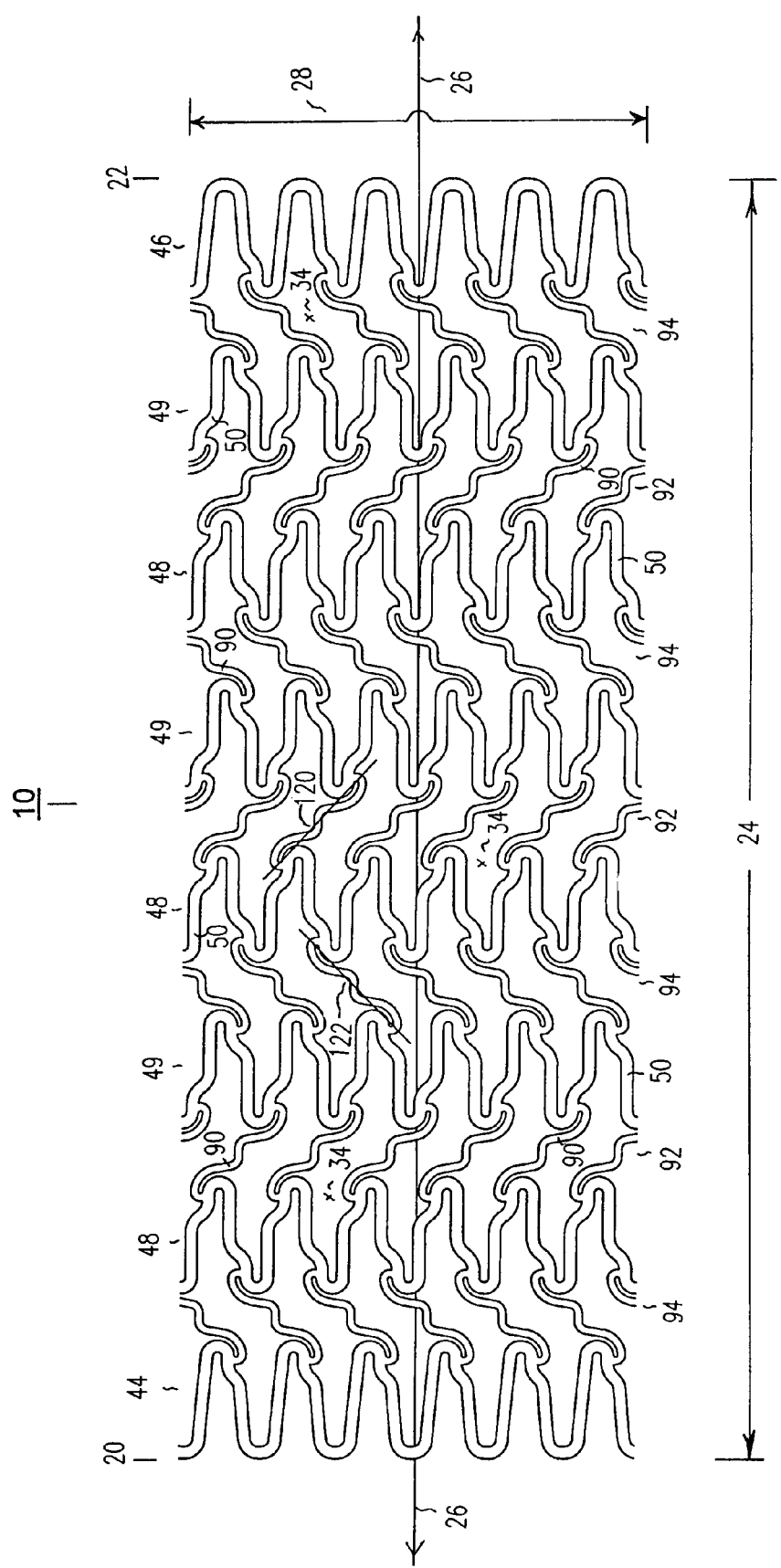
FIG. 3 shows a cut-open view of an embodiment of a stent. Various expansion columns and connecting strut columns are shown.

Some embodiments of the stent include a first end expansion column and a second end expansion column. The first end expansion column and the second end expansion column can define a proximal and a distal end of the stent, and they are mirror images to each other. For example, FIG. 3 shows end expansion columns 44 and 46 as minor images.

Some embodiments of the stent include a plurality of cells. The plurality of cells is defined by the first expansion column, the second expansion column and the first connecting strut column. The cells in the stent have asymmetrical geometry, but the cells also can have symmetrical geometry. The cells have evenly spaced geometry and the cells transform into a quasi-hexagonal geometry in a nominally expanded state. For example, FIGS. 1-5 show cells 34 in a non-expanded form.

An expansion column of the stent has expansion struts in a ring configuration made of zigzag shaped expansion strut pair cycles. Expansion columns are responsible for radial expansion, optimal crimping, and radial strength of the stent. The expansion columns by themselves do not provide flexibility. Each zigzag cycle in an expansion column can have plurality of expansion strut pairs conjoined by a joining strut loop at either a proximal end or a distal end. This sequence continues, for twelve times in one embodiment, seamlessly around the circumference of an expansion column in a stent.

Various embodiments of the stent include one or more of several different types of expansion columns including one or more of several types of expansion struts. An end expansion column at the proximal end can include straight-line expansion struts and stair-step expansion struts with a short stepped-down segment at a distal end. An end expansion column at the distal end can include straight-line expansion struts and stair-step expansion struts with a short stepped-down segment at a proximal end. The end expansion columns can be minor images. Terminating side of end expansion columns can have smooth and evenly rounded loops.

The middle of the stent can include, for example, alternating different types of expansion columns that can be minor images. One expansion column type includes straight-line expansion struts and stair-step expansion struts with a stepped-down segment in the proximal end and a stepped-up segment in the distal end. Another expansion column type includes straight-line expansion struts and stair-step expansion struts with a stepped-up segment in the proximal end and a stepped-down segment in the distal end.

A stepped-down or stepped-up segment can be short in length near a proximal or a distal end of a long straight segment of a stair-step expansion strut and a short sloped transitional segment. A transitional segment of an expansion strut conjoins a connecting strut with an expansion strut, for example, with the long straight segment of the stair-step expansion strut. The connecting strut can be a direct extension of the expansion strut and be integral to the stent structure rather than a separate structure added, welded or attached. Separate terminology for stent elements, for example expansion and connecting struts, conveniently describes the anatomy and function of various stent portions.

A connecting strut in a connecting strut column is not directly conjoined to another connecting strut in the same connecting strut column or in another adjacent connecting strut column.

Proximal and distal ends of a stair-step connecting strut can be a direct extension of an expansion strut pair loop of adjacent expansion columns. A stair-step connecting strut in a connecting strut column can inter-connect two apposed expansion strut pair loops in a vertically offset, diagonal direction. Expansion strut pair loops of two adjacent expansion columns can be arranged in a peak-to-valley apposition.

A stair-step connecting strut in a connecting strut column can have a short segment on an end directly extending from an expansion strut pair of an expansion column and a longer segment on the other end directly extending from an expansion strut pair of an adjacent expansion column. Between these two end segments a connecting strut can include a straight center segment having a slant-angle orientation relative to the two end segments. A center segment can be placed in close proximity of an expansion strut pair loop of one of two adjacent expansion columns, which are conjoined by the connecting strut.

A stair-step connecting strut can have each end conjoined on the ipsilateral sides of apposed expansion strut pair loops of adjacent expansion columns. A longitudinal axis of a stair-step connecting strut can have a diagonal orientation relative to the longitudinal axis of the stent. A diagonally oriented axis of a stair-step connecting strut in one connecting strut column has a first direction, and a diagonally oriented axis of a stair-step connecting strut in an adjacent connecting strut column has a second direction. Longitudinal axes of connecting struts in adjacent connecting strut columns can run in opposing directions.

A connecting strut can have three straight segments, two pivot points with two radii of curvature, and two ends that extend directly from expansion struts of adjacent expansion columns. The pivot points in a connecting strut can serve as flexing points for stent flexibility. Longitudinal axes of horizontally oriented segments of connecting strut can run in a same direction as a longitudinal axis of a stair-step expansion strut. A central segment of a connecting strut may not be parallel with horizontally oriented segments of the connecting strut. A longitudinal axis of a centrally located intermediate segment of a connecting strut can have a diagonal orientation to longitudinal axes of horizontally oriented segments of the connecting strut and to the longitudinal axis of the stent.

A connecting strut column can conjoin adjacent expansion columns forming enclosed stent cells of asymmetrical geometry. Cells can transform into a roughly hexagonal geometry when, for example, the stent is nominally expanded in a 3-dimensional tubular state.

Some embodiments of the stent include a first expansion column, a second expansion column, and a first connecting strut. The first expansion column and the second expansion column can include expansion struts forming a plurality of expansion strut pair loops. Expansion strut pair loops can couple adjacent expansion struts. Two adjacent expansion struts can share a common strut. The first connecting strut column can include a plurality of individual connecting struts.

FIG. 1 shows one embodiment of a stent 10 in side elevation view, with a first expansion column 29, a second expansion column 30, a third expansion column 31, a first connecting strut column 32, and a second connecting strut column 33. The stent 10 has a proximal end 20 and a distal end 22. The stent 10 can have a tubular or cylindrical structure. The stent 10 can have a longitudinal length 24 and a longitudinal axis 26.

In some embodiments of the stent, an expansion column can be a zigzag and/or corrugated ring configuration of expansion struts. An expansion column, for example expansion column 30, in a stent 10 can be an unbroken circular ring. Multiple expansion strut columns can be interconnected with connecting struts continuously along the longitudinal axis 26 of the stent 10 in an unbroken manner to form a stent 10 having a tubular shape. The interconnections among expansion columns and connecting strut columns enclose spaces, or cells, formed by expansion struts and connecting struts. In the embodiment shown in FIG. 1, many cells have asymmetrical geometry. The stent 10 has two different diameters, including an outer diameter 36 and an inner diameter 38, having a difference of a thickness of the stent 10. Both the outer diameter 36 and inner diameter 38 can change as the stent 10 goes through a crimping stage, when the diameters 36 and 38 are narrowed, and through a deployed stage, when the diameters 36 and 38 are expanded.

Figure 2:
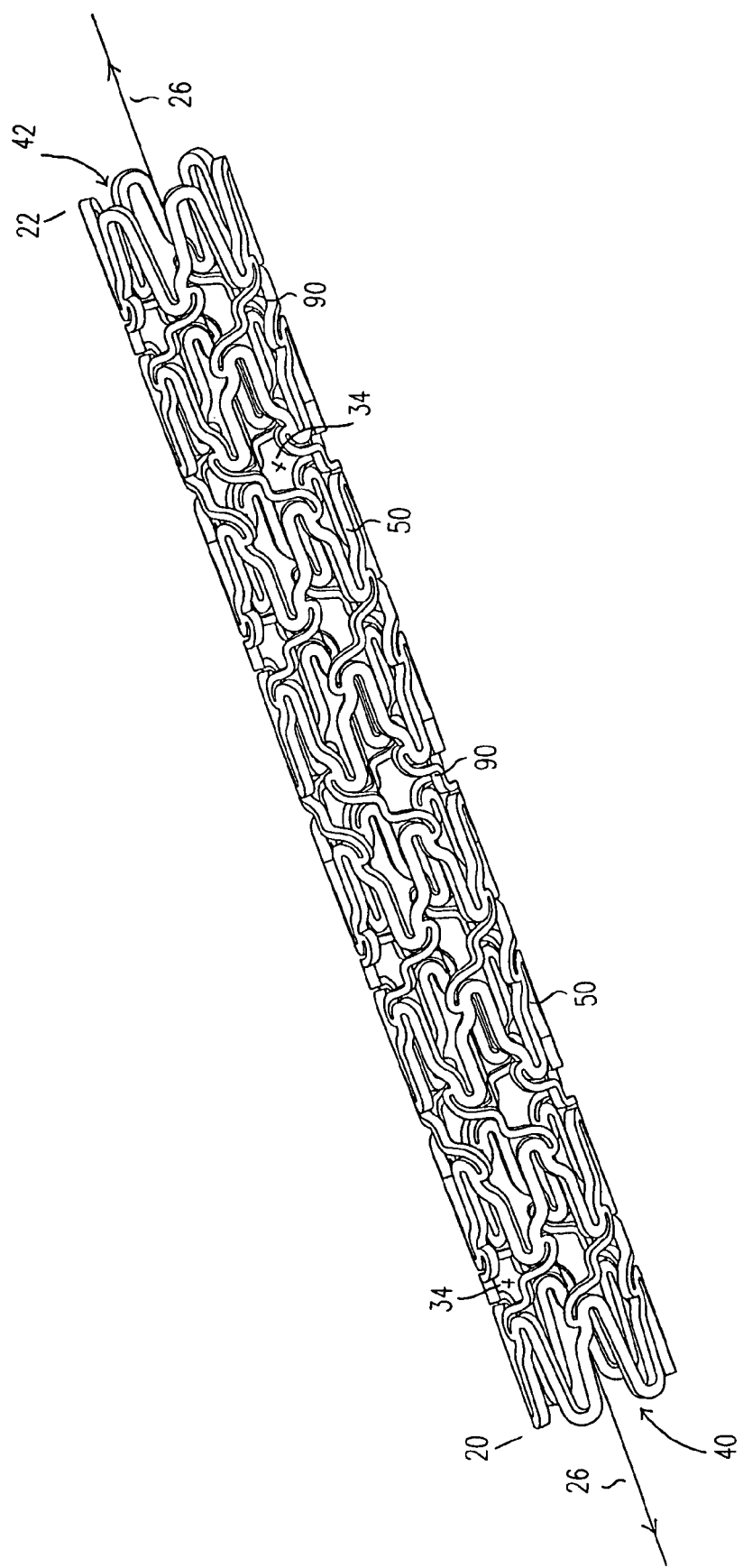
FIG. 2 shows an isometric view of an embodiment of a stent, such as a tubular stent.

FIG. 2 shows one embodiment of a stent 10 in isometric view. A back half of the stent 10 can be seen through the front half of the stent 10. The shown embodiment of the stent 10 has a tubular structure with a central lumen, a proximal opening 40, and a distal opening 42. Stent cells 34 include open spaces in the network of expansion struts and connecting struts. The lumen includes the central, open tunnel formed by the stent.

FIG. 3 shows one embodiment of a stent 10 in cut-open view. The stent 10 has a proximal end 20 and a distal end 22. This view of the stent 10 is a scale drawing for a 15 mm coronary stent. There are eight expansion columns and seven connecting strut columns. At the proximal end 20 is an expansion column 44, which is a mirror image of an expansion columns 46 at the distal end 22. In the middle of the stent 10, there are six expansion columns, such that an expansion column 49 alternates with an expansion column 48. Interconnecting with eight expansion columns along the longitudinal axis 26 of the stent 10 are seven connecting strut columns including four connecting strut columns 94 and three connecting strut columns 92, such that a connecting strut column 94 alternates with a connecting strut column 92. In the middle of the stent 10 are two upright connecting strut columns 132 and three upside down connecting strut columns 134. There are a total of 42 cells of four different asymmetric configurations. All the cells have asymmetrical geometry. Expansion columns 44, 46, 48, and 49 are vertically arranged with expansion strut pair loops aligned peak-to-valley. Connecting strut columns 92 and 94 interconnect expansion columns 44, 46, 48, and 49 in a continuous and unbroken manner along the length 24 and around the circumference 28 of the stent 10.

The stent 10 in FIG. 3 has the proximal end 20 on the left and the distal end 22 on the right. The stent 10 has a length 24 horizontally and a circumference 28 vertically, with a longitudinal axis 26 horizontally along the length 24 from the proximal end 20 to the distal end 22.

A width (horizontal dimension) of expansion columns is wider than a width of connecting strut columns. However, a width of a connecting strut column could be made the same or larger than a width of an expansion column. The variation of width ratio between a connecting strut column and an expansion column are within the scope of present invention of stent 10. The number of expansion strut cycles in an expansion column and the number of connecting struts in a connecting strut column can be made variably different. Variable numbers of making expansion strut cycles and connecting struts are within the scope of the present invention of the stent 10.

FIG. 4 shows a magnified view of a middle section of one embodiment of a stent 10. FIG. 4 shows several expansion columns 48 and 49. Each expansion column can have six cycles of continuous, unbroken expansion strut pair loops with six loops on a proximal end and six loops on a distal end. Each expansion strut pair loop in an expansion column 49 can include a stair step expansion strut 54 with a stepped-down short segment 58 in a distal end and a short stepped-up segment 60 in a proximal end, and a straight expansion strut 52, in a regularly alternating sequence. Each expansion strut pair loop in an expansion column 48 can include a stair step expansion strut with a stepped-down short segment 56 in a proximal end and a short stepped-up segment 62 in a distal end, and a straight expansion strut 52, in a regularly alternating sequence. The embodiment of stent 10 of FIG. 3 includes six stair step expansion struts 54 in an expansion column 48 or 49. Expansion struts 52 and 54 are conjoined by a joining loop 66 in a proximal end or a joining loop 68 in a distal end.

A transitional slope 74 can be between a stepped up proximal segment 60 and a straight segment in a stair step expansion strut 54. Likewise, a transitional slope 76 can be between a stepped up distal segment 62 and a straight segment in a stair step expansion strut 54. A transitional slope 70 can be between a stepped down proximal segment 56 and a straight segment in a stair step expansion strut 54. Likewise, a transitional slope 72 can be between a stepped down distal segment 58 and a straight segment in a stair step expansion strut 54.

In an expansion column 48 or 49, a straight segment of expansion strut 52 can have a longitudinal axis 80. Similarly, a stair step expansion strut 54 can have a longitudinal axis 82. Expansion columns 48 and 49 can be horizontally aligned along the axis of the stent, with proximal peaks 66 of expansion strut pair loops of one expansion column 48 aligned with proximal peaks 66 of expansion strut pair loops of adjacent expansion column 49. Short stepped down segments 56 and 58 of adjacent expansion columns 48 and 49 are aligned on the ipsilateral or same sides. Short stepped up segments 74 and 76 of adjacent expansion columns 48 and 49 are aligned on the ipsilateral or same sides. Similarly, long straight segments of expansion struts 54 in an adjacent expansion column 48 can also be aligned on the ipsilateral sides.

FIG. 5 shows a magnified view of a middle section of one embodiment of a stent 10. A connecting strut has a longitudinal axis 112 or 110. A stair-step connecting strut in a connecting strut column 92 or 94 can have a short segment, for example 100, on an end directly extending from an expansion strut pair of an expansion column and a longer segment, for example 102, on the other end directly extending from an expansion strut pair of an adjacent expansion column. Between these two end segments a connecting strut can include a straight center segment, for example 104, having a slant-angle orientation relative to the two end segments. A central intermediate segment 104 can be placed in close proximity to an expansion strut pair loop of adjacent expansion columns, which can be conjoined by the connecting strut.

A stair-step connecting strut 90 can have each end 96 and 98 conjoined on the ipsilateral sides of apposed expansion strut pair loops of adjacent expansion columns 48 and 49. A longitudinal axis 110 or 112 of a stair-step connecting strut 90 can have a diagonal orientation relative to the longitudinal axis 26 of the stent. A diagonally oriented axis of a stair-step connecting strut 90 in one connecting strut column 92 has a first direction 110. A diagonally oriented axis of a stair-step connecting strut 90 in an adjacent connecting strut column 94 has a second direction 112. Axes 110 and 112 of connecting struts 90 in adjacent connecting strut columns can run in opposing directions.

In some embodiments of the stent, a connecting strut can have three straight segments 100, 102, and 104; two pivot points 106 and 108 with two radii of curvature 106 and 108; and two ends 96 and 98 that extend directly from expansion struts 54 of adjacent expansion columns. The pivot points 106 and 108 can serve as flexing points for stent flexibility. Longitudinal axes, for example 115 and 117. of connecting strut segments can run in a same direction as a longitudinal axis of a stair-step expansion strut. A central intermediate segment 104 of a connecting strut may have an axis, for example 118, not parallel with, for example, other segments of the connecting strut. A longitudinal axis 118 of a central intermediate segment 104 of a connecting strut can have a diagonal orientation to longitudinal axes of other segments of the connecting strut 115 and 117.

In some embodiments of the invention, examples of which are illustrated in FIGS. 6-9 and 13-15, a stent 210 may include first connecting struts which conjoin the first and second expansion columns. Each first connecting strut can have a stair-step geometric configuration. The stair-step configuration of a connecting strut can have first and second intermediate sections, a proximal segment coupled to the first expansion column, and a distal segment conjoined directly to an expansion strut of the second expansion column.

The proximal segment of a first connecting strut can be coupled to an associated expansion strut in the first expansion column.

The distal segment of a first connecting strut can be directly extended from an associated expansion strut in the second expansion column.

At least one of a proximal end and a distal end of a first connecting strut can be a direct extension of an expansion strut pair of the first and second expansion columns.

At least one of a proximal end and a distal end of a first connecting strut in the first expansion column can be coupled to an ipsilateral side of an expansion strut pair of the first and second expansion columns, and at a vertical-slant angle to a side of an expansion strut pair of one of the first and second expansion columns.

A longitudinal axis of the distal segment that forms the extension of the associated expansion strut in the second column and a longitudinal axis of the associated expansion strut in the second expansion column are within 20 degrees of each other. The proximal segment of each first connecting strut in the first connecting strut column can be ipsilaterally coupled to an expansion strut pair of the first expansion column and its corresponding distal segment can be ipsilaterally extended from an expansion strut pair of the second expansion column.

A proximal end and a distal end of a first connecting strut in the first connecting strut column can be conjoined on an ipsilateral side of expansion strut pairs of the first and second expansion columns.

Each first connecting strut can have a proximal end that is conjoined to the first expansion column in a first direction, and a distal end that is conjoined to the second expansion column in a second direction that is different from the first direction.

Each first connecting strut has three points of pivot. Each point of pivot can have at least one radius of curvature.

At least a portion of the second intermediate section of a first connecting strut in the first connecting strut column can be positioned in close proximity to a proximal end of an expansion strut pair in the second expansion column. At least a portion of the first intermediate section of a first connecting strut in the first connecting strut column can be in close proximity to a distal end of an expansion strut pair in the first expansion column. Close proximity can be in the range of 0.001 to 0.050 of an inch.

Each first connecting strut can have a longitudinal axis that is non-parallel to a longitudinal axis of the stent. The longitudinal axis of each first connecting strut can extend in a first direction that is positioned diagonally relative to the longitudinal axis of the stent. Each first connecting strut can have the same longitudinal axis. All of the first connecting struts in a first connecting strut column can have parallel longitudinal axes. At least a portion of the first connecting struts has asymmetrical geometric configurations.

One expansion strut of an expansion strut pair of the first expansion column can have a stair-step segment at a proximal end. The other expansion strut of the expansion strut pair can have a stair-step segment at a distal end. One expansion strut of an expansion strut pair of the second expansion column can have a stair-step segment at a distal end. The other expansion strut of the expansion strut pair can have a stair-step segment at a proximal end.

The first and second intermediate sections of each first connecting strut can be coupled with at least a first radius of curvature. Distal ends of expansion strut pairs of the first expansion column that are coupled to proximal ends of expansion strut pairs of the second expansion column can be vertically offset.

The stent embodiments include a plurality of expansion columns conjoined by a plurality of connecting strut columns.

A plurality of cells is defined by the first expansion column, the second expansion column and the first connecting strut column. The stent cells can have asymmetrical geometries and a quasi-hexagonal geometry in a nominally expanded state.

The second connecting strut column can include a plurality of individual second connecting struts that couple the second and third expansion columns. Each second connecting strut can have a stair-step geometric configuration. The geometric configuration can have first and second intermediate sections, a proximal segment coupled to the first expansion column, and a distal segment conjoined directly to an expansion strut of the second expansion column.

Each second connecting strut can have a longitudinal axis that is non-parallel to a longitudinal axis of the stent. The longitudinal axis of each second connecting strut can extend in a second direction that is positioned diagonally relative to the longitudinal axis of the stent. Each second connecting strut can have the same longitudinal axis. All of the second connecting struts can have parallel longitudinal axes. Each first connecting strut of the first connecting strut column can have a longitudinal axis that extends in a first direction that is opposite to the second direction of the longitudinal axis of the second connecting struts.

Expansion strut pair loops of the first and second expansion columns or second and third expansion columns can be aligned in a peak-to-valley geometry, a valley-to-peak geometry, or a peak-to-peak geometry.

In some embodiments an expansion column includes six cycles of zigzag form made of twelve expansion strut pairs. Each expansion strut pair includes two expansion struts conjoined by a looped joining section at either a proximal or a distal end. This form of pairing of two expansion struts conjoined by a looped joining section alternates between proximal to distal and distal to proximal, continuing twelve times seamlessly around the circumference of an expansion columns in a cylindrically shaped stent. In some embodiments there can be various expansion struts of different types making up twelve blind-loop expansion strut pairs in an expansion column of a cylindrical stent. In order to have twelve blind-loop expansion strut pairs in an expansion column, there also are twelve looped joining sections, half located in proximal ends and half located in distal ends, in an alternating sequence.

Figure 8:
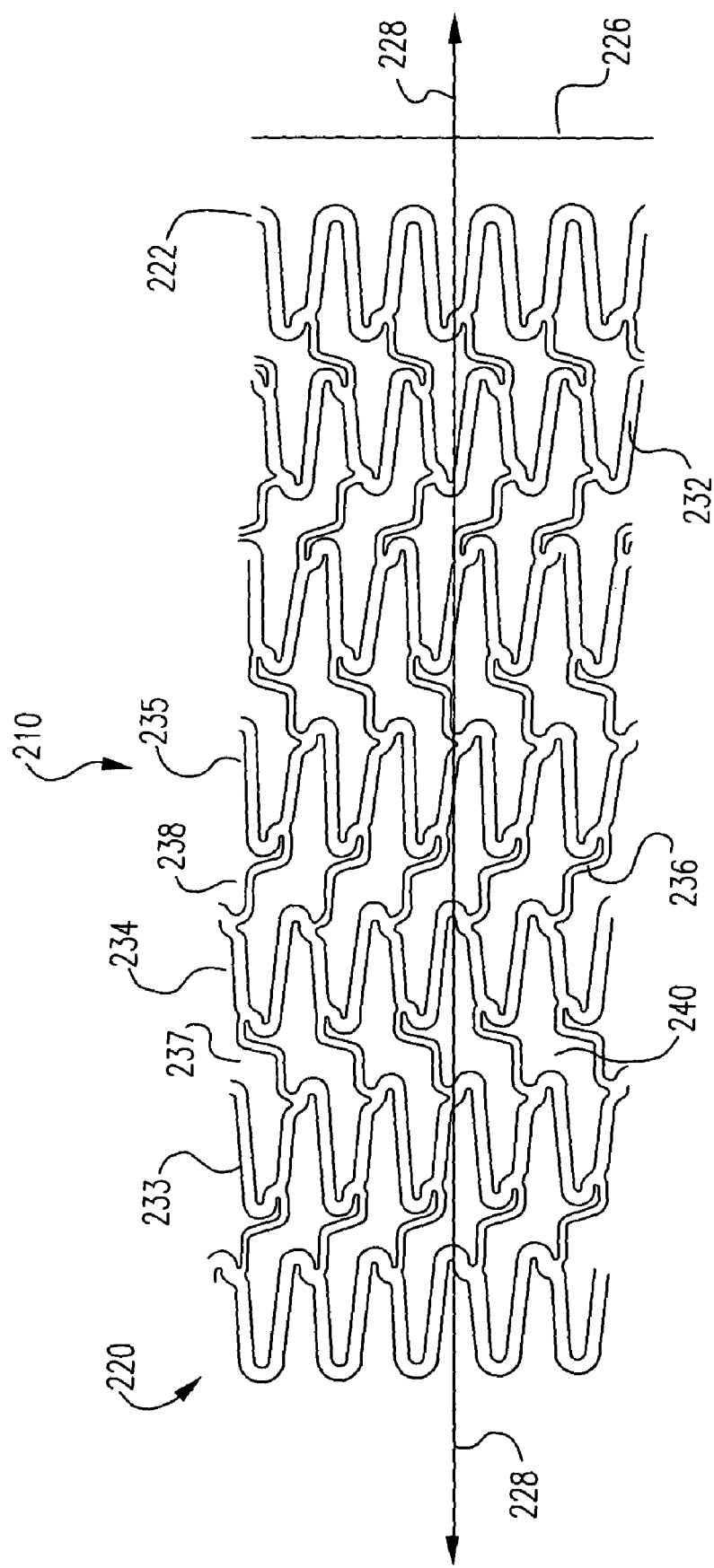
FIG. 8 shows a cut-open view of an embodiment of a stent. Various expansion columns and connecting strut columns are shown.

There are various forms of expansion column in a stent, some as depicted in FIG. 8. Some embodiments include expansion strut columns with pairs of different expansion struts. Some possible expansion struts include a straight expansion strut shape, a straight part with a short step-down segment at a proximal end and a straight part with short step-up segment at a distal end, a straight part with a short step-up segment at a proximal end and a straight part with short step-down segment at a distal end. Other combinations include a longer straight part with a short step-down segment at a proximal end, a longer straight part with a short step-down segment at a distal end, a longer straight part with a short step-up segment at a proximal end, and a longer straight part with a short step-up segment at a distal end. At each step-up or step-down segment, an expansion strut can have a short-sloped transitional section between the long and short parts. Various combinations are within the scope of the invention. On both proximal and distal ends of a stent embodiment in FIG. 8, a terminating side of an end expansion column can have smooth and evenly rounded loops.

A step-up or step-down segment can be short in length near a proximal or a distal end and can have a short sloped transitional section. A sloped transitional section can provide flexibility, crimping space, and smooth surface modulation effects to the stent performance. One end of a connecting strut can directly conjoin with the long part of an expansion strut at a sloped transitional section of an expansion strut. Another end of a connecting strut can be conjoined to the side of a short step-up or step-down section. One end of a connecting strut can be a direct extension of an expansion strut on the ipsilateral side. The other end can be laterally conjoined on the ipsilateral side of a step short segment of an expansion strut. A connecting strut is an integral part of the stent structure, rather than a separate structure added, welded or attached. Terminology such as expansion strut or connecting strut conveniently describes the structural anatomy and function of various stent portions.

A connecting strut column, including each connecting strut, has stair-step configurations, for example as shown in FIGS. 9, 12A & 12B, 13, 14 and 15. Due to the stair-step configuration, a longitudinal axis of a connecting strut has a diagonal direction to the vertical or horizontal plane of the stent. A connecting strut of the stent can have, in some embodiments, two horizontal sections, two slanted vertical sections, and three pivot points. The horizontal end of a connecting strut can extend from sloped transitional sections of an expansion strut pair loop. The slanted vertical end can conjoin to an ipsilateral side of an apposed expansion strut pair loop at the step down or step-up segment. A stair-step connecting strut can link an expansion strut pair loop of one expansion column to an expansion strut pair loop of an adjacent expansion column in a vertically split-level linking pathway. Each end of a connecting strut can conjoin on the ipsilateral sides of apposing expansion strut pair loops.

A connecting strut that conjoins on ipsilateral sides of expansion strut pair loops, and a split-level linking pathway with multiple pivot points provides stent flexibility, conformability and excellent crimping characteristics to a stent. When each end of a connecting strut is conjoined to a looped pair of expansion struts, the ratio of expansion strut to connecting strut number can be two to one.

When the expansion columns and connecting strut columns are conjoined, the stent can have a continuous, unbroken cylindrical form without breaks or de-linking around the circumference and along the length of a stent. The unbroken link between the expansion and connecting struts can form regular and even asymmetrical cells. The cell size can be maximized or minimized, by programming the dimensions of expansion struts and connecting struts of the stent, as dictated by the clinical or application requirements.

Figure 6:
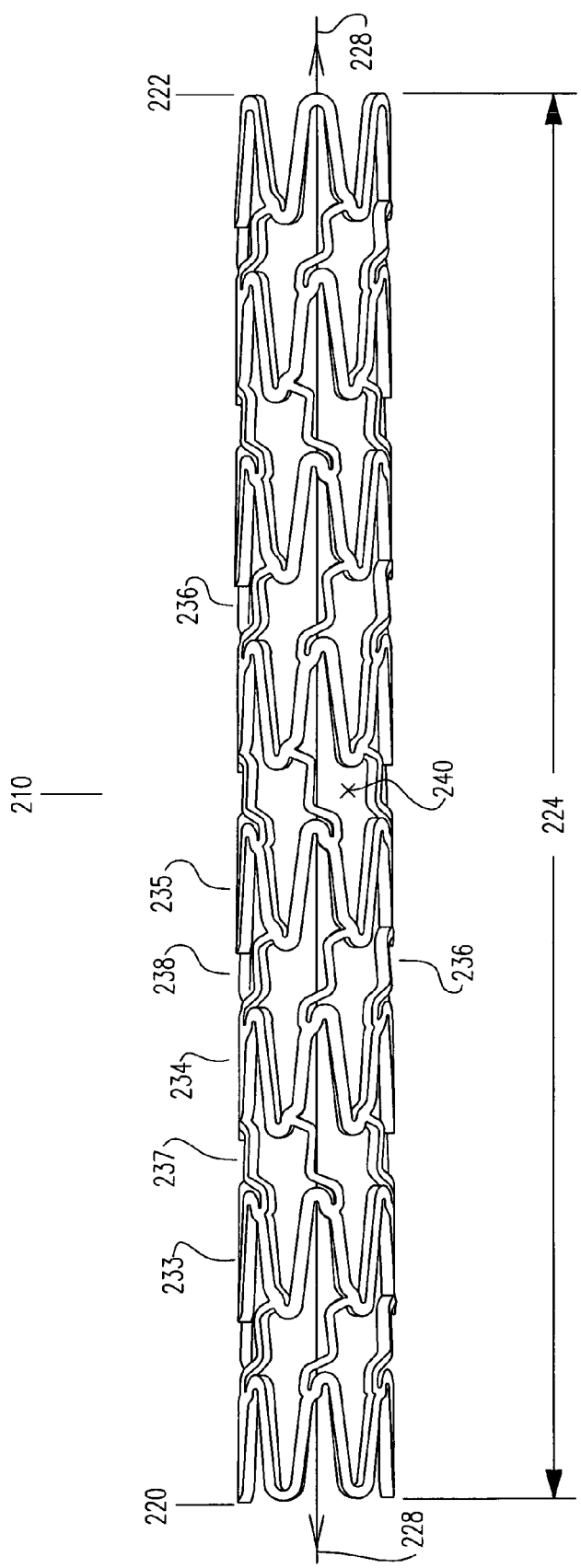
FIG. 6 shows a side elevation view of an embodiment of a stent, such as a tubular stent.

FIG. 6 shows one embodiment of a stent 210 in side elevation view. The stent 210 has a proximal end 220 and a distal end 222. The stent 210 can have a tubular or cylindrical structure. The stent 210 can have a longitudinal length 224 and a longitudinal axis 226. Defined by linked connecting and expansion struts are open empty spaces, or cells, for example a cell 240. At both the proximal end 220 and distal end 222 of the stent 210 the terminal ends of expansion strut pairs are evenly rounded for smooth and uniform crimping when the stent 210 is mounted on a delivery balloon.

Figure 7:
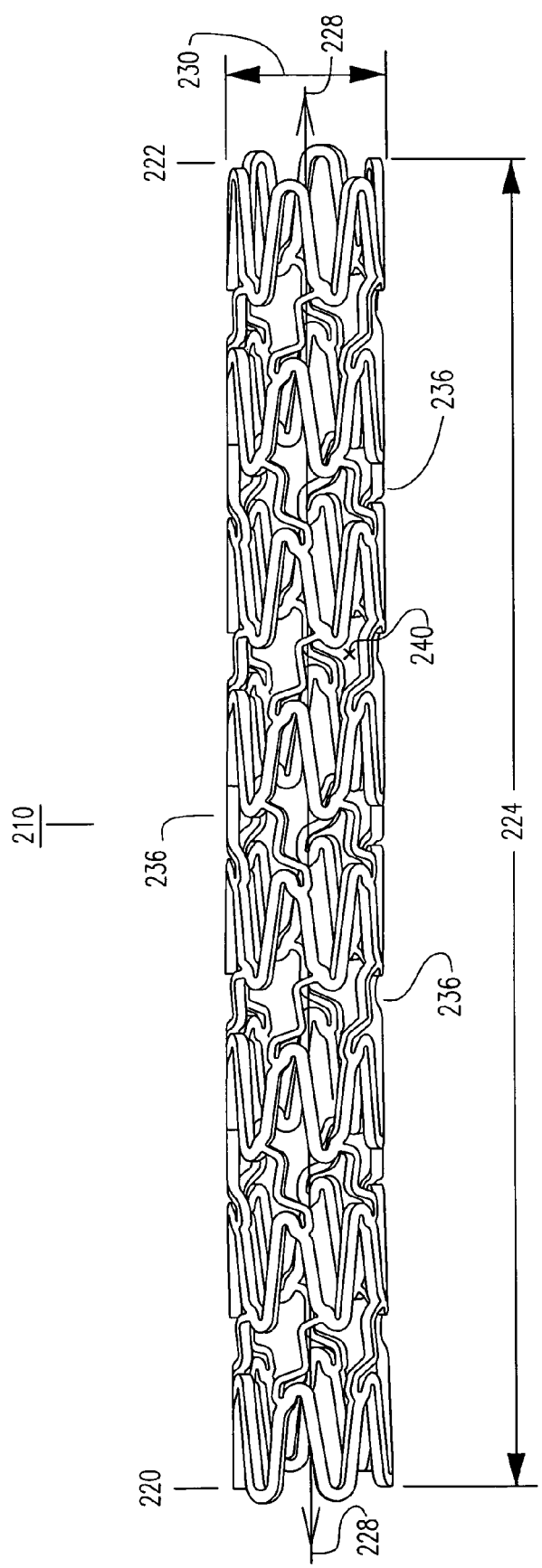
FIG. 7 shows an isometric view of an embodiment of a stent, such as a tubular stent.

FIG. 7 shows an isometric view of an embodiment of a stent, such as a tubular stent. The proximal end 220, distal end 222, the longitudinal axis 226, an internal diameter 230, and a longitudinal length dimension 224 of the cylindrical shape of the stent 210 are shown. The back half of the stent 210 can be seen through cells, such as cell 240.

FIG. 8 shows a cut-open 2-dimensional view of the cylindrical stent 210. The stent 210 has a longitudinal axis 228, and a circumferential dimension 226. The stent 210 has expansion columns, such as expansion columns 233, 234, and 235; and connecting strut columns, such as connecting strut columns 237 and 238. Expansion column and connecting strut columns alternate in sequence along the longitudinal axis 228 of the stent.

In some embodiment, the expansion columns include a same number of zigzag cycles. Expansion columns shown in FIG. 8 have five zigzag cycles. Other embodiments can have more than five cycles, or less than five cycles. In an embodiment with five cycles in expansion columns, there are ten expansion struts. Each cycle includes a pair expansion struts.

Connecting strut columns have stair-step shaped connecting struts, for example connecting strut 236. For every one pair of expansion struts, there is a connecting strut, making for a ratio of expansion struts to connecting struts of two to one.

Figure 9:
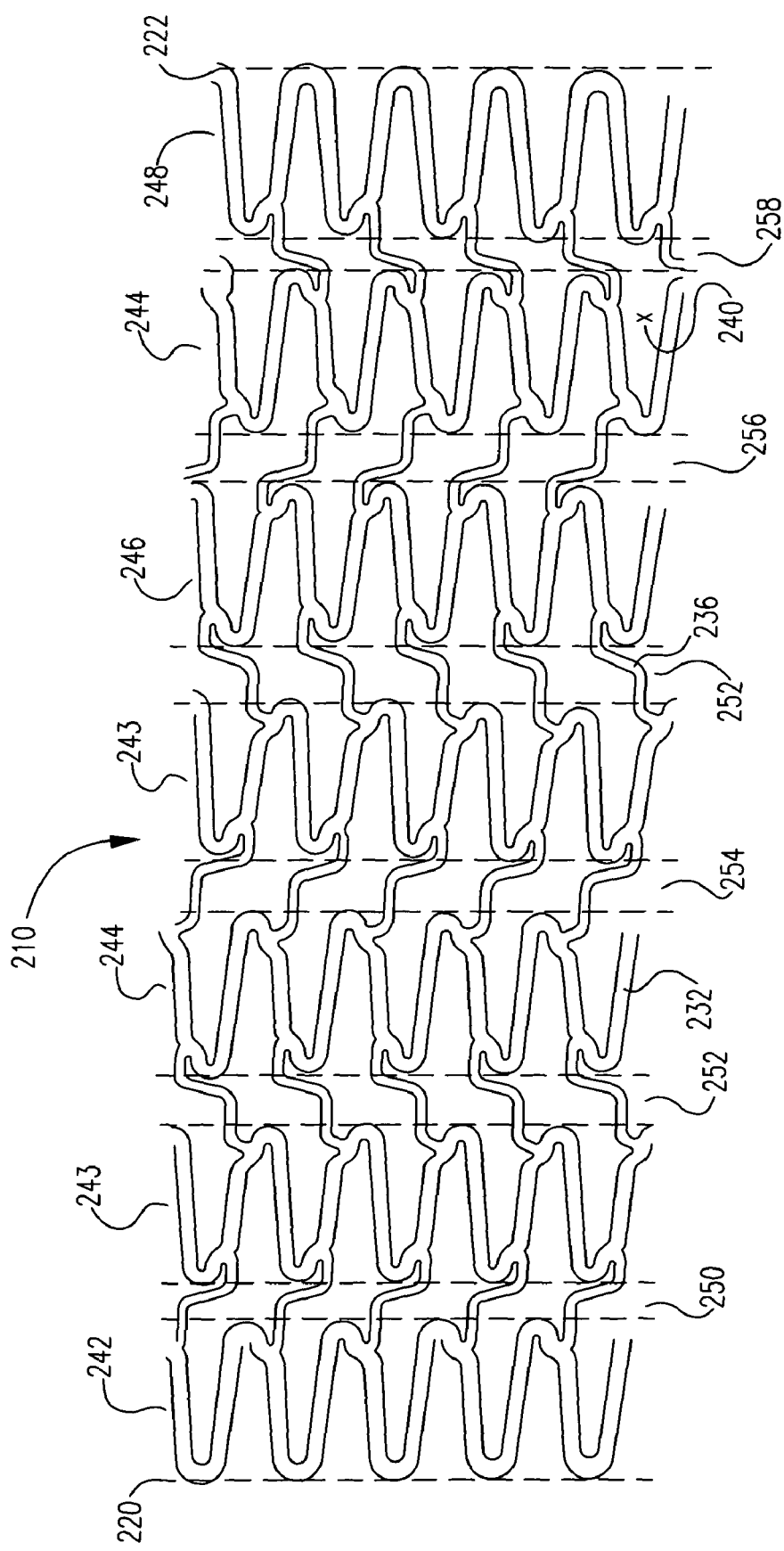
FIG. 9 shows another cut-open view of an embodiment of a stent. Various expansion columns and connecting strut columns are shown.

FIG. 9 shows expansion columns and connecting strut columns. The embodiment of FIG. 9 includes a proximal end expansion column 242, a distal end expansion column 248, and expansion columns 243, 244, and 246. In a proximal end expansion column 242, the terminating end loops are rounded in shape making for a smooth surface at the proximal end of the stent 210, suitable for crimping on a delivery balloon. Proximal end expansion column 242 includes an expansion strut type having a straight shape and another expansion strut type having a step-up stair step segment with a sloped-transitional section. These two expansion strut types can make up an expansion strut pair. The distal end expansion strut column 248 can substantially be a mirror image of the proximal end expansion strut column 242. The distal end expansion strut column 248 positions evenly spaced and rounded loops at the terminating end of the stent 210. Evenly spaced and rounded ends can give a smooth surface alignment when the stent 210 is crimped on a delivery balloon.

Expansion column 243 includes different types of expansion strut. One type has a straight strut and the other has a step-up segment at the proximal end and a step-down segment at a distal end. An expansion strut of each type can form an expansion strut pair loop conjoined by a joining strut section, either in the proximal end or the distal end. This pairing can continue around the circumference of the stent 210 in an uninterrupted fashion.

Expansion column 244 includes an expansion strut having a straight shape and another expansion strut with a step-down segment at the proximal end and step-up segment at the distal end. These two types of expansion strut alternate, forming expansion strut pair loops in a continuous manner around the circumference of the cylindrical structure of the stent 210.

Expansion column 246 includes an expansion strut having a step-down segment in the proximal end and an expansion strut having a step-down segment in the distal end. These expansion strut types alternate, forming expansion strut pair loops, in a continuous manner around the circumference.

FIG. 9 also shows multiple connecting strut column arrangements. The scope of the invention includes permutations of the expansion column and connecting strut column configurations.

Figure 10A:
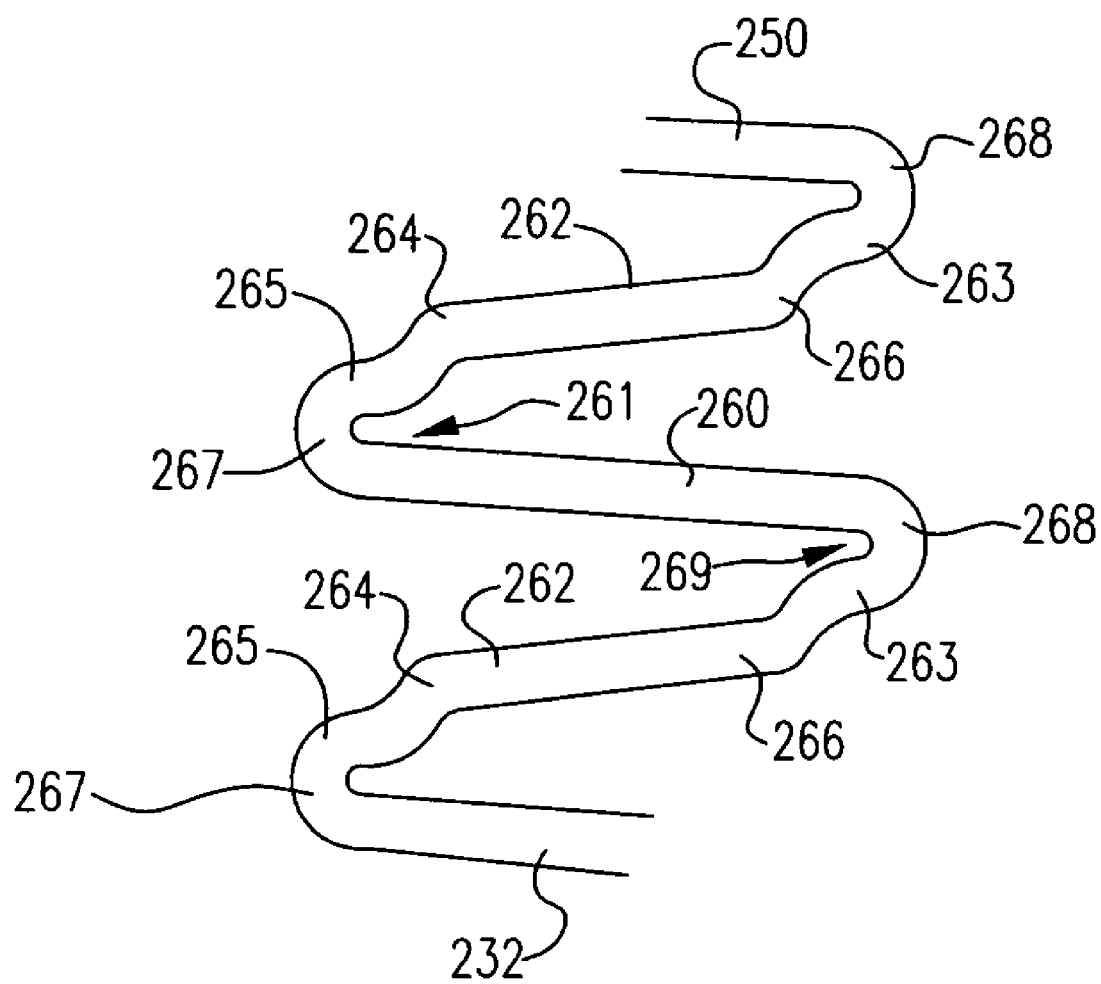
FIGS. 10A and 10B show views of expansion struts.

FIG. 10A shows expansion struts from expansion column 244. Expansion struts 260 alternate with expansion struts 262, joined either by proximal joining section 267 or distal joining section 268. Proximal joining section 267 defines a proximal cul-de-sac 261. Distal joining section 268 defines a distal cul-de-sac 269. A proximal end of expansion strut 262 includes a step down segment 265 joined by sloped transitional segment 264 to the center of expansion strut 262. A distal end of expansion strut 262 includes a step up segment 263 joined by sloped transitional segment 266 to the center of expansion strut 262.

Figure 10B:
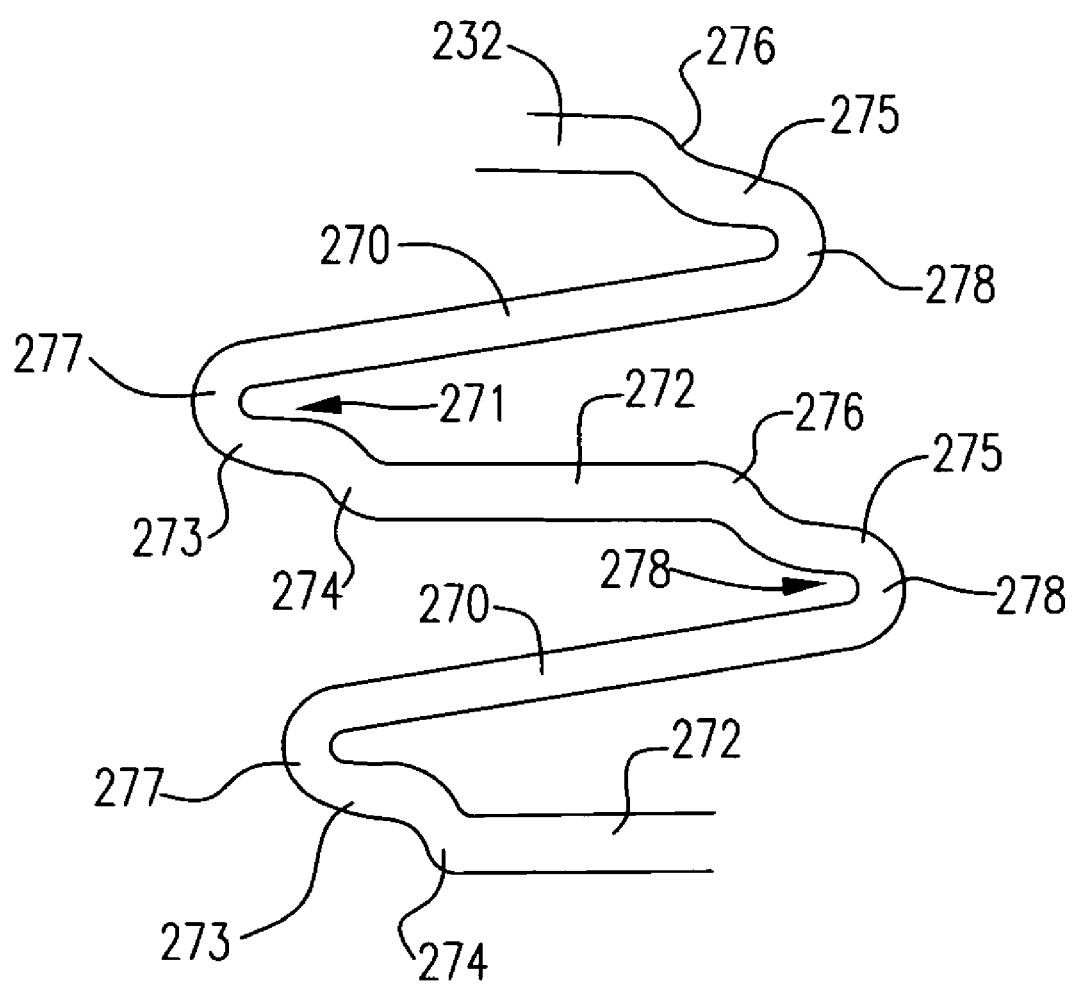

FIG. 10B shows expansion struts from expansion column 243. Expansion struts 270 alternate with expansion struts 272, joined either by proximal joining section 277 or distal joining section 278. Proximal joining section 277 defines a proximal cul-de-sac 271. Distal joining section 278 defines a distal cul-de-sac 279. A proximal end of expansion strut 272 includes a step up segment 273 joined by sloped transitional segment 274 to the center of expansion strut 272. A distal end of expansion strut 272 includes a step up segment 275 joined by sloped transitional segment 276 to the center of expansion strut 272.

Together, FIGS. 10A and 10B show the valleys of expansion column 244 aligned with the peaks of expansion column 243.

Figure 11A:
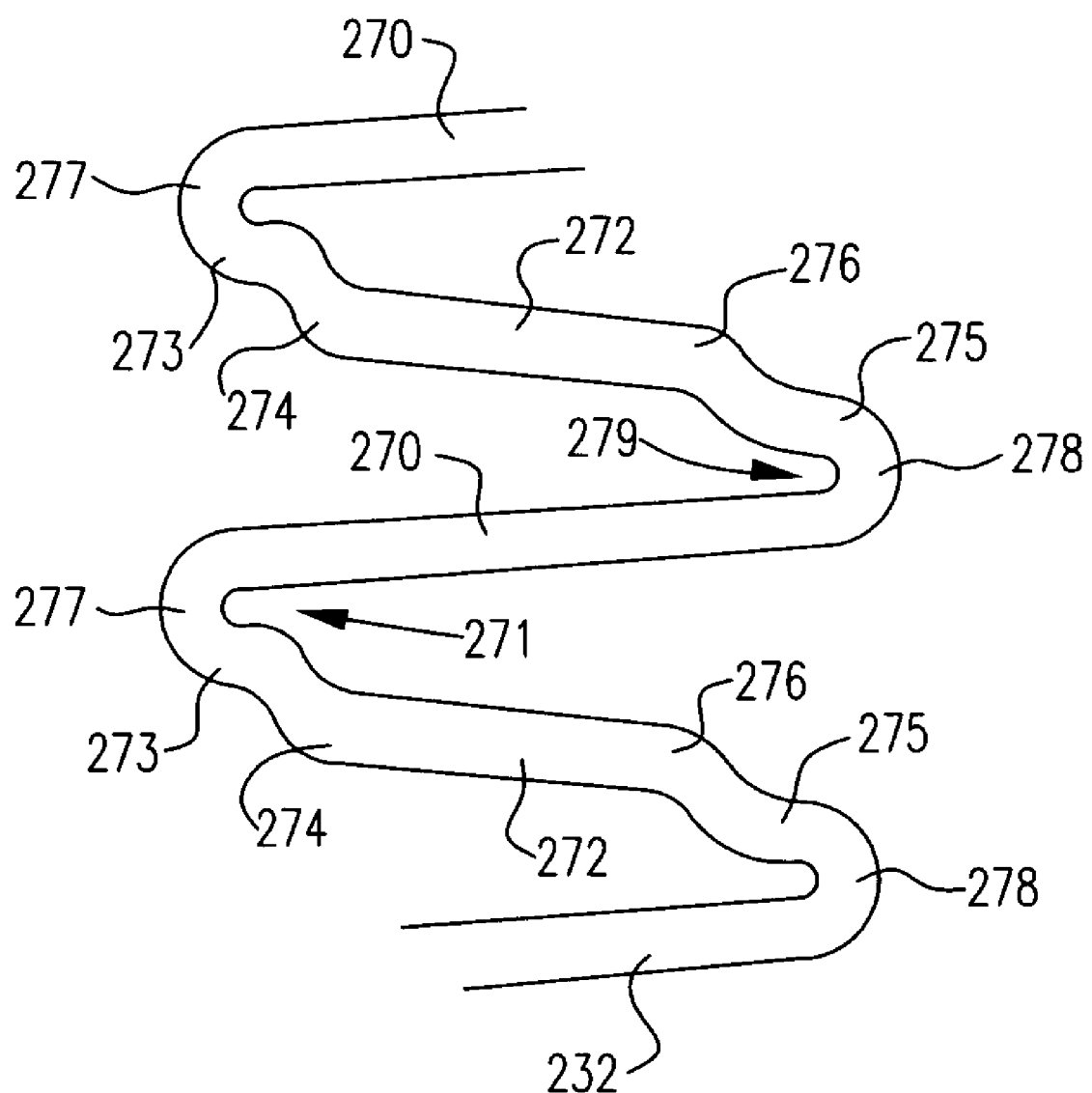
FIGS. 11A and 11B show more views of expansion struts.
Figure 11B:
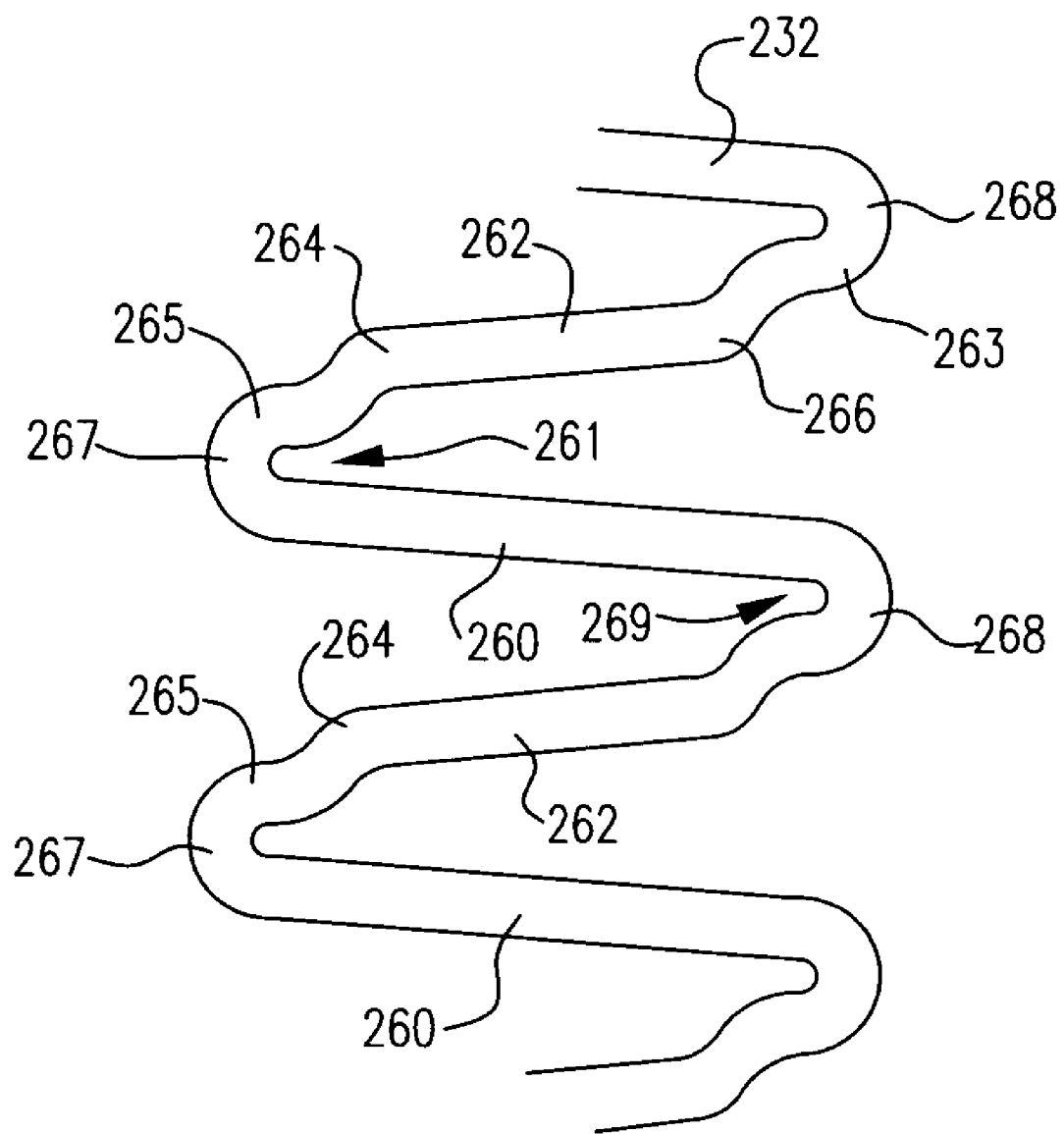

FIG. 11A also shows expansion struts of an expansion column 243. FIG. 11B also shows expansion struts of an expansion column 244. Together, FIGS. 11A and 11B shows the valleys of expansion column 243 aligned with the peaks of expansion column 244.

Figure 12A:
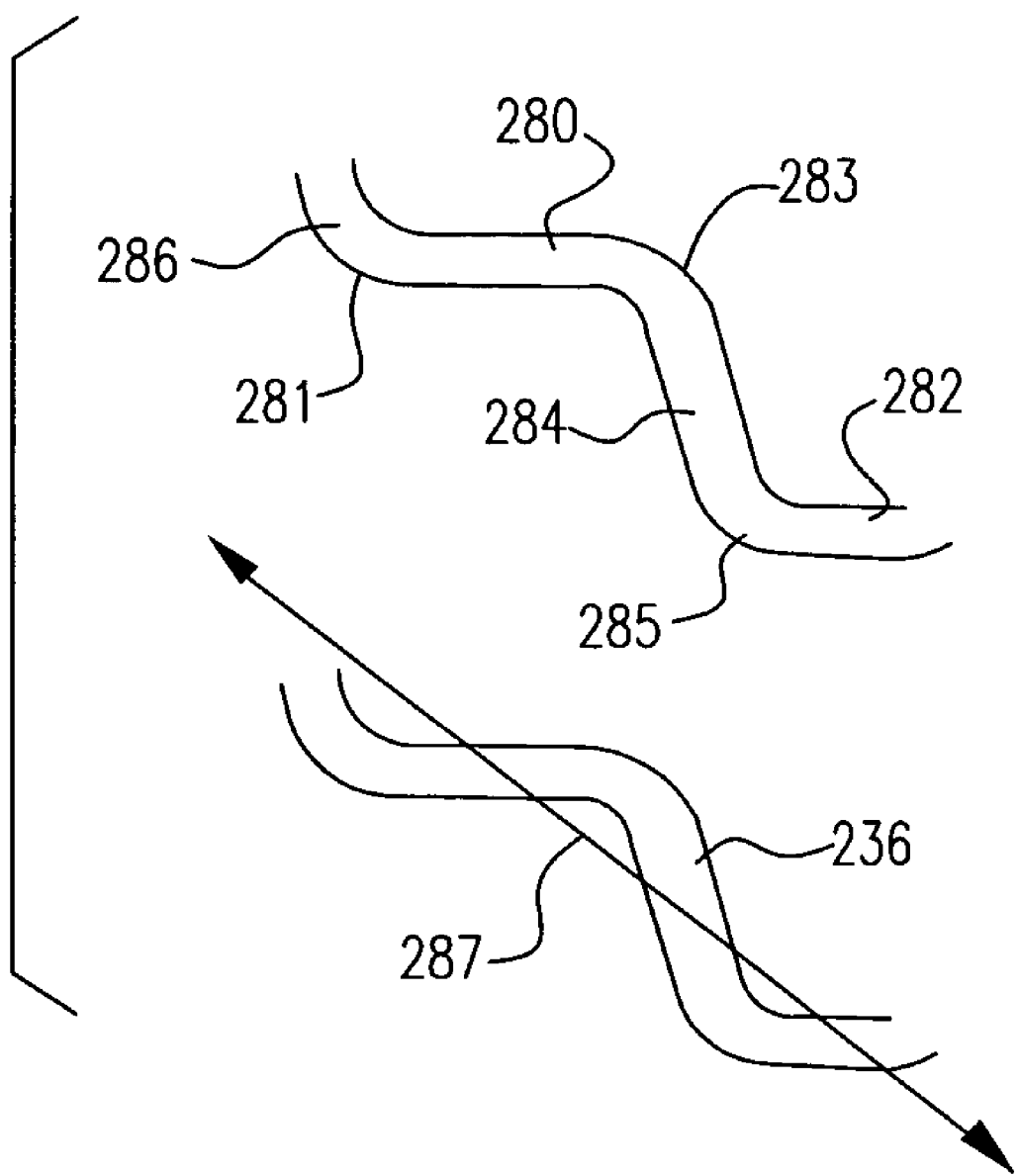
FIGS. 12A and 12B shows views of connecting struts.

FIG. 12A shows connecting struts from connecting strut column 254. A proximal end includes short vertical sloped section 286. Pivot point 281 joins short vertical sloped section 286 with long horizontal section 280. Pivot point 283 joins long horizontal section 280 with long vertical sloped section 284. Pivot point 285 joins long vertical sloped section 284 with short horizontal section 282. Connecting struts in connecting strut column 254 share a longitudinal axis 287.

Figure 12B:
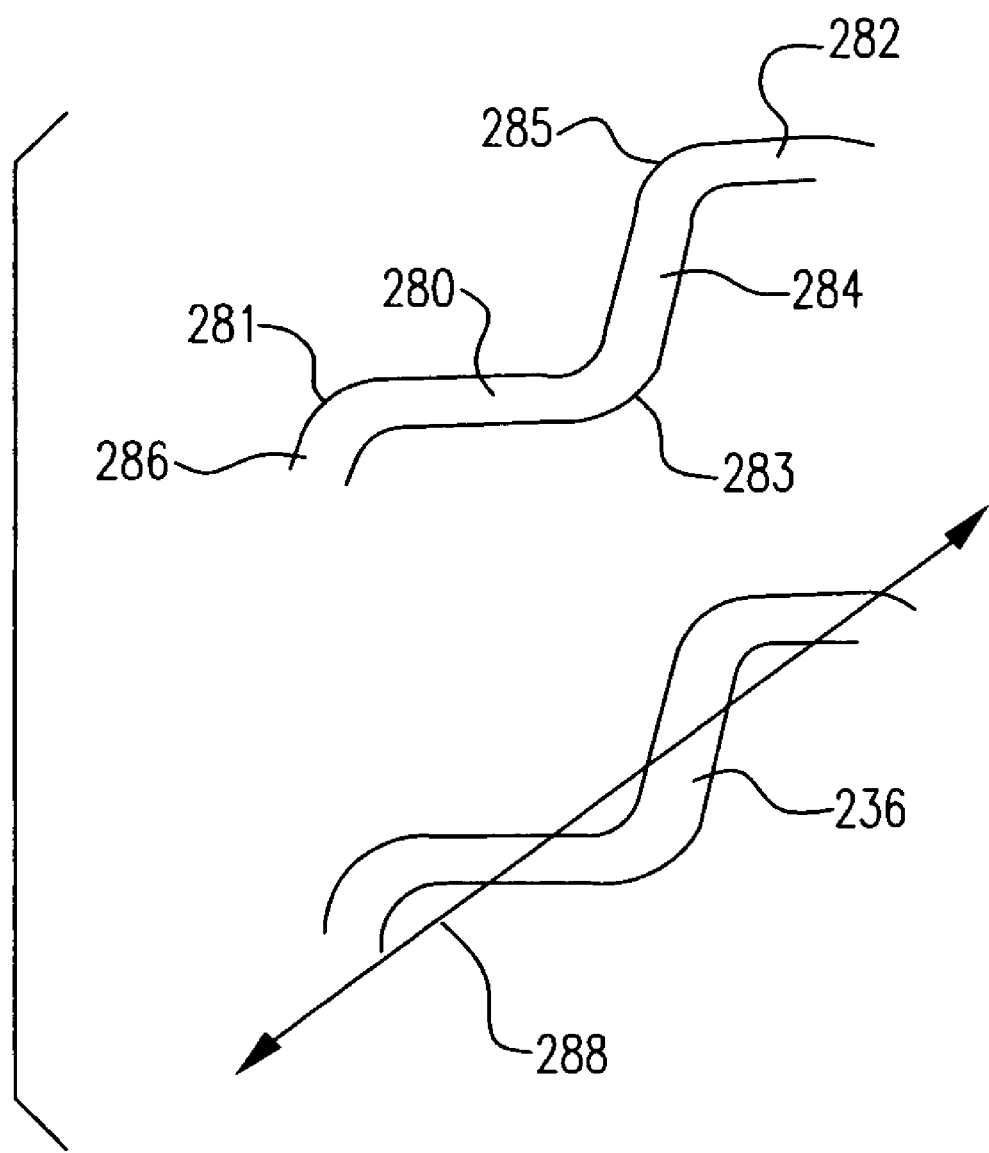

FIG. 12B shows connecting struts from connecting strut column 252, including parts similar to connecting struts from connecting strut column 254. Connecting struts in connecting strut column 252 share a same longitudinal axis 288. The longitudinal axes 287 and 288 are not parallel to each other. Their axes are directed in opposite directions. FIG. 12B is a mirror image of FIG. 12A.

Figure 13:
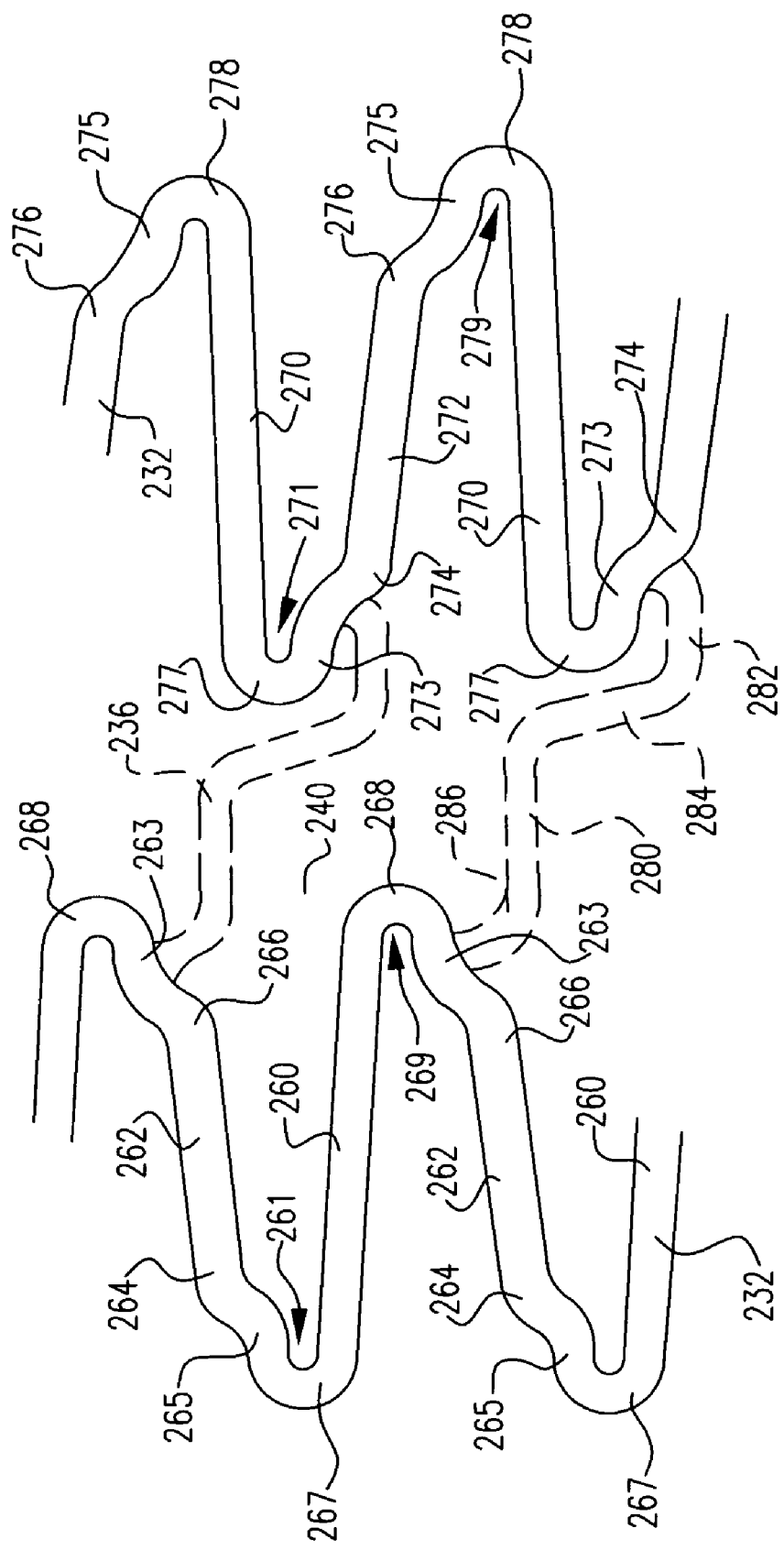
FIG. 13 shows a view of conjoining of connecting struts and expansion struts.

FIG. 13 shows the potential conjoining of connecting strut column 254 with expansion strut column 244 on the proximal side of connecting strut column 254 and expansion strut column 243 on the distal side of connecting strut column 254. The step up segment 263 of expansion strut 262 is conjoined to the proximal side of connecting strut column 254. The step up segment 273 of expansion strut 272 is ipsilaterally conjoined to the distal side of connecting strut column 254. The structure of connecting strut column 254 is outlined in dotted lines.

Figure 14:
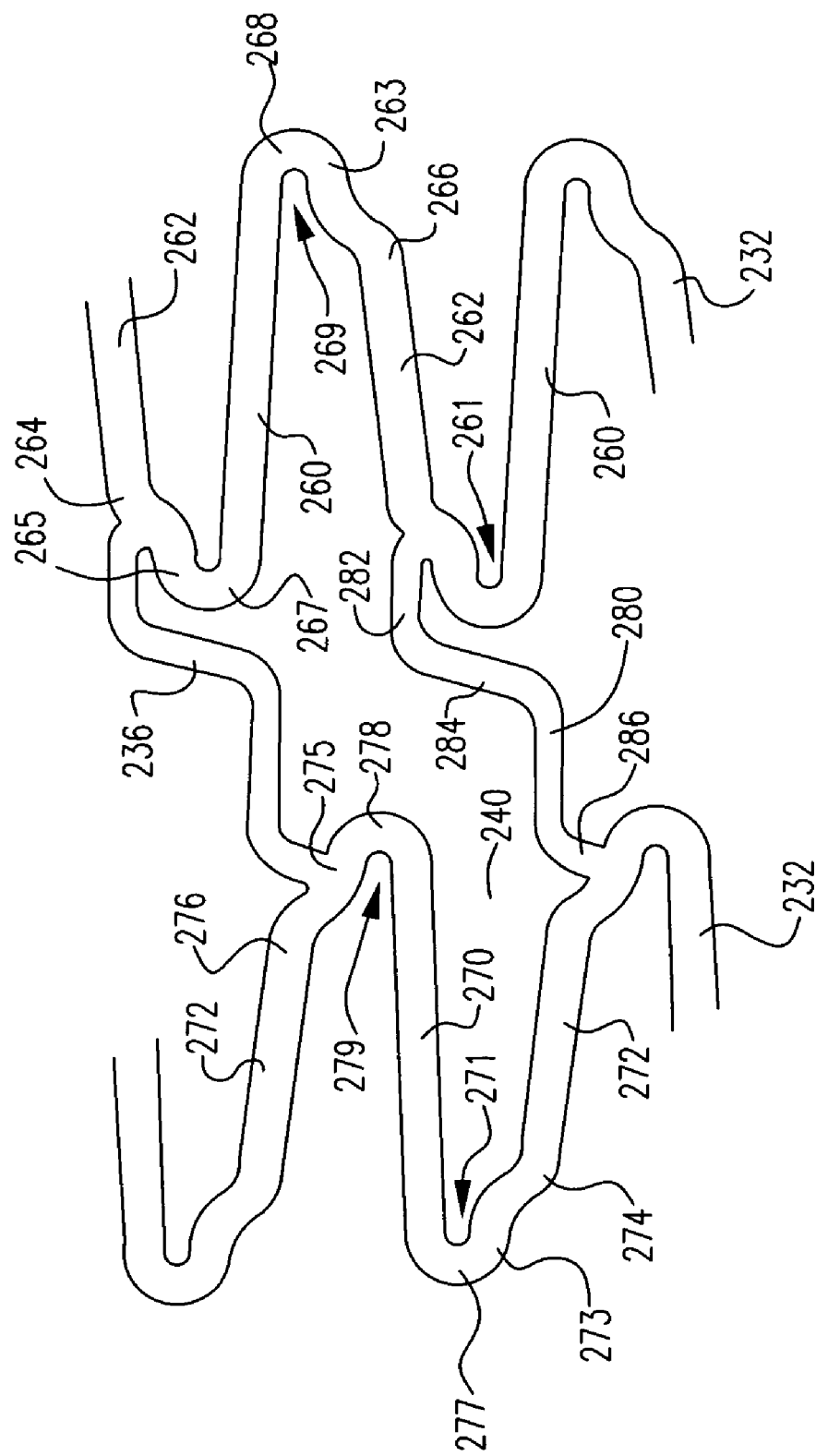
FIG. 14 shows another view of conjoined connecting struts and expansion struts.

FIG. 14 shows the conjoining of connecting strut column 252 with expansion strut column 243 on the proximal side of connecting strut column 252 and expansion strut column 244 on the distal side of connecting strut column 252. The step down segment 275 of expansion strut 272 is conjoined to the proximal side of connecting strut column 252. The step down segment 265 of expansion strut 262 is conjoined to the distal side of connecting strut column 252.

The proximal end 286 of the connecting strut column 252 conjoins on the ipsilateral side to the stepped-down segment 275 of an expansion strut 272. The distal end 282 of a connecting strut column 275 is a direct extension of an expansion strut 262 on the ipsilateral side.

Figure 15:
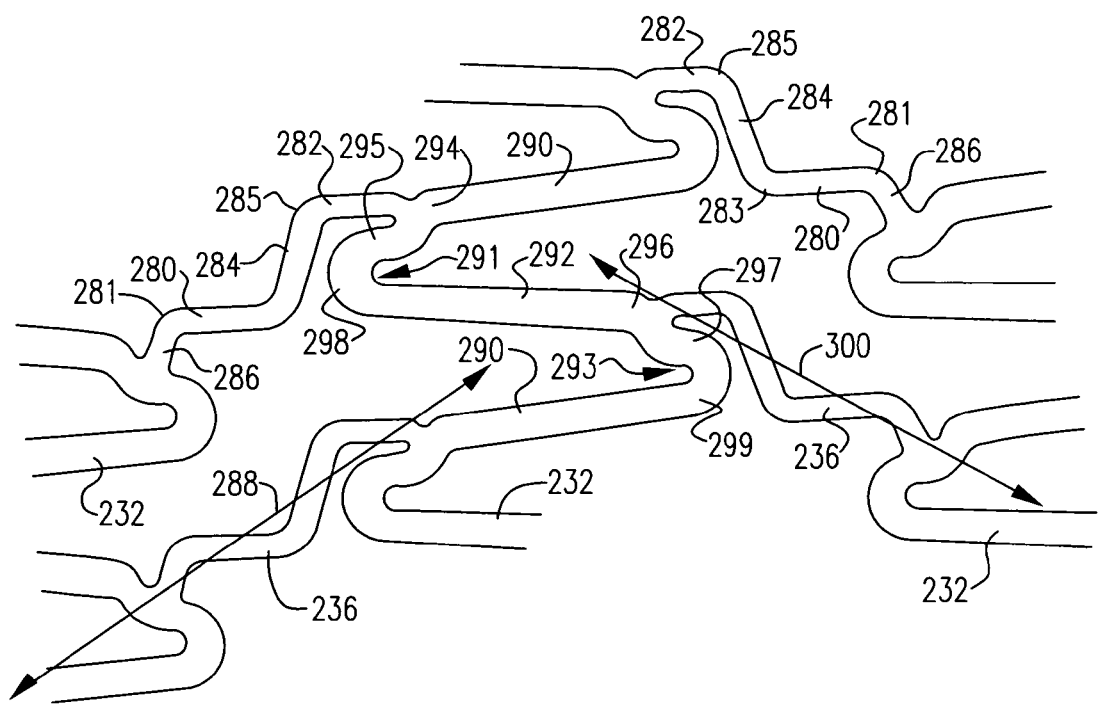
FIG. 15 shows another view of conjoined connecting struts and expansion struts.

FIG. 15 shows the conjoining of expansion column 246 with connecting strut columns 252 and 254. Connecting strut column 252 is conjoined to the proximal side of expansion column 246, and connecting strut column 254 is conjoined to the distal side of expansion strut column 246.

The expansion column 246 shows an important variation of how the connecting struts are conjoined on both proximal and distal ends of the expansion strut pair loops in the expansion strut column 246. Both the proximal expansion strut loops and distal expansion strut loops have direct extensions to the horizontal segment 282 in opposing directions.

In some embodiment of the invention the first expansion column, the second expansion column, and/or the third expansion column of a stent 410, such as is shown in FIGS. 16-20B can include individual expansion struts forming a plurality of expansion strut pairs. FIG. 19B shows examples of individual expansion struts 450 and expansion strut pairs 451. In some embodiments of the stent, one expansion strut of an expansion strut pair can have a stair-step segment at a proximal end and the other expansion strut of the expansion strut pair can have a stair-step segment at a distal end. FIG. 19B shows examples of one expansion strut 453 of an expansion strut pair 451 having a stair-step segment at a proximal end and the other expansion strut 455 of the expansion strut pair 451 having a stair-step segment at a distal end. In some embodiments of the stent, two adjacent expansion strut pairs share a common strut.

Figure 16:
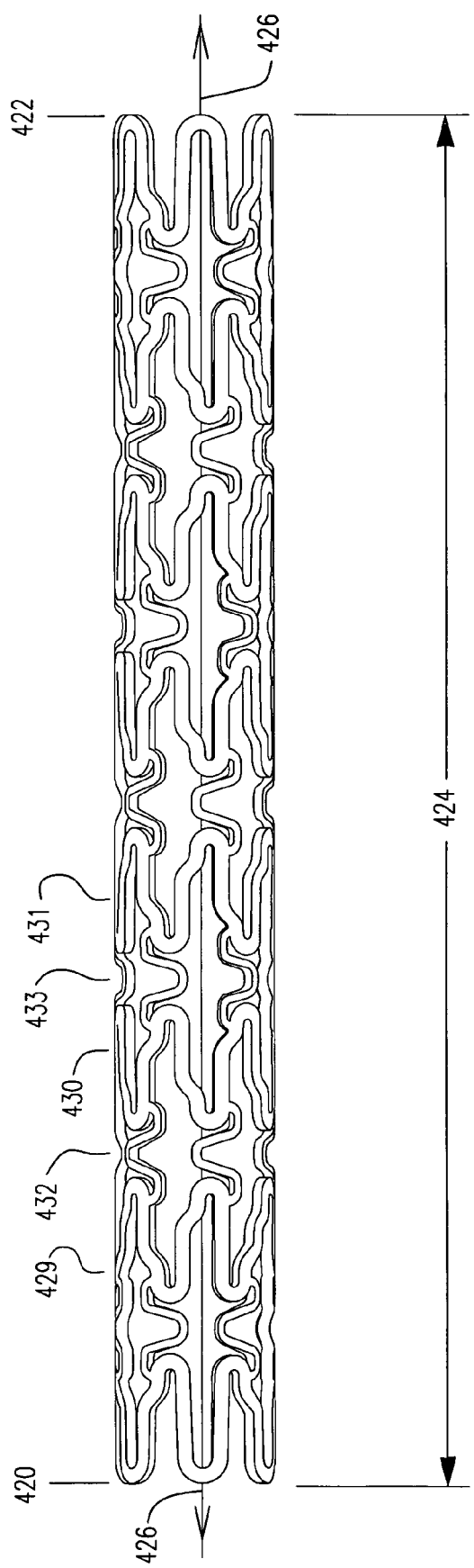
FIG. 16 shows a side elevation view of an embodiment of a stent, such as a tubular stent.
Figure 17:
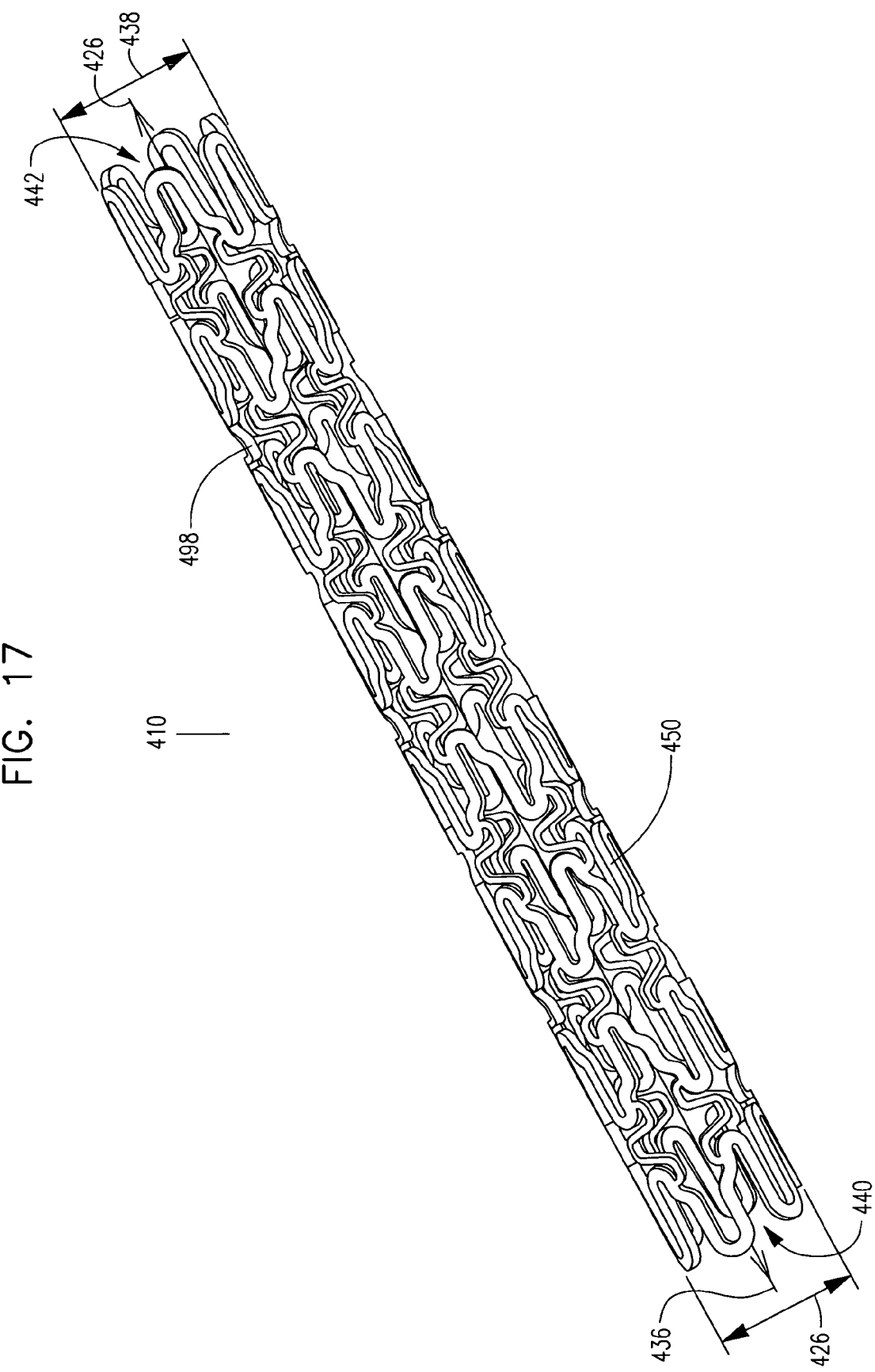
FIG. 17 shows an isometric view of an embodiment of a stent, such as a tubular stent.
Figure 19A:
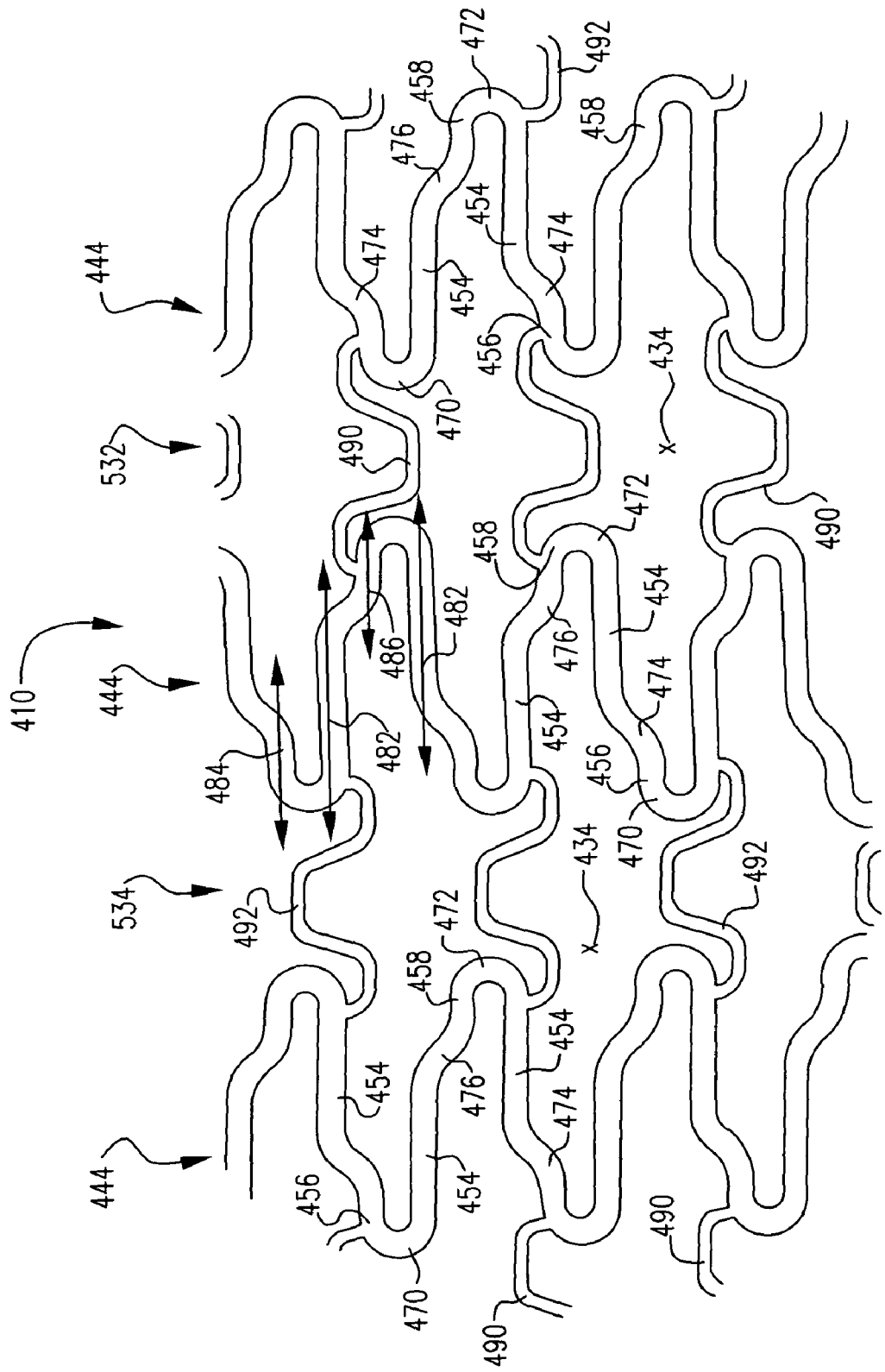
FIG. 19A shows a magnified view of a middle section of an embodiment of a stent, such as a stent of FIGS. 16, 17, and/or 18. Some details are shown of expansion columns.

The first connecting column and/or the second connecting column can include a plurality of individual connecting struts. The plurality of individual connecting struts for at least the first connecting column can couple the first and second expansion columns. In various embodiments of the stent, each connecting strut includes one or more of: at least some number of pivot points, at least some number of sections, bilateral short stems, a geometrical configuration, at least some number of radii of curvature, a center section, and a longitudinal axis. For example, each connecting strut can include at least six pivot points; at least four, five, six, or seven sections; and/or at least three, four, five, or six radii of curvature. FIG. 19B shows examples 514, 516, 518, 520, 522, and 524 of pivot points each having some radius of curvature. Bilateral short stems can be ipsilaterally conjoined to an expansion strut of the first expansion column and to an expansion strut of the second expansion column. FIG. 19B shows examples of bilateral stems 500 and 502 on proximal and distal ends respectively of a connecting strut. Exemplary geometrical configurations include a symmetrical one and/or a quasi M-frame one. FIG. 19A shows examples of connecting struts 490 and 492 which have both a symmetrical geometrical configuration and a quasi M-frame geometrical configuration. The longitudinal axis can be non-perpendicular to a longitudinal axis of the stent, substantially perpendicular to a longitudinal axis of the stent, and/or substantially parallel to a longitudinal axis of the stent. FIGS. 16, 17, and 18 show examples of a longitudinal axis 426 of a stent 410. Examples of longitudinal axes of connecting struts are shown in FIG. 19B as axes 494 and 496. Other examples of axes are in FIG. 19A shown as axes 482, 484, and 486 and in FIG. 20A as axes 480, 482, 488, and 489.

In some embodiments of the stent, each connecting strut can be invaginated and/or inverted into a connector space between expansion strut pairs between the first and second expansion columns. FIG. 19A shows examples of connecting struts 490 and 492 which are invaginated and inverted into the connector space between expansion strut pairs.

In some embodiments of the stent, each connecting strut can be ipsilaterally coupled to an expansion strut of the first expansion column and to an expansion strut of the second expansion column. FIG. 19A shows examples of connecting struts 490 and 492 which are ipsilaterally coupled between expansion struts of different expansion columns.

In various embodiments of the stent, at least one connecting strut has a geometric configuration, such as an asymmetrical geometric configuration and/or a quasi M-frame geometric configuration.

Figure 20A:
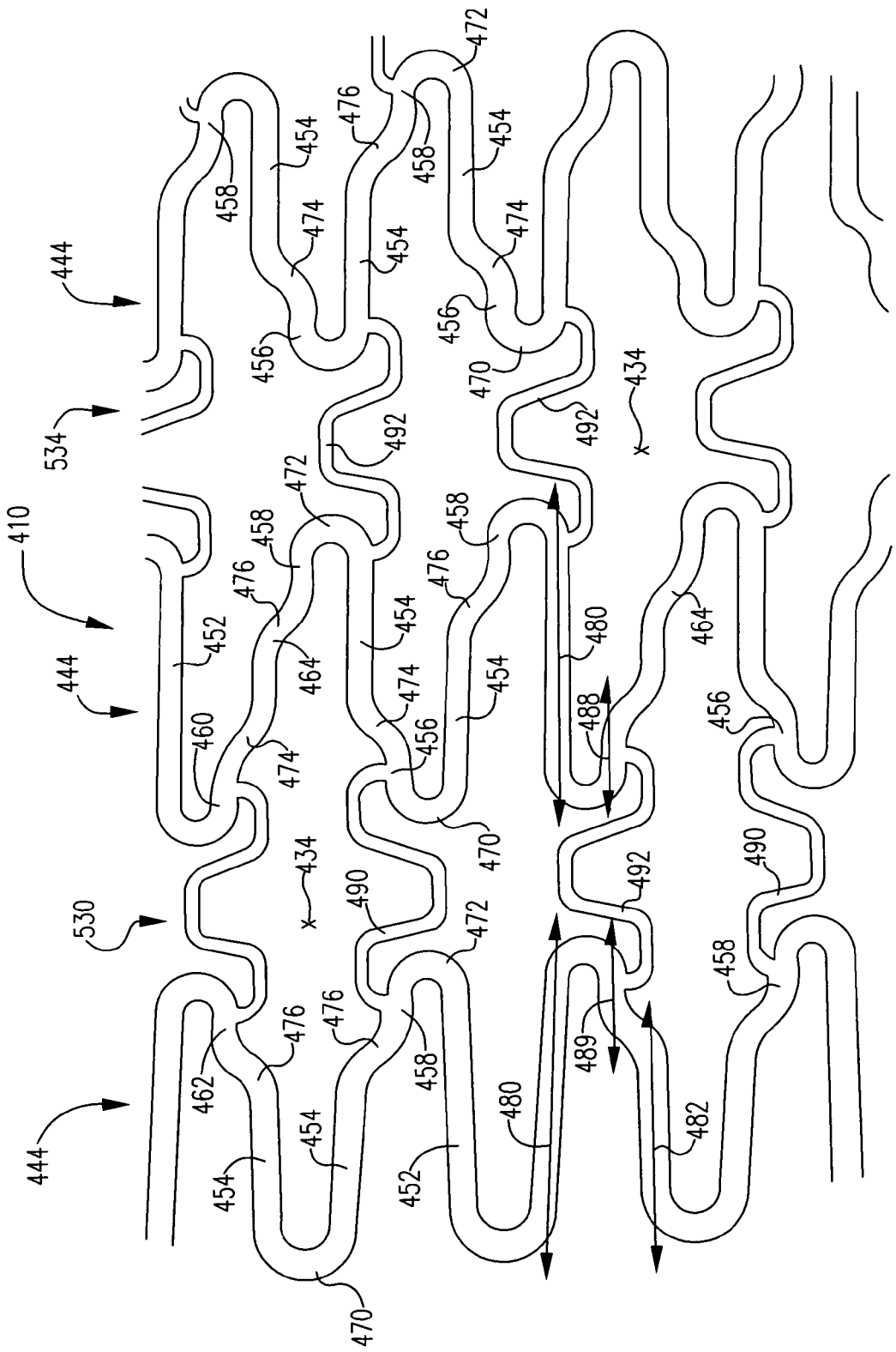
FIG. 20A shows a magnified view of an end section of one embodiment of a stent, such as a stent of FIGS. 16, 17, and/or 18. Some details are shown of an end expansion column.

In some embodiments of the stent the center section can have a substantially truncated conical configuration. In some embodiments of the stent all center sections of the connecting struts extend in a first direction. In some embodiments of the stent the center section of at least a portion of the connecting struts extend in a first direction and/or extend in a second direction. FIGS. 20A and 20B show examples of a connecting strut column 530 having center sections that extend in a first direction, and a connecting strut column 534 having center sections that extend in a first direction and a second direction.

In some embodiments, substantially every longitudinal axis of a connecting strut in a connecting column is parallel to the longitudinal axis of the connecting struts in that column. Each connecting strut can have, for example, at least six pivot points.

Some embodiments of the stent include a first end expansion column and a second end expansion column. The first end expansion column and the second end expansion column can define a proximal and a distal end of the stent. The first end expansion column and the second end expansion column can be mirror images of each other.

Some embodiments of the stent include a plurality of cells. Cells can have asymmetrical geometries ad/or symmetrical geometries. Some geometric shapes have a semi-hexagonal geometry in a nominally expanded state, such as within operating parameters. Cells can be defined by the first expansion column, the second expansion column, and the first connecting strut column. Cells can be defined by the second expansion column, the third expansion column and the second connecting strut column. Cells can have evenly spaced geometric shapes.

Some embodiments of stents can include one or more of a first expansion column, a second expansion column, and a first connecting strut column.

The first expansion column and/or the second expansion column can include individual stair-step expansion struts forming a plurality of expansion strut pair loops. In some embodiments of the stent, expansion strut pair loops couple adjacent individual expansion struts. In some embodiments of the stent, two adjacent expansion strut pair loops share a common stair-step expansion strut.

The first connecting strut column can include a plurality of individual symmetrical geometry connecting struts. The plurality of individual symmetrical geometry connecting struts for at least the first connecting column can couple the first and second expansion columns. In various embodiments of the stent, each symmetrical geometry connecting strut includes one or more of: at least some number of pivot points, at least some number of sections, bilateral short stems, a geometrical configuration, at least some number of radii of curvature, a center section, and a longitudinal axis. For example, each symmetrical geometry connecting strut can include at least six pivot points; at least four, five, six, or seven sections; and/or at least three, four, five, or six radii of curvature. Bilateral short stems can be ipsilaterally conjoined to an expansion strut of the first expansion column and to an expansion strut of the second expansion column. Exemplary geometrical configurations include a symmetrical one and/or a quasi M-frame one. The longitudinal axis can be non-perpendicular to a longitudinal axis of the stent, substantially perpendicular to a longitudinal axis of the stent, and/or substantially parallel to a longitudinal axis of the stent.

In some embodiments of the stent, each symmetrical geometry connecting strut can be invaginated and/or inserted into a connector space between expansion strut pair loops between the first and second expansion columns.

In some embodiments of the stent, each symmetrical geometry connecting strut can be ipsilaterally coupled to an expansion strut of the first expansion column and to an expansion strut of the second expansion column.

In various embodiments of the stent, at least one symmetrical geometry connecting strut has a geometric configuration, such as an asymmetrical geometric configuration and/or a quasi M-frame geometric configuration.

In some embodiments of the stent the center section can have a substantially truncated conical configuration. In some embodiments of the stent all center sections of the symmetrical geometry connecting struts extend in a first direction. In some embodiments of the stent the center section of at least a portion of the symmetrical geometry connecting struts extend in a first direction and/or extend in a second direction.

Some embodiments of the stent include a plurality of expansion columns. The plurality of expansion columns can be coupled by a plurality of connecting strut columns. Each symmetrical geometry connecting strut can have a longitudinal axis. In some embodiments of the stent, substantially every longitudinal axis of a symmetrical geometry connecting strut in a connecting column is parallel to the longitudinal axis of the symmetrical geometry connecting struts in that column. Each symmetrical geometry connecting strut can have, for example, at least six pivot points.

Some embodiments of the stent include a first end expansion column and a second end expansion column. The first end expansion column and the second end expansion column can define a proximal and a distal end of the stent. The first end expansion column and the second end expansion column can be mirror images of each other.

In some embodiments of the stent, individual expansion struts of the first and second expansion column can form a plurality of expansion strut pair loops that couple adjacent individual expansion strut pair loops. In some embodiments of the stent, adjacent individual expansion strut pair loops can be coupled in a symmetrical geometry.

In some embodiments of the stent, expansion strut pair loops of the first and second expansion columns can be aligned. For example, the alignment can be in a peak-to-valley geometry, in a valley-to-peak geometry, and/or in a peak-to-peak geometry.

Expansion struts can include zigzag cycles in a ring shape to form an expansion ring otherwise known as an expansion column. These expansion columns are largely responsible for optimal crimping, even and smooth expanding, and radial strength. Expansion columns by themselves may not be flexible. Each zigzag cycle in an expansion column can have a pair of expansion struts. Two expansion struts can be conjoined, for example, by a joining loop section at a proximal or a distal end. Such pairing, including conjoining at an alternating proximal to distal and distal to proximal sequence, continues in one embodiment twelve (12) times seamlessly around the circumference of an expansion column, in the one embodiment that has six zigzag cycles around the circumference of the expansion column.

Various embodiments of the stent can include one or more of several different types of expansion columns. A first end expansion column in a proximal end can be a mirror image of a second expansion column in a distal end. A second expansion column nearest to the proximal end expansion column can have its mirror image in an expansion column next to a distal end expansion column. Such expansion columns can transition to a middle expansion column. The middle of the stent can include another type of expansion column that can repeat to make up the rest of the middle section of the stent of a predetermined length.

In some embodiments of the stent, the proximal end expansion column can include one or more types of expansion strut patterns forming different kinds of expansion strut pairs around the circumference of the proximal end expansion column. Such types include an expansion strut with a distal stepped-down section, an expansion strut with a straight-line configuration, and an expansion strut with a distal stepped-up section. A distal end expansion column can be a mirror image of the proximal end expansion column. Different types of expansion struts can be arranged in certain sequence. Joining loop sections can form expansion strut pair loops at a proximal end and at a distal end, for example in an alternating sequence.

An expansion column nearest to a proximal end expansion column and an expansion column nearest to a distal end expansion column can be mirror images. One or more types of expansion strut patterns are possible. Various embodiments of the stent can include one or more of: an expansion strut with a stepped-down section at a proximal end, an expansion strut with a stepped-down section at a distal end, an expansion strut with a straight line configuration, and an expansion strut with a stepped-up section at a proximal end and a stepped-down section at a distal end. Such types of expansion struts can be arranged in certain sequence. Joining loop sections can form expansion strut pair loops at a proximal end and at a distal end, for example in an alternating sequence. An expansion column nearest to a proximal end expansion column and an expansion column nearest to a distal end expansion column can have the same conjoining of expansion pair loops.

Expansion columns in the middle may have one or more types of expansion struts, such as an expansion strut with a stepped-down section at a proximal end, and an expansion strut with a stepped-down section at a distal end. A pair of these types can be conjoined by, for example, a joining loop section at a proximal end or at a distal end, making expansion strut pair loops in a proximal end or in a distal end in an alternating sequence.

Various embodiments of the stent can include multiple types of expansion columns. Particular configurations of an expansion strut pair and expansion columns can be created for specific performance purposes. The short stepped-up or stepped-down part and the longer straight part in an expansion strut with a sloped transitional zone between a long and short part can provide distinct expansion characteristic, smooth surface modulation effects, and well-formed crimping space to stent performance. A short stepped-down or stepped-up section of an expansion strut can be where a connecting strut can conjoin on a side of an expansion strut pair loop. A connecting strut can conjoin with an expansion strut as a direct extension from a side of an expansion strut pair loop and can be an integral stent structure, rather than a separate structure added, welded or attached. Separate terminology for stent elements, for example, expansion and connecting struts, conveniently describes the anatomy and function of various stent portions, and may not imply that previously separate elements are subsequently connected together.

Connecting struts can have a geometric configuration, for example a symmetrical quasi M-frame configuration. In the symmetrical quasi M-frame configuration, the center element can have an invaginated truncated conical shape (or a trapezoid shape), and/or with outer arms truncated short. A longitudinal axis of a connecting strut can align with a longitudinal axis of a stent. Various embodiments of the stent can have connecting struts with one or more of horizontal segments, slant-vertical sections, and short outer arm-end sections or bilateral short stems, with some number of pivot points. In one embodiment, connecting struts include three horizontal segments, two long slant-vertical sections, and two bilateral short stems, with six pivot points. The pivot points of a connecting strut have some radii of curvature of a varying degree to make the corners smooth with a good surface modulation. In one embodiment, the pivot points makes the stent flexible while inducing a very smooth surface geometry.

Connecting struts can conjoin on ipsilateral sides of expansion strut pair loops on each end. The center element, such as of an upside down trapezoid (or truncated conical shape) of the connecting strut can be invaginated into the connector space between the two apposing expansion strut pair loops that are, for example, aligned in a mirror image pattern. Some embodiments of the stent do not protrude into the main cell space. One configuration, a quasi M-frame connecting strut, divides the connector space into multiple portions. The bilateral short stems can be conjoined on ipsilateral sides of the apposed expansion strut pair loops, while the center element, the truncated conical shape or the trapezoid shape, can be invaginated into the connector space between the two apposed expansion strut pair loops.

In some embodiments of the stent, when two bilateral short stems of a connecting strut conjoins expansion strut pair loops on ipsilateral sides, the connecting strut can conjoin to the two apposing expansion strut pair loops on each side of the connecting strut. A stepped-down or a stepped-up section of an expansion strut can give a connecting strut a well-planned space for crimping. Conjoining of a connecting strut on ipsilateral sides, along with an invaginated center section or sections into a connector space with multiple pivot points can create flexibility, smooth surface modulation, conformability, cell geometry (for example, hexagonally expanded) and a well formed full vessel coverage stent net mesh without an excessive metal fraction.

In some embodiments of the stent, an end of a connecting strut can be conjoined to an expansion strut pair loop, making a ratio of expansion struts to connecting struts two to one.

In some embodiments of the stent, when the expansion columns and connecting columns are conjoined as a single unit, the stent can have a continuous, unbroken cylindrical form without breaks or de-linking around the circumference and along the length of the stent. The unbroken link between the expansion and connecting struts can make regular and evenly spaced asymmetrical cells. The cell size can be maximized or minimized by programming of the stent (design) platform, as the clinical or application requirements may dictate.

FIG. 16 shows one embodiment of a stent 410 in side elevation view, with a first expansion column 429, a second expansion column 430, a third expansion column 431, a first connecting strut column 432, and a second connecting strut column 433. The stent 410 has a proximal end 420 and a distal end 422. The stent 410 can have a tubular or cylindrical structure. The stent 410 can have a longitudinal length 424 and a longitudinal axis 426.

In some embodiments of the stent, an expansion column can be a zigzag and/or corrugated ring configuration of expansion struts. An expansion column, for example expansion column 430, in a stent 410 can be an unbroken circular ring. Multiple expansion strut columns can be interconnected with connecting struts continuously along the longitudinal axis 426 of the stent 410 in an unbroken manner to form a stent 410 having a tubular shape. The interconnections among expansion columns and connecting strut columns enclose spaces, or cells, formed by expansion struts and connecting struts. In the embodiment shown in FIG. 16, many cells have symmetrical geometry, for example the middle of the stent 410, but some cells, for example near proximal end 420 and distal end 422, can have asymmetrical geometry.

FIG. 17 shows one embodiment of a stent 410 in isometric view. A back half of the stent 410 can be seen through the front half of the stent 410. The shown embodiment of the stent 410 has a tubular structure with a central lumen, a is proximal opening 440, and a distal opening 442. Stent cells 434 include open spaces in the network of expansion struts and connecting struts. The lumen includes the central, open tunnel formed by the stent. The stent 410 has two different diameters, including an outer diameter 436 and an inner diameter 438, having a difference of a thickness of the stent 410. Both the outer diameter 436 and inner diameter 438 can change as the stent 410 goes through a crimping stage, when the diameters 436 and 438 are narrowed, and through a deployed stage, when the diameters 436 and 438 are expanded.

FIG. 18 shows one embodiment of a stent 410 in cut-open view. The stent 410 has a proximal end 420 and a distal end 422. This view of the stent 410 is a scale drawing for a 15 mm coronary stent. There are eight expansion columns and seven connecting strut columns. At the proximal end 420 are two different expansion columns 444 and 446, which are mirror images of two expansion columns 445 and 447 at the distal end 422. In the middle of the stent 410, there are four identical expansion columns 448. Interconnecting with eight expansion columns along the longitudinal axis 426 of the stent 410 are seven connecting strut columns. The first connecting strut column 530 in a proximal end and the last connecting strut column 530 are mirror images. In the middle of the stent 410 are two upright connecting strut columns 532 and three upside down connecting strut columns 134. There are a total of 449 cells of six different geometric configurations. Some cells have symmetrical geometry and some have asymmetrical geometry.

Expansion columns 444, 446, 448, 447 and 445 are vertically arranged with expansion strut pair loops aligned peak-to-peak. A short distal step-down segment of one expansion column is matched with a short proximal step-down segment of another expansion column. In the middle of the stent 410, a peak-to-peak matching alignment pattern of strut pair loops repeats. Geometric configurations of expansion columns 444 and 446 in the proximal end 420 and expansion columns 447 and 445 in the distal end 422 are mirror images from expansion columns 448 in the middle of the stent. Peak-to-peak alignment of expansion strut pair loops of distal and proximal step-down segments are consistent throughout the stent 410.

Connecting strut columns 530, 532 and 534 interconnect expansion columns 444, 446, 448, 447 and 445 in a continuous and unbroken manner along the length 424 and around the circumference 428 of the stent 410. The first and last connecting strut columns 530 use both upside down and upright quasi M-frame connecting struts. In the middle of the stent 410, connecting strut columns 532 use upright quasi M-frame connecting struts, whereas connecting strut columns 534 have upside down quasi M-frame connecting struts. The quasi M-frame connecting struts are mounted on the ipsilateral sides of two apposed expansion strut pair loops with a distal and proximal step-down segments. This apposed arrangement of distal versus proximal step-down segments of the corrugated loops of expansion columns 430 is for a smooth and efficient crimping space for proximal and distal bilateral short stems of quasi M-frame connecting struts in the stent 410.

The stent 410 in FIG. 18 has the proximal end 420 on the left and the distal end 422 on the right. The stent 410 has a length 424 horizontally and a circumference 428 vertically, with a longitudinal axis 426 horizontally along the length 424 from the proximal end 420 to the distal end 422.

A width (horizontal dimension) of expansion columns is wider than a width of connecting strut columns. However, a width of a connecting strut column could be made the same or larger than a width of an expansion column. The variation of width ratio between a connecting strut column and an expansion column are within the scope of present invention of stent 410. The number of expansion strut cycles in an expansion column and the number of connecting struts in a connecting strut column can be made variably different. Variable numbers of making expansion strut cycles and connecting struts are within the scope of the present invention of the stent 410.

FIG. 19A shows a magnified view of a middle section of one embodiment of a stent 410. FIG. 19A shows identical expansion columns 448. Each expansion column 448 can have six cycles of continuous, unbroken expansion strut pair loops with six loops on a proximal end and six loops on a distal end. Each expansion strut pair loop in an expansion column 448 can include a stair step expansion strut 454 with a stepped-down short segment 456 in a proximal end and a stair step expansion strut 454 with a short stepped-down segment 458 in a distal end, in a regularly alternating sequence. The embodiment of stent 410 of FIG. 18 includes twelve stair step expansion struts 454 in an expansion column 448. A pair of stair step expansion struts 454 is conjoined by a joining loop 470 in a proximal end and a pair of stair step expansion struts 454 is conjoined by a joining loop 472 in a distal end. When a pair of stair step expansion struts 454 is conjoined by a joining loop 470 or 472, a loop is formed.

An expansion strut 454 can have a longer straight segment and a shorter stepped down segment 456 in a proximal end. A transitional slope 474 can be between a stepped down proximal segment 456 and a straight segment in a stair step expansion strut 454. Likewise, a transitional slope 476 can be between a stepped down distal segment 458 and a straight segment in a stair step expansion strut 454. Expansion strut pair loops of an expansion column 448 can be identical in expansion columns marked 448.

In an expansion column 448, a straight segment of expansion strut 454 can have a longitudinal axis 482 in a horizontal direction. Similarly, a proximal short stepped down segment 456 can have a longitudinal axis 484, which also lies horizontally and roughly parallel with an axis 480 although the axis 484 does not have to be parallel with the axis 482. A distal short stepped down segment 458 has a longitudinal axis 486, which also lies horizontally and may be parallel with the axis 480, although the axis 486 does not have to be parallel with an axis 482.

Expansion columns 448 can be vertically aligned, with proximal peaks 470 of expansion strut pair loops of one expansion column 448 apposed with distal peaks 472 of expansion strut pair loops of adjacent expansion column 448. Short stepped down segments 456 and 458 of adjacent expansion columns 448 are aligned on the ipsilateral, or same sides. Similarly, long straight segments of expansion struts 454 in an adjacent expansion column 448 can also be aligned on the ipsilateral sides. The ipsilateral apposition of stepped down segments 456 and 458 between two adjacent expansion columns 448 allows for symmetrical conjoining of a quasi M-frame connecting strut to adjacent expansion columns 448.

As expansion columns are arranged in FIG. 19A, a longitudinal axis 482 of a stair step expansion strut 454 in an expansion column 448 is roughly parallel with a longitudinal axis 482 of a stair step expansion strut 454 in adjacent expansion column 448, although non-paralleling of these two axis 482 in expansion struts 454 in adjacent expansion columns does not have to be so. This variation is within the scope of present invention of stent 410.

An upright quasi M-frame connecting strut 490 can be conjoined on the ipsilateral sides of expansion strut pair loops in peak-to-peak apposition on the stepped down segments of the expansion strut pair loops of adjacent expansion columns 448. The center element of quasi M-frame connecting strut 490 can be located within the confines of the connector space between two apposed expansion strut pair loops of adjacent expansion columns 448. An upside down quasi M-frame connecting strut 492 can be conjoined on the ipsilateral sides of expansion strut pair loops in peak-to-peak apposition on the straight longer segment side of expansion strut pair loops of adjacent expansion columns 448. The center element of upside down quasi M-frame connecting strut 492 can also be located within the confines of the connector space between two apposed expansion strut 454 pair loops of adjacent expansion columns 448.

FIG. 19B shows a magnified view of a middle section of one embodiment of a stent 410. An upright quasi M-frame connecting strut 490 conjoins two adjacent expansion columns 448. A connecting strut 490 has a longitudinal axis 494, which lies horizontally along the same direction as longitudinal axis 426 of the stent 410.

An upright quasi M-frame connecting strut 490 has a proximal bilateral short stem 500 in the proximal end and a distal bilateral short stem 502 in the distal end. These two stems are anchoring roots a connecting strut 490 to conjoin, on ipsilateral sides, stepped down short segments 456 and 458 of apposed expansion strut pair loops of two adjacent expansion columns 448. A quasi M-frame connecting strut 490 has a symmetrical geometric shape. There are three horizontal segments 504, 506 and 508. A horizontal segment 504 is an extension from a proximal stem 500 through a radius of curvature 514. A distal horizontal segment 508 along with a distal stem 502 and a radius of curvature 524 is a mirror image of a proximal horizontal segment. A middle horizontal segment 506 is at the base of a truncated cone of the quasi M-frame connecting strut 490. On both sides of a middle horizontal segment 506 are two mirror image vertical slant segments 510 and 512. A proximal vertical slant segment 510 is an extension of proximal horizontal segment 504 through a radius of curvature 516 and is an extension of middle horizontal segment 506 through a radius of curvature 518. Likewise, a distal vertical slant segment 512 is an extension of a middle horizontal segment 506 through a radius of curvature 520 and is an extension of distal horizontal segment 508 through a radius of curvature 512. There are six radii of curvature 514, 516, 518, 520, 522, and 524 in a quasi M-frame connecting strut 4490. These six radii of curvatures serve as flexibility pivot points in the connecting strut 490, so that the stent 410 can have more flexibility. The structure of a quasi M-frame connecting strut 490 can be substantially or entirely confined inside an imaginary "connector space" between two apposed expansion strut pair loop peaks 470 and 472 of adjacent expansion columns 448. The central element, such as a truncated cone, of a quasi M-frame connecting strut 490, can be inverted or invaginated into a connector space between apposed expansion strut pair loops of adjacent expansion columns 448, instead of projecting substantially into the free space of the stent cell 434. This can enhance stent crimping as well as smooth surface modulation during a delivery phase of stent implant procedure.

The upside down quasi M-frame connecting strut 492 is a reverse image of an upright quasi M-frame connecting strut 490. A quasi M-frame connecting strut 492 in a connector space 534 is similar to an upright quasi M-frame connecting strut 490, but having an upside down orientation, rather than an upright orientation of the upright quasi M-frame connecting strut 490. Designations of an upside down quasi M-frame connecting strut are similar to that of an upright quasi M-frame connecting strut 492. In the middle of the stent 410, connecting strut columns 432 can alternate between upright quasi M-frame connecting strut column 532 and upside down quasi M-frame connecting strut column 534, while expansion columns 448 can repeat a same configuration. Upside down connecting struts 492 in connecting strut columns 534 can be conjoined on the ipsilateral sides of long straight segments of expansion struts 454 of expansion strut pair loop peaks 470 and 472 of adjacent expansion columns 448.

The total length of an M-frame 490 can be substantially longer than the width of a connecting strut column space 532. This can compensate a foreshortening of the stent 10 when expanded, and enhance the flexibility of connecting strut column 532.

In connecting strut column 532, a quasi M-frame connecting strut 490 is conjoined to ipsilateral sides on the proximal or distal stepped down segments 456 and 458 of two apposed expansion strut pair loops of adjacent expansion columns 448.

FIG. 20A shows a magnified view of an end section of one embodiment of a stent 410, such as a proximal end 420 of stent 410. This figure focuses on the details of the expansion columns 444, 446, and 448.

FIG. 20B shows a magnified view of an end section of one embodiment of a stent 410, with details of connecting strut columns 530 and 534.

In some embodiments of the invention a stent 610, such as is shown in FIGS. 21-25 includes connecting struts and expansion struts wherein at least apportion of each connecting strut is substantially parallel to a portion of the adjacent expansion struts.

Figure 21:
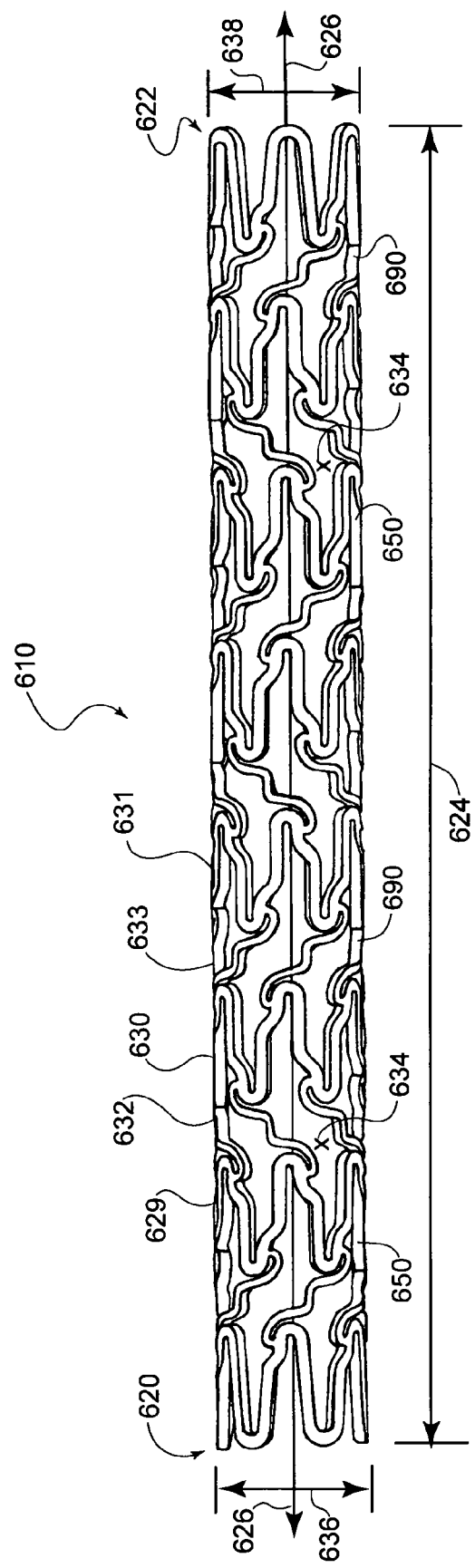
FIG. 21 shows a side elevation view of an embodiment of a stent, such as a tubular stent.

FIG. 21 shows an embodiment having a first expansion column 629, a second expansion column 630, a third expansion column 631, a first connecting strut column 632, and a second connecting strut column 633. The first expansion column, the second expansion column, and the third expansion column can include individual expansion struts forming a plurality of expansion strut pairs. In many embodiments of the stent, two adjacent expansion strut pairs share a common strut.

The first connecting strut column and the second connecting strut column include a plurality of individual connecting struts. Each connecting strut has a stair-step geometric configuration with a curvilinear proximal section and a curvilinear distal section. The first connecting strut column can include individual first connecting struts and the second connecting strut column can include individual second connecting struts. The first connecting column couples the first and second expansion columns. FIG. 21 shows an example where the first connecting column 632 couples the first expansion column 629 and the second expansion column 630. The second connecting column 633 couples the second expansion column 630 and the third expansion column 631.

Each expansion strut can have a stair-step configuration. Distal ends of expansion strut pairs of the first expansion column that are coupled to proximal ends of expansion strut pairs of the second expansion column can be vertically offset. Distal ends of expansion strut pairs of the second expansion column that are coupled to proximal ends of expansion strut pairs of the third expansion column can also be vertically offset.

Some embodiments of the stent include connecting struts with five sections, including an intermediate section, a proximal curvilinear section and a distal curvilinear section. The proximal section of each first connecting strut can be contralaterally conjoined to an expansion strut pair of the first expansion column. The distal section can be contralaterally conjoined to an expansion strut pair of the second expansion column. The proximal and distal sections can have the same lengths.

At least a portion of the proximal and distal curvilinear section can be parallel to a portion of an expansion strut pair loop in the first expansion column or in the second expansion column.

The proximal section can include a terminal end conjoined to an expansion strut in the first expansion column, and at least one surface that is conjoined to at least one surface of an expansion strut in the first expansion column. The distal section includes a terminal end conjoined to an expansion strut in the second expansion column, and at least one surface that is conjoined to an expansion strut in the second expansion column.

At least one of the proximal and distal sections of each connecting strut can be contralaterally conjoined to an expansion strut pair of the first and second expansion columns, or to an expansion pair of the second and third expansion columns.

At least a portion of the curvilinear proximal section of each connecting strut can be parallel to a portion of an expansion strut pair loop. At least a portion of the curvilinear distal section of each connecting strut can be parallel to a portion of an expansion strut pair loop of an expansion column.

At least a portion of the curvilinear proximal section of each connecting strut can be positioned in close proximity to an expansion strut pair loop of an expansion column. At least a portion of the curvilinear distal section of each connecting strut can be positioned in close proximity to an expansion strut pair loop. Close proximity can be in the range of 0.001 to 0.050 of an inch, in the range of 0.001 to 0.040 of an inch, or in the range of 0.001 to 0.030 of an inch.

In various embodiments of the stent each connecting strut can have a proximal end, a distal end, four pivot points, and a longitudinal axis. The proximal end can extend in a first direction. The distal end of a connecting strut can extend in an second direction opposite to the first direction.

Figure 25:
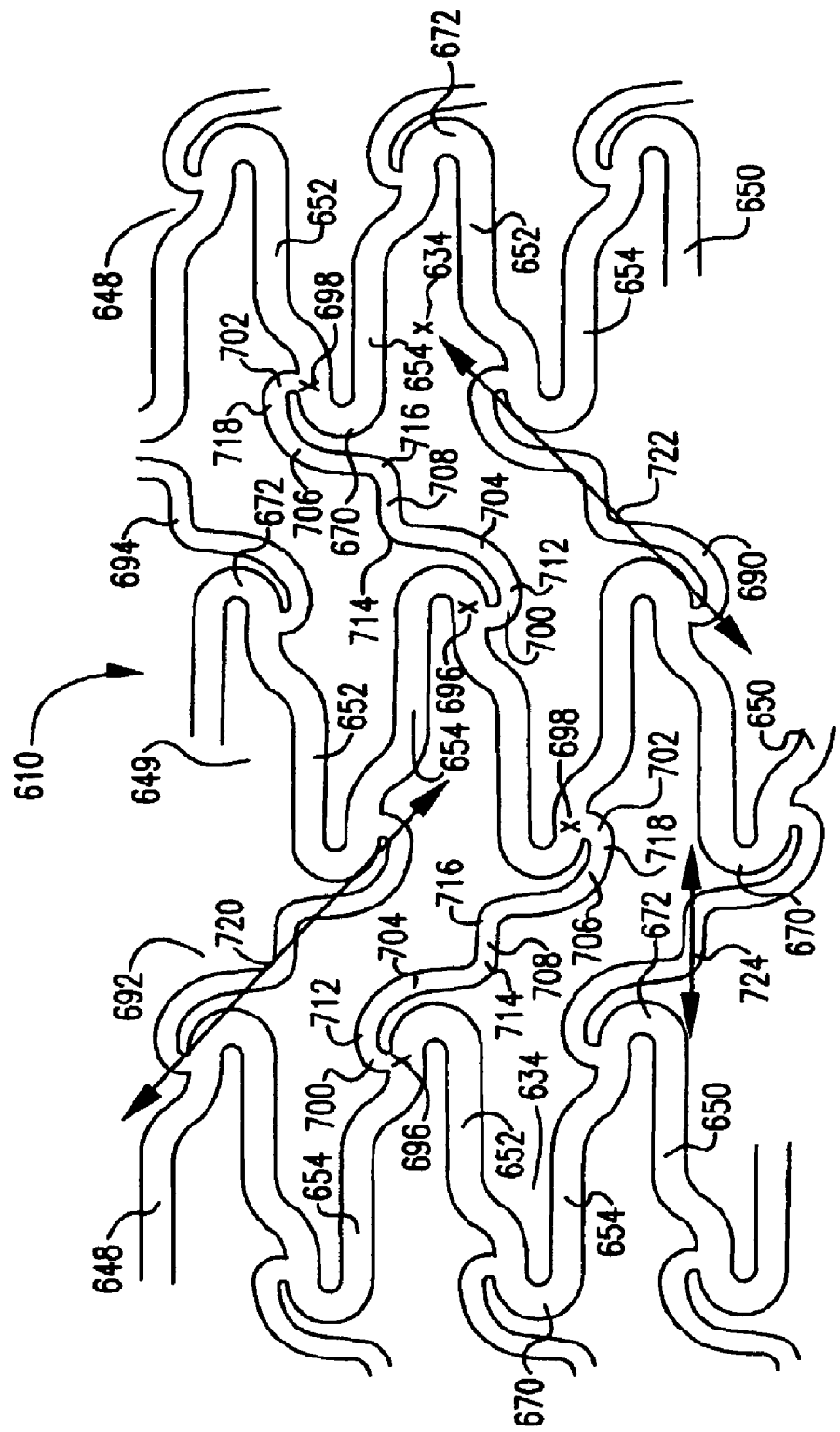
FIG. 25 shows a magnified view of a middle section of an embodiment of a stent, such as a stent of FIGS. 21, 22, and 23. Some details are shown of connecting strut columns.

Each connecting strut in the first connecting strut column has two radii of curvature each with the proximal and distal curvilinear section. FIG. 25 shows examples pivot points 712 and 714 having radii of curvature in the proximal curvilinear section, and pivot points 716 and 718 having radii of curvatures in the distal curvilinear section. Each pivot point can have at least one radius of curvature.

The longitudinal axis of the connecting strut may be non-parallel to a longitudinal axis of the stent. In some embodiments of the stent, each connecting strut in a same connecting strut column can share the similar longitudinal axis, which can be mutually parallel.

Each first connecting strut can have a longitudinal axis that extends in a first direction. Each second connecting strut can have a longitudinal axis that extends in an opposite second direction.

The intermediate section can have a longitudinal axis. The longitudinal axis of an intermediate section may be parallel to an expansion strut in the first expansion column, parallel to an expansion strut in the second expansion column, non-parallel to the longitudinal axis of the first connecting strut, and parallel to the longitudinal axis of the stent. The intermediate section is coupled to the curvilinear proximal section and the curvilinear distal section.

Each connecting strut is contralaterally conjoined to the first and second expansion columns. At least a portion of the connecting struts can have asymmetrical geometric configurations.

Some embodiments of the stent include a first end expansion column and a second end expansion column. The first and second end expansion columns can define a proximal and a distal end of the stent, and are mirror images of each other.

A plurality of cells can be defined by the first expansion column, the second expansion column and the first connecting strut column. Cells can have evenly spaced, asymmetrical geometric shapes. Cells can also have evenly spaced geometric shapes with a quasi-hexagonal geometry in a nominally expanded state.

Expansion strut pair loops in two adjacent expansion columns can be aligned in a peak-to-valley, in a valley-to-peak geometry, or in a peak-to-peak geometry.

An expansion column includes expansion struts that form expansion strut pairs in a ring shape. Each pair of expansion struts has two struts conjoined by a joining strut section at either a proximal or distal end. This pairing between two adjacent expansion struts conjoined by a joining strut section alternates from proximal to distal and distal to proximal. This sequence, in one embodiment, can continue twelve times seamlessly around the circumference of a ring for six zigzag cycles around the circumference of the ring shape. In such an embodiment there are twelve expansion strut pairs in alternating positions in an expansion column. There can also be twelve joining strut sections, six in a proximal end and six in a distal end in an alternating sequence. Expansion struts can include one or more of a short stepped-down segment at a proximal end, a short stepped down segment at a distal end, a short stepped-up segment at a proximal end, and a short stepped-up segment at a distal end. Some embodiments of the stent include expansion struts with a short-sloped transitional segment between the long and short parts in the stair-step expansion struts. Various embodiments of the stent can include various combination of one or more of different expansion struts. At proximal or distal end of the stent, the terminating side of an end expansion column can have smooth and evenly rounded loops.

Various embodiments of the stent include one or more types of expansion columns. A first expansion column includes various expansion strut pairs. A joining strut section at a proximal end can join an expansion strut with a short stepped-down section at a proximal end and an expansion strut with a short stepped-down section at a distal end, forming an expansion strut pair loop. A joining strut section at a distal end can join an expansion strut with a short stepped-down section at a distal end and an expansion strut with a short stepped-down section at a proximal end, forming an expansion strut pair loop. These expansion strut pairs alternate, for example for six cycles, around the expansion ring without a break.

A second expansion column includes various expansion strut pairs. A joining strut section at a proximal end can join an expansion strut with a short stepped-up section at a proximal end and an expansion strut with a short stepped-up section at a distal end, forming an expansion strut pair loop. A joining strut section at a distal end can join an expansion strut with a short stepped-up section at a distal end and an expansion strut with a short stepped-up section at a proximal end, forming an expansion strut pair loop. These expansion strut pairs alternate, for example for six cycles, around the expansion ring without a break.

Different types of expansion columns can be arranged in an alternating sequence, inter-linked along the length of the stent by connecting columns. Stepped-up or stepped-down segments with a sloped transitional section can provide flexibility, smooth surface modulation effects, and well-formed crimping space to the stent. A connecting strut can conjoin with an expansion strut pair at a short stepped-down or stepped-up section of an expansion strut. A connecting strut can be a direct extension of an expansion strut and be integral to the stent structure rather than a separate structure added, welded, or attached. Separate terminology for stent elements, for example expansion and connecting struts, conveniently describing the anatomy and function of various stent portions.

Connecting struts can have a curvilinear double stair step shape with a longitudinal axis diagonally tilted to one side or the other side from the vertical, due to the diagonal orientation. Connecting struts of different connecting strut columns can have different-longitudinal axes, which can be mirror images. In some embodiments of the stent, a connecting strut has three segments, two end-stem sections and four pivot points. Pivot points can have a varying radius of curvature. These multiple pivot points are responsible for flexibility. One end of a connecting strut can conjoin with an expansion strut pair in one expansion strut column and another end of the connecting strut can conjoin to another expansion strut pair in an adjacent expansion strut column. The connecting strut can link two apposing expansion strut pairs in a diagonal orientation. A diagonal orientation of a connecting strut of the stent gives added flexibility, excellent crimping, vessel conformability and smooth surface modulation to the stent.

Further, when a connecting strut conjoins expansion strut pairs, both ends of a connecting strut conjoin to the contralateral sides of apposing expansion strut pairs of adjacent expansion columns, at a stepped down or a stepped up sections. Conjoining a connecting strut on contralateral sides, along with a diagonal orientation and multiple pivot points, can provide good stent performance characteristics.

In some embodiments of the stent, the ratio of expansion strut to connecting strut number is two to one, where such as when a connecting strut is conjoined to expansion strut pairs.

When the expansion columns and connecting columns are conjoined, the stent can have a continuous, unbroken cylindrical form without breaks or de-linking around the circumference and along the length of the stent. Unbroken links between the expansion and connecting struts can make regular and evenly spaced asymmetrical cells. The cell size can be maximized or minimized by programming of the stent design platform, as dictated by clinical or applications requirements.

FIG. 21 shows one embodiment of a stent 610 in side elevation view, with a first expansion column 629, a second expansion column 630, a third expansion column 631, a first connecting strut column 632, and a second connecting strut column 633. The stent 610 has a proximal end 620 and a distal end 622. The stent 610 has a tubular or cylindrical structure. The stent 610 has a longitudinal length 624 and a longitudinal axis 626.

In some embodiments of the stent, an expansion column can be a zigzag or corrugated ring configuration of expansion struts. An expansion column, for example expansion column 630, in a stent 610 can be an unbroken circular ring. Multiple expansion strut columns can be interconnected with connecting struts continuously along the longitudinal axis 626 of the stent 610 in an unbroken manner to form a stent 610 having a tubular shape. The interconnections among expansion columns and connecting strut columns enclose spaces, or cells, formed by expansion struts and connecting struts. In the embodiment shown in FIG. 21, all cells have asymmetrical geometry. The stent 610 has two different diameters, including an outer diameter 636 and an inner diameter 638, having a difference of a thickness of the stent 610. Both the outer diameter 636 and inner diameter 638 can change as the stent 610 goes through a crimping stage, when the diameters 636 and 638 are narrowed, and through a deployed stage, when the diameters 636 and 638 are expanded.

Figure 22:
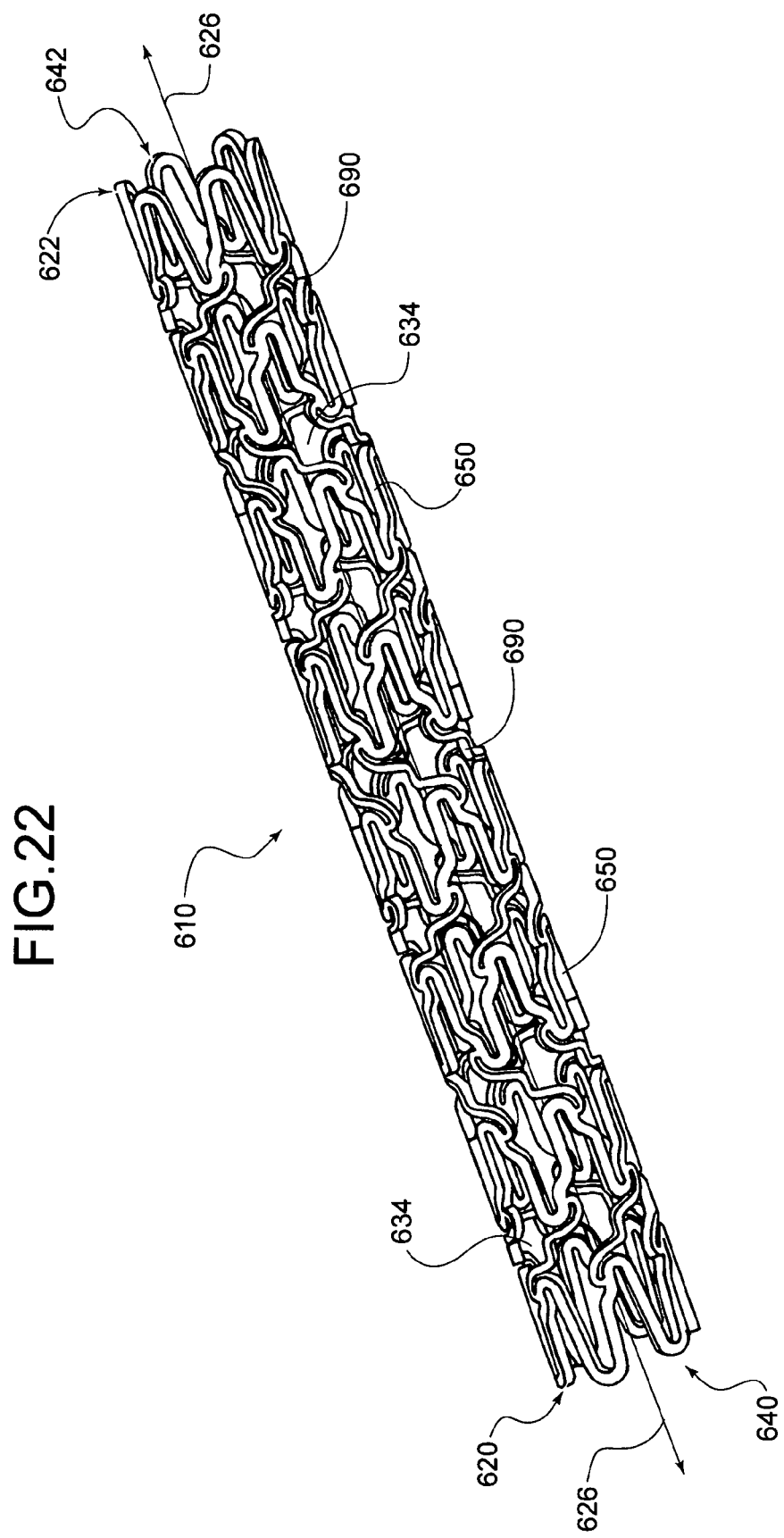
FIG. 22 shows an isometric view of an embodiment of a stent, such as a tubular stent.

FIG. 22 shows one embodiment of a stent 610 in isometric view. A back half of the stent 610 can be seen through the cell space of the front half of the stent 610. The shown embodiment of the stent 610 has a tubular structure with a central lumen, a proximal opening 640, and a distal opening 642. Stent cells 634 include open spaces in the network of expansion struts and connecting struts. The lumen includes the central, open tunnel formed by the expansion and connecting struts of the stent.

Figure 23:
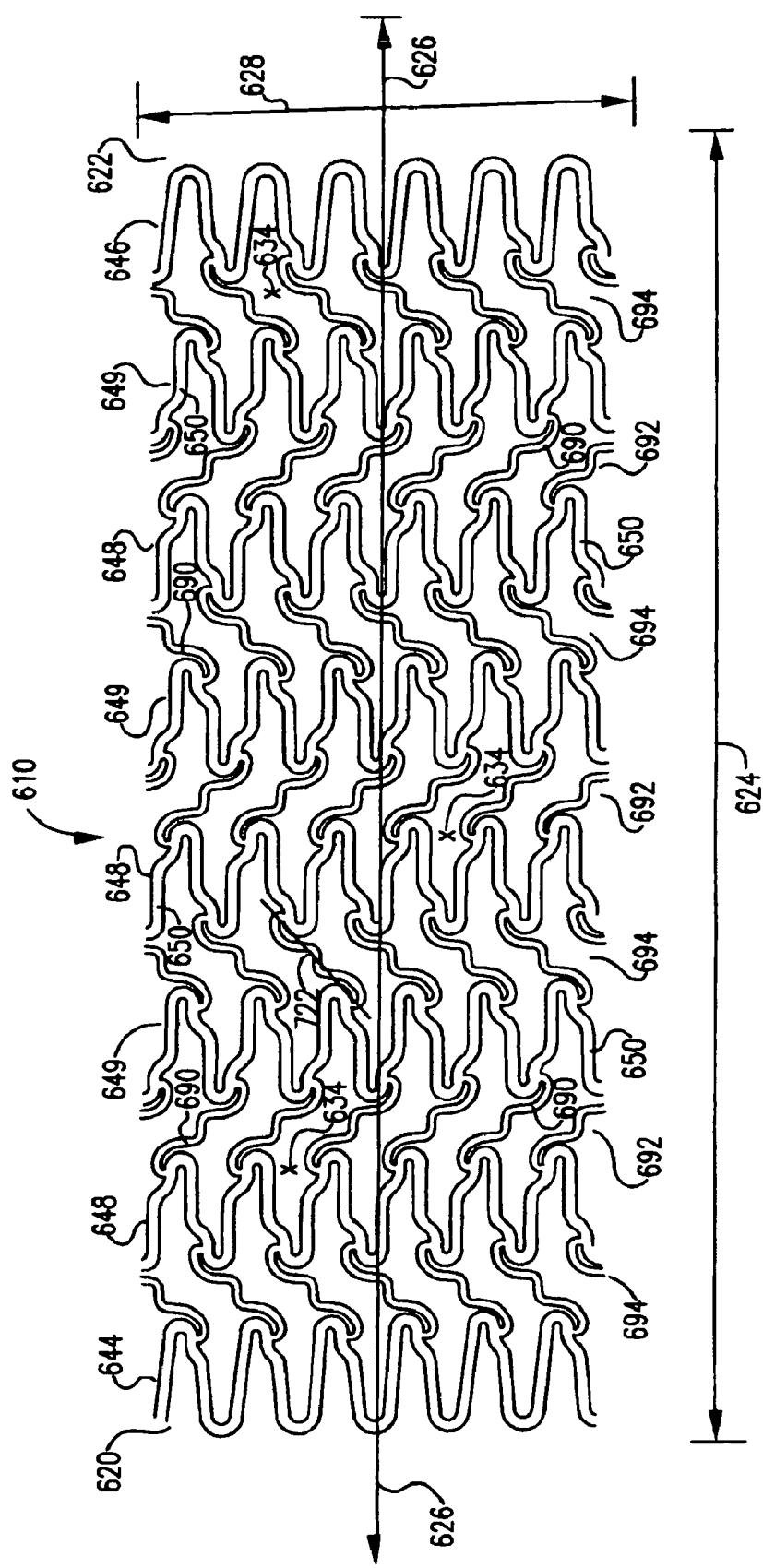
FIG. 23 shows a cut-open view of an embodiment of a stent. Various expansion columns and connecting strut columns are shown.

FIG. 23 shows one embodiment of a stent 610 in cut-open 2-dimensional view. The stent 610 has a proximal end 620 and a distal end 622. This view of the stent 610 is a scale drawing for a 15 mm coronary stent. There are eight expansion columns and seven connecting strut columns. At the proximal end 620 is an expansion column 644, which is a mirror image of an expansion columns 646 at the distal end 622. In the middle of the stent 610, there are six expansion columns, such that an expansion column 649 alternates with an expansion column 648. Interconnecting with eight expansion columns along the longitudinal axis 626 of the stent 610 are seven connecting strut columns including four connecting strut columns 694 and three connecting strut columns 692, such that a connecting strut column 694 alternates with a connecting strut column 692. There are a total of 642 cells of various asymmetric configurations. All the cells in this embodiment have asymmetrical geometry. Expansion columns 644, 646, 648, and 649 are vertically arranged with expansion strut pair loops aligned peak-to-valley. Connecting strut columns 692 and 694 interconnect expansion columns 644, 646, 648, and 649 in a continuous and unbroken manner along the length 624 and around the circumference 628 of the stent 610.

The stent 610 in FIG. 23 has the proximal end 620 on the left and the distal end 622 on the right. The stent 610 has a length 624 horizontally and a circumference 628 vertically, with a longitudinal axis 626 horizontally along the length 624 from the proximal end 620 to the distal end 622.

A width (horizontal dimension) of expansion columns is wider than a width of connecting strut columns. However, a width of a connecting strut column could be made the same or larger than a width of an expansion column. The variation of width ratio between a connecting strut column and an expansion column are within the scope of present invention of stent 610. The number of expansion strut cycles in an expansion column and the number of connecting struts in a connecting strut column can be made variably different. Variable numbers of making expansion strut cycles and connecting struts are within the scope of the present invention of the stent 610.

In some embodiments of the stent, one type of expansion column includes various expansion strut pairs. A joining strut section at a proximal end conjoins an expansion strut with short stepped-down section at a proximal end and an expansion strut with a short stepped-down section at a distal end, forming an expansion strut pair loop. A joining strut section at a distal end conjoins an expansion strut with a short stepped-down section at a distal end and an expansion strut with a short stepped-down section at a proximal end, forming an expansion strut pair loop. These expansion strut pairs alternate, for example for six cycles, around the expansion ring without a break.

Figure 24:
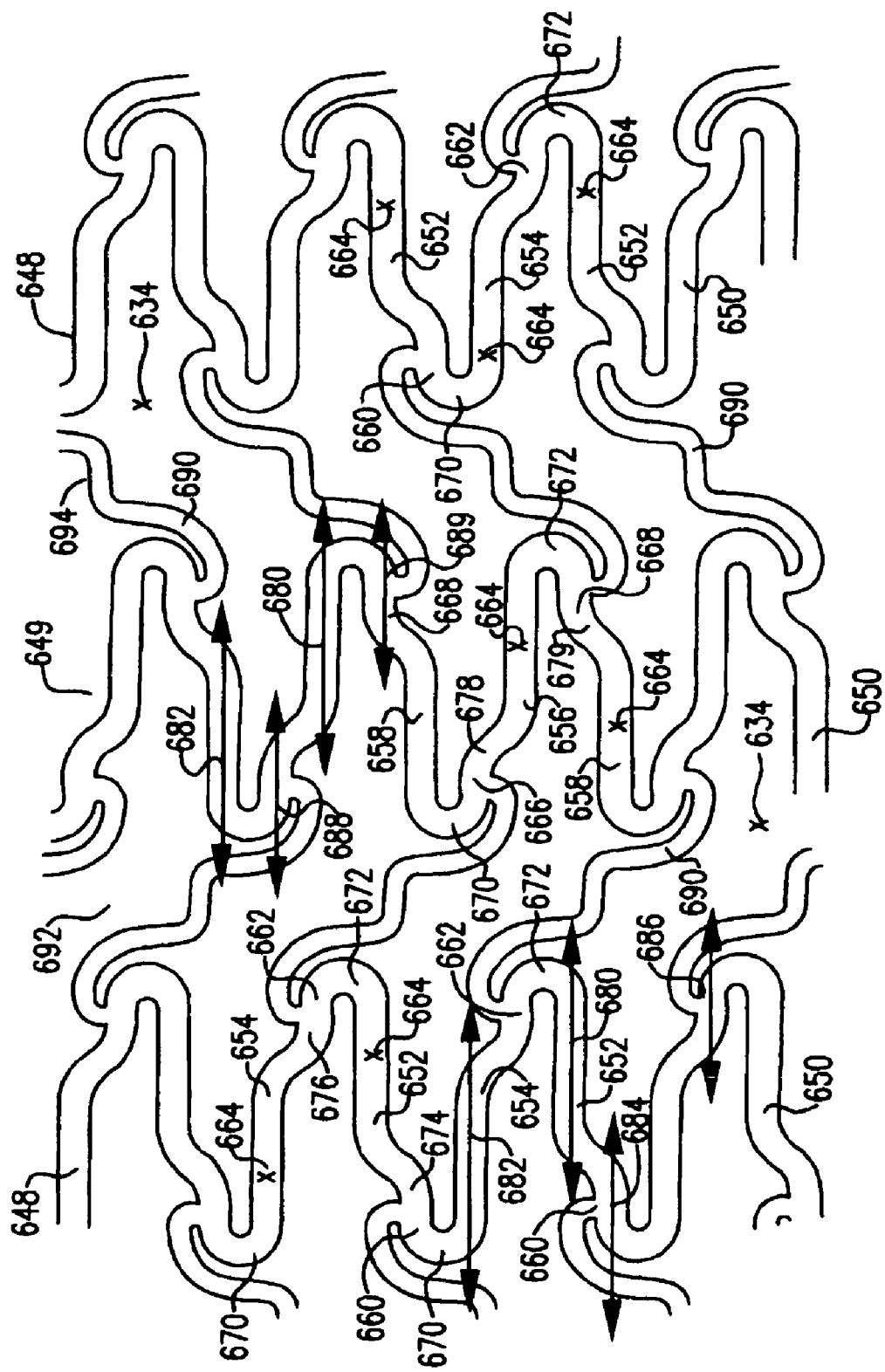
FIG. 24 shows a magnified view of a middle section of an embodiment of a stent, such as a stent of FIGS. 21, 22, and 23. Some details are shown of expansion columns.

FIG. 24 shows an embodiment having this type of expansion column 648. A joining strut section 670 at a proximal end conjoins an expansion strut 652 with a short stepped-down section at a proximal end and an expansion strut 654 with a short stepped-down section at a distal end forming an expansion strut pair loop. A joining strut section 672 at a distal end conjoins an expansion strut 654 with a short stepped-down section at a distal end 662 and an expansion strut 652 with a short stepped-down section at a proximal end 660, forming an expansion strut pair loop.

Another type of expansion column includes various expansion strut pair combinations. A joining strut section at a proximal end conjoins an expansion strut with a short stepped-up section at a proximal end and an expansion strut with a short stepped-up section at a distal end, forming an expansion strut pair loop. A joining strut section at a distal end conjoins an expansion strut with a short stepped-up section at a distal end and an expansion strut with a short stepped-up section at a proximal end, forming an expansion strut pair loop.

FIG. 24 shows an embodiment having this type of expansion column 649. A joining strut section 670 at a proximal end conjoins an expansion strut 656 with a short stepped-up section at a proximal end 666 and an expansion strut 658 with a short stepped-up section at a distal end 668, forming an expansion strut pair loop. A joining strut section 672 at a distal end can join an expansion strut 658 with a short stepped-up section at a distal end 668 and an expansion strut 656 with a short stepped-up section at a proximal end 666, forming an expansion strut pair loop.

These proximal and distal expansion strut pairs alternate, for example for six cycles, around the expansion ring without a break.

A transitional slope 674 can be between a stepped down proximal section 660 and a straight section 664 in a stair step expansion strut 652. Likewise, a transitional slope 676 can be between a stepped down distal section 662 and a straight section 664 in a stair step expansion strut 654. A transitional slope 678 can be between a stepped up proximal section 666 and a straight section 664 in a stair step expansion strut 656. Likewise, a transitional slope 679 can be between a stepped up distal section 668 and a straight section 664 in a stair step expansion strut 658.

FIG. 25 shows an example of connecting strut column 692 and connecting strut column 694. Connecting struts can have a curvilinear double stair step shape with a longitudinal axis is tilted to one side or the other side from the vertical plane, due to the diagonal orientation of connecting struts. Connecting struts of different connecting strut columns can have different longitudinal axes, which can be mirror images. For example, longitudinal axis 720 for connecting struts in connecting strut column 692 is different from longitudinal axis 722 for connecting struts in connecting strut column 694. In some embodiments of the stent, a connecting strut has three segments, two end-stem sections and four pivot points. FIG. 25 shows connecting struts with a proximal curvilinear segment 704, central segment 708, distal curvilinear segment 706, proximal end-stem 700, distal end-stem 702, and pivot points 712, 714, 716, and 718. Pivot point 712 is a junction between proximal end-stem 700 and proximal curvilinear segment 704, pivot point 714 is a junction between proximal curvilinear segment 704 and central segment 708, pivot point 716 is a junction between central intermediate segment 708 and distal curvilinear segment 706, and pivot point 718 is a junction between distal curvilinear segment 706 and distal end-stem 702. These pivot points can have a varying degree of radius of curvature. These multiple pivot points are responsible for flexibility of the stent and for prevention of foreshortening of the stent. One end of a connecting strut can conjoin with an expansion strut pair in one expansion strut column and another end of the connecting strut can conjoin to another expansion strut pair in an adjacent expansion strut column. For example, a connecting strut in connecting strut column 692 has a proximal end 696 conjoined to an expansion strut in one expansion column, and a distal end 698 conjoined to an expansion strut in another expansion column. Proximal end 696 and distal end 698 of the connecting strut are conjoined to contralateral sides of apposing expansion strut pairs of adjacent expansion columns, at a stepped down or a stepped up sections. Conjoining a connecting strut on contralateral sides, along with a diagonal orientation and multiple pivot points of the connecting strut provides good stent performance characteristics. The connecting strut can link two apposing expansion strut pairs in a diagonal orientation. A diagonal orientation of a connecting strut of the stent gives added flexibility, excellent crimping, vessel conformability and smooth surface modulation to the stent.

Figure 26:
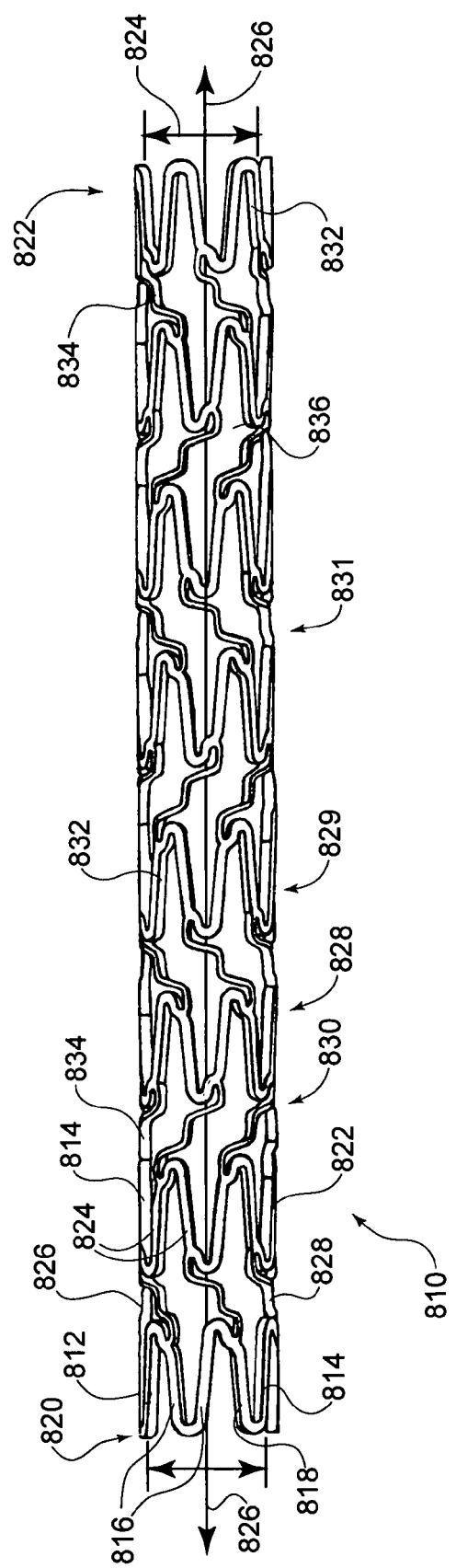
FIG. 26 is a side-elevation view of one embodiment of an unexpanded stent of the present invention.
Figure 27:
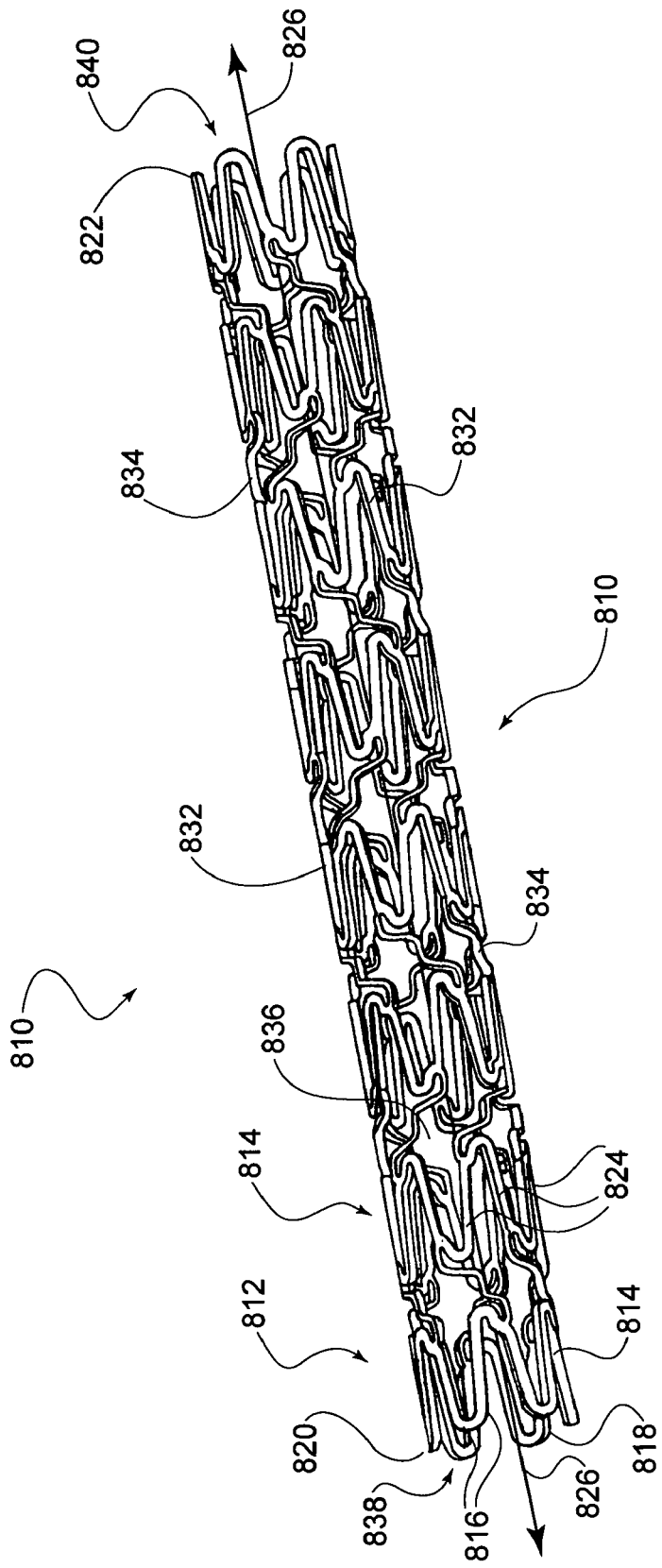
FIG. 27 is an isometric view of the FIG. 26 stent drawn in scale for a 15 mm length.

Referring now to FIGS. 26 and 27, one embodiment of a stent 810 of the present invention is illustrated in a non-expanded state. Stent 810 includes a first expansion column 812 with individual expansion struts 814 that form a plurality of expansion strut pairs 816. Adjacent expansion strut pairs 816 in first expansion column 812 share a common strut, indicated as 818. A second expansion column 820 also has individual expansion struts 822 that form a plurality of expansion strut pairs 822. Adjacent expansion strut pairs 822 in second expansion column 820 share a common strut, indicated as 824. Stent 810 is configured to provide easy delivery that is achieved with a sufficient level of flexibility in combination with a delivery balloon, a smooth surface modulation without tulips and a reasonable radiopacity during the delivery phase of stent 810.

Stent 810 provides enhanced flexibility and conformability while maintaining a full vessel coverage with optimal metal fraction. Additionally, stent 810 has, (i) substantially evenly expanding stent struts, (ii) excellent radial strength and radiopacity and (iii) smooth surface modulations in both the delivery and deployed phases of the stent life cycle. Stent 810 has a continuous, unbroken cylindrical form without any break or de-linking around the circumference and along its length.

Figure 28A:
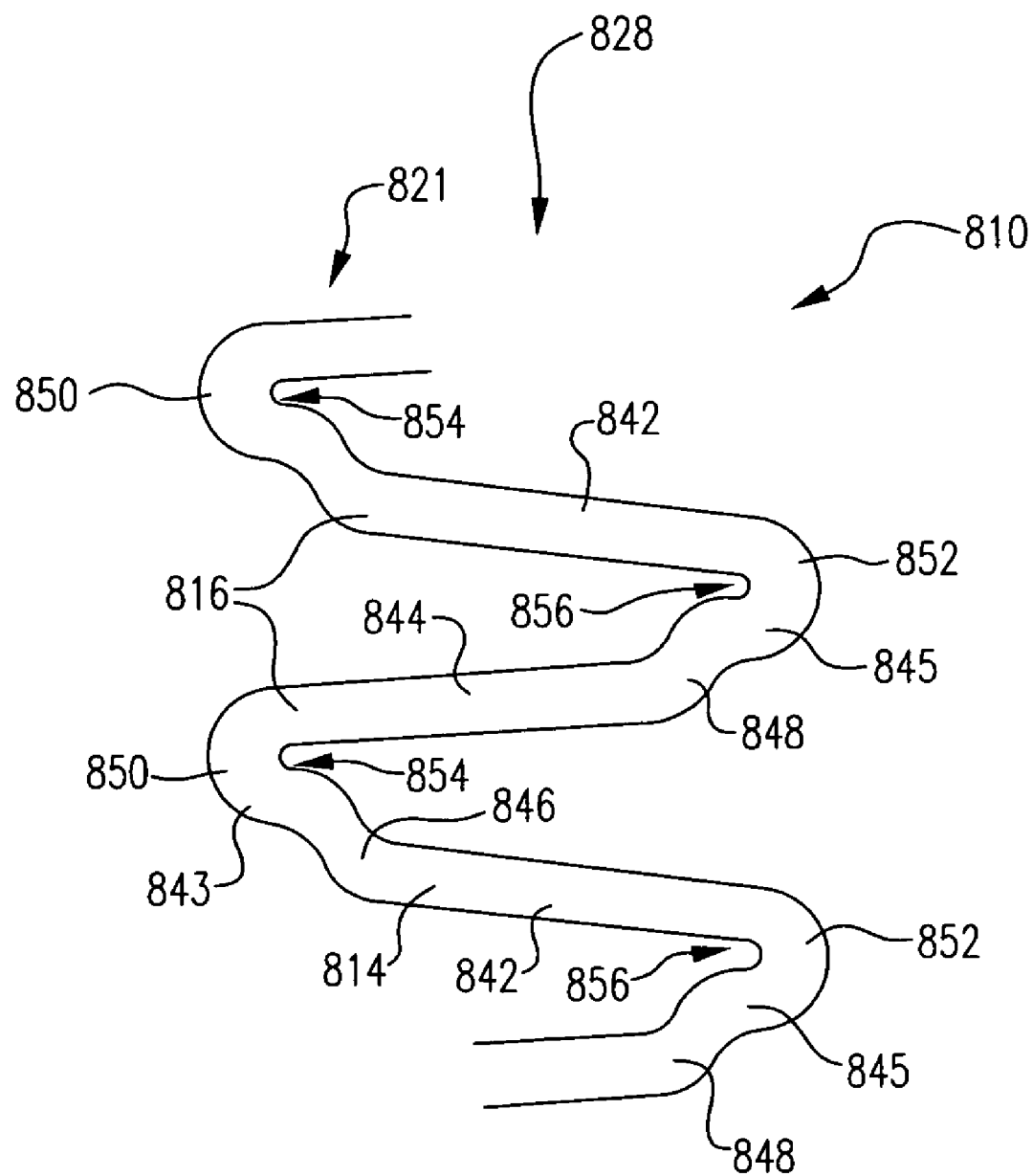
FIG. 28 is a close up view of the first and second expansion columns.
Figure 28B:
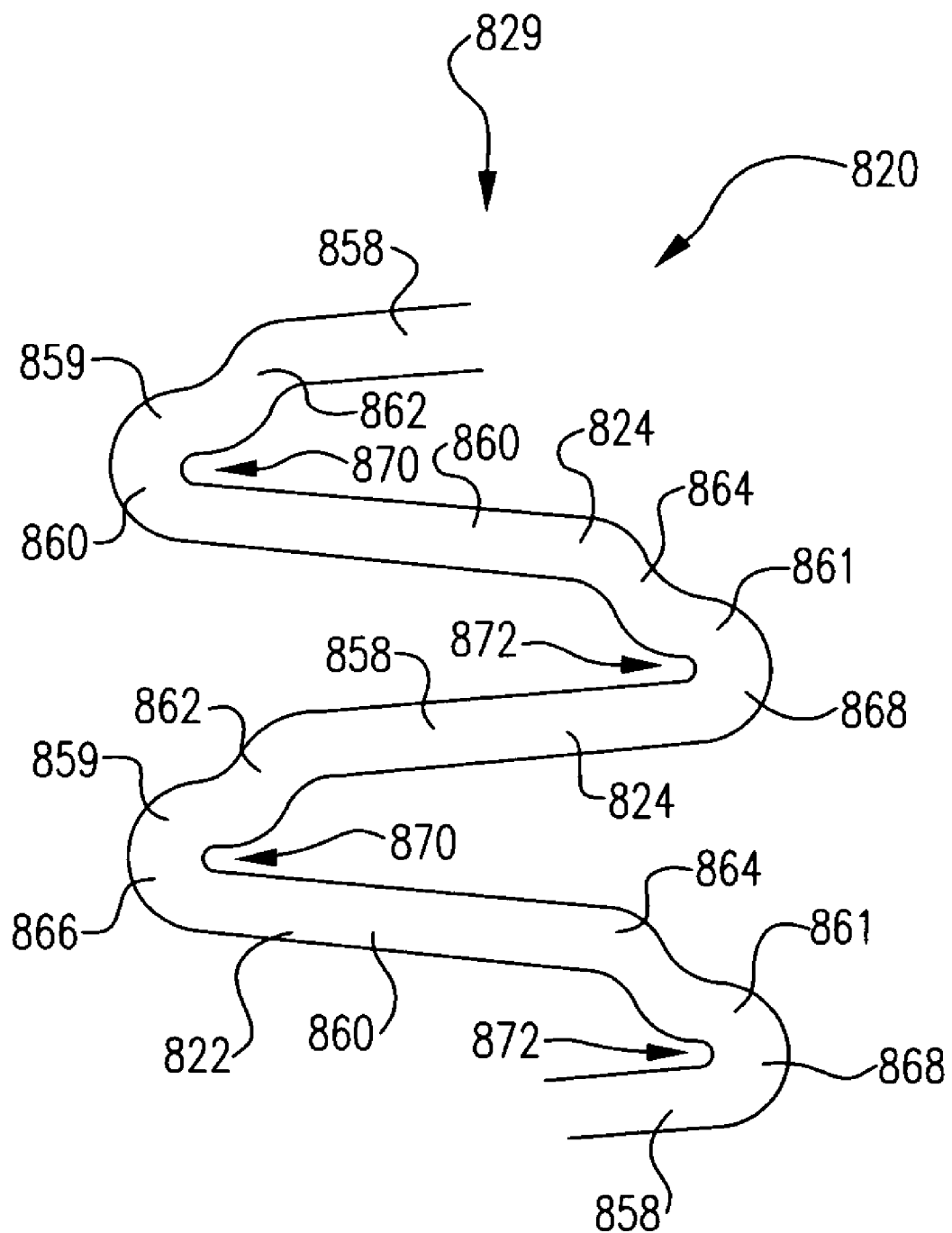

As illustrated in FIG. 28, expansion strut pairs 816 and 824 form loops that couple adjacent individual expansion struts 814 and 822. In one embodiment, the loops of expansion strut pairs 816 and 824 are aligned in a peak to valley geometry. In another embodiment, the loops of expansion strut pairs 816 and 824 are aligned in a peak to peak geometry.

Expansion strut pairs 816 and 824 are jointed by a joining strut segment on distal and proximal ends and form the loops to form a "zigzig" pattern that continues for a selected number of cycles without a break around a circumference of stent 810. The number of cycles can be any number but in one embodiment the number is six or less.

Expansion struts 814 and 822 have first and second segments. At least a portion of the first segment of expansion struts 814 is positioned in close proximity in front of the loop of an expansion strut pair 816. At least a portion of the second section of expansion struts 822 is positioned in close proximity in front of the loop of an expansion strut pair 824. In one embodiment, close proximity is a distance of at least 0.001 inch. In another embodiment, close proximity is a distance less than 0.04 inch. At least one expansion strut 814 and 822 of expansion strut pairs 816 and 824 can have a stair-step segment at its proximal end and, the other expansion strut of the expansion strut pairs 816 and 824 has a stair-step segment at its distal end. In various embodiments, expansion struts 814 and 822 can have a, (i) short stepped-down segment at the proximal end, (ii) short stepped-down segment at the distal end, (iii) short stepped-up segment at the proximal end and short stepped-up segment at a the distal end. In all of these embodiments, expansion struts 814 and 822 have a short sloped transitional segment of that can have the same length between the long and short parts in expansion struts 814 and 822.

Figure 29:
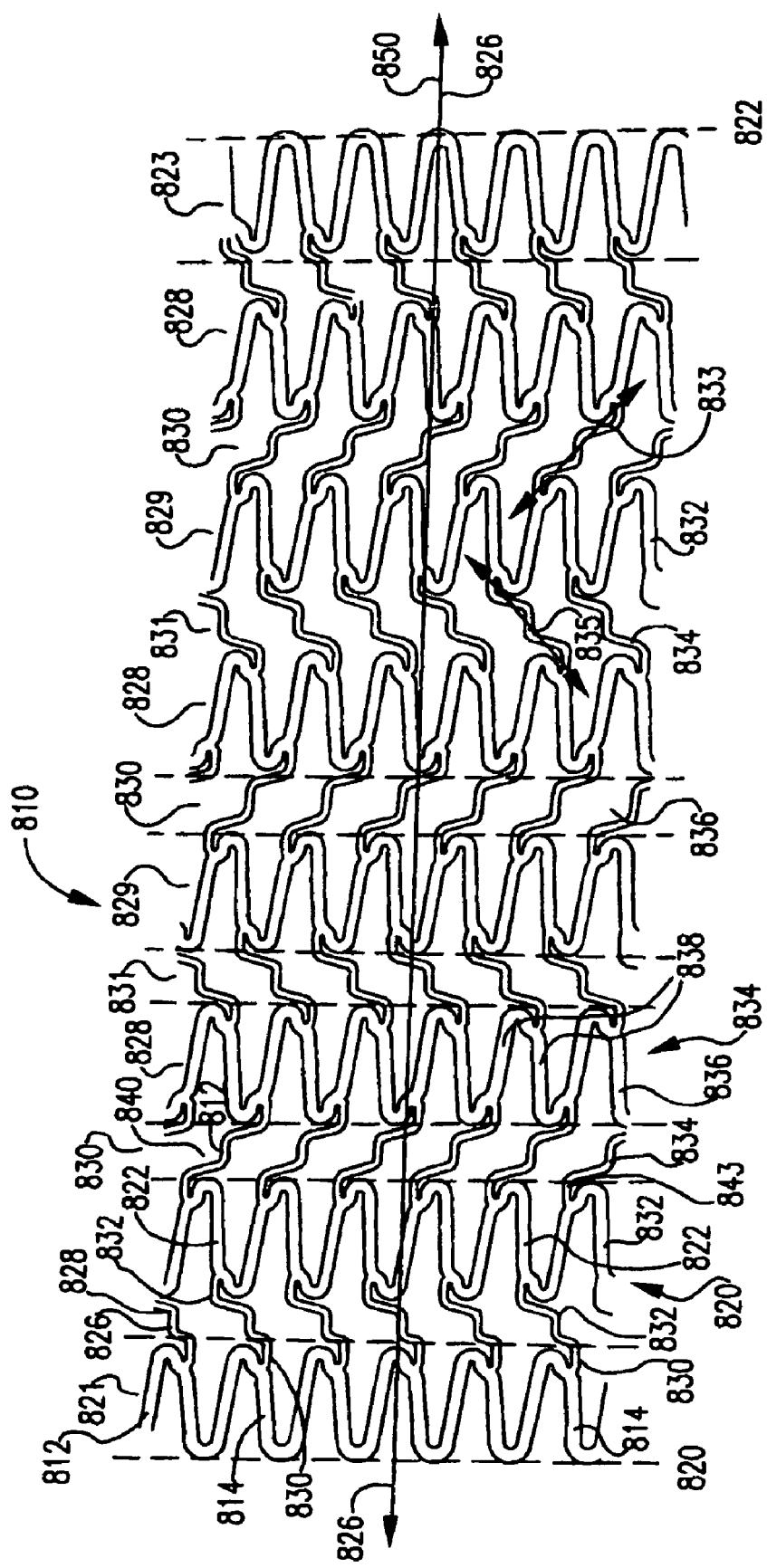
FIG. 29 is a close up view of the FIG. 26 stent.

As illustrated in FIG. 29, stent 810 includes a first connecting strut column 826 with a plurality of individual connecting struts 828. Each connecting strut 828 is an extension arm 830 of an expansion strut 814 from first expansion column 812, and an extension arm 832 of an expansion strut 822 of second expansion column 820.

In the FIG. 29 embodiment, expansion columns 812, 820, 834, and the others in stent 810, have six zigzag cycles. Each six cycle expansion column includes twelve horizontally arranged expansion struts Connecting columns 826, 840 and the others do not have a zig-zag cycle, but have double stair-step connecting struts that are arranged in a paralleling alignment. For every one pair of expansion struts, there is only one associated connecting strut and the ratio of expansion struts to connecting struts is two-one.

Stent 810 also includes additional expansion and connecting strut columns. Stent 810 includes a third expansion column 834 with expansion struts 836 that form expansion strut pairs 838. A second connecting strut column 840 is made of a plurality of individual connecting struts 842. Each connecting strut 842 is an extension arm 843 of an expansion strut 822 from second expansion column 820 and an extension arm 44 of an expansion strut 836 of third expansion column 834.

In various embodiments, one or both extension arms 830 and 832 extend from contra-lateral sides or ipsi-lateral sides of two opposing expansion strut pairs 816 and 824 (FIG. 30); and one or both extension arms 832 and 846 extend from contra-lateral sides or ipsi-lateral sides of two opposing expansion strut pairs 824 and 838 respectively. Extension from contra-lateral sides provides a diagonal link pathway and multiple angled pivot points of a connecting strut 828 and 842 provides enhanced flexibility, conformability and excellent crimping characteristics to stent 810.

Connecting struts 828 in first connecting strut column 826 have a longitudinal axis 846 (FIG. 30) and connecting struts 842 in second connecting strut column 840 have a longitudinal axis 48 (FIG. 31) that is non-parallel to longitudinal axis 846. In various embodiments, longitudinal axis 846 and 848 can be, (i) non-perpendicular to a longitudinal axis 850 of stent 810, (ii) substantially perpendicular to longitudinal axis 850, (iii) substantially diagonal in angle with respect to longitudinal axis 850 and (iv) substantially parallel to longitudinal axis 850.

Longitudinal axis 846 extends in one direction 852 while longitudinal axis 848 extends in an opposite direction 854. Longitudinal axis 846 and 848 each have a diagonal angle 856 with respect to a longitudinal axis of stent 810. Diagonal angle 856 of longitudinal axis 846 extends in direction 852 in any number of different patterns, while diagonal angle 856 of longitudinal axis 848 extends in direction 854 in any number of different patterns. Substantially all of the connecting struts 828 in first connecting strut column 826 have a parallel longitudinal axi 846. The same is true with every connecting strut 842 in second connecting strut column 840, as well as other connecting struts in other connecting strut columns. Preferablly, every connecting strut 842 in first connecting strut column 826 has the same diagonal angle 856 with respect to longitudinal axis 850. The same is true of all other connecting struts in the other connecting strut columns of stent 810. Each longitudinal axis 846 and 848 has a slant angle vertical configuration, e.g., with diagonal angle 856, relative to longiduinal axis 850 of stent 810. This slant angle vertical configuration enhances the flexibility of stent 810 and is crimping characteristics on a balloon.

In various embodiments of the present invention, connecting struts 828, 842, and any other connecting struts in additional connecting strut columns form a, (i) single stair-step pattern, (ii) double stair-step pattern (FIGS. 30 and 31), (iii) multiple stair-step pattern, (iv) a stair-step pattern that includes at least one substantially horizontal segment 858 and at least one substantially slant-angled segment 860 and (v) at least one substantially horizontal segment 858, at least one substantially slant-angled segment 860 and a curved section 862 that joins substantially horizontal segment 858 with substantially slant angled segment 860 (vi) first segment 858 and a second segment 864, with at least a portion of first segment 858 is positioned in close proximity to a loop of an expansion strut pair 816 in first expansion column 812. Curved section 862 can have one radius of curvature, multiple radii of curvature, variabel degrees radius or radii or curvature, a wide or a narrow radius of curvature.

Figure 30:
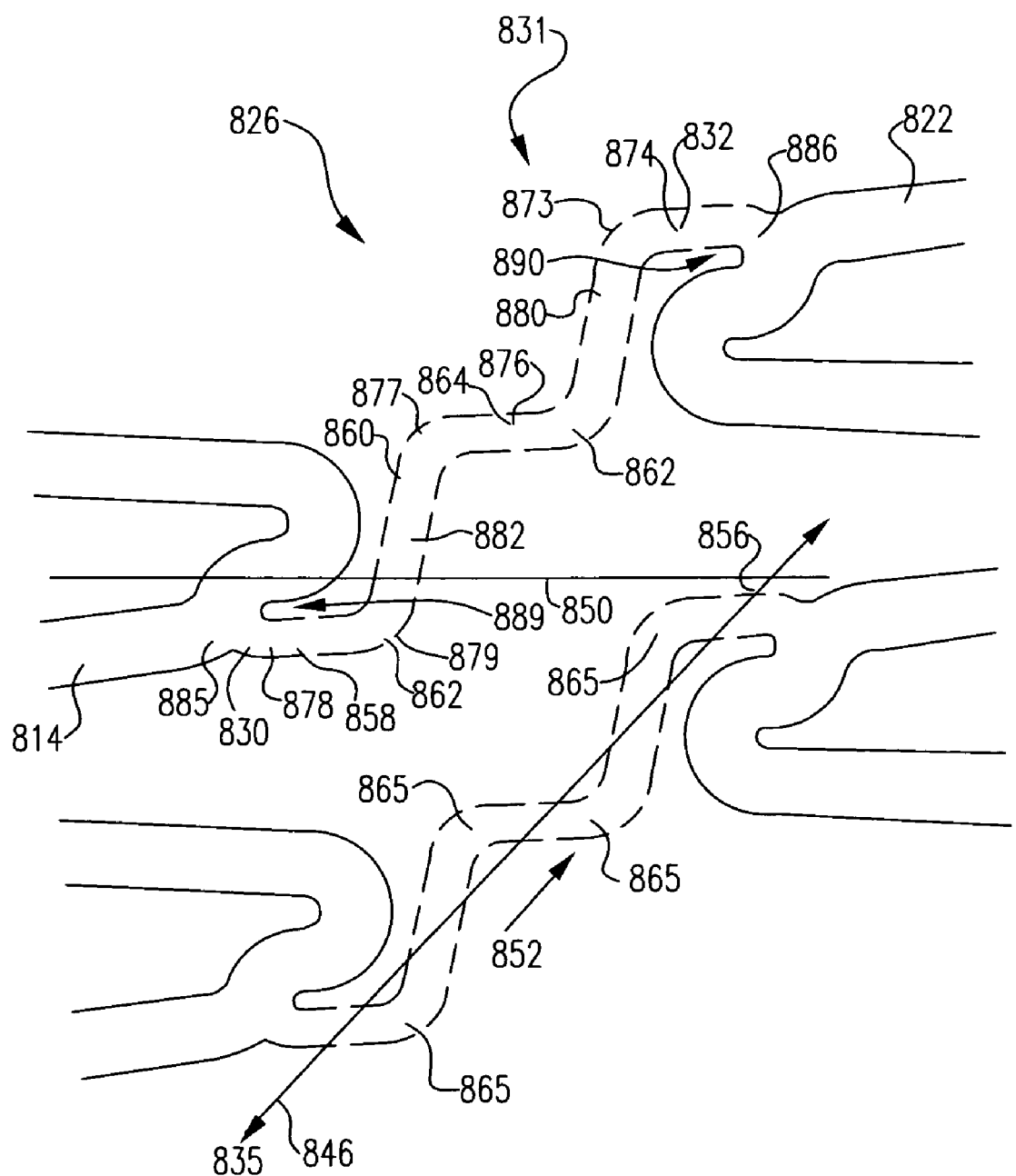
FIG. 30 illustrates one embodiment of the connecting struts of the first connecting strut column.
Figure 31:
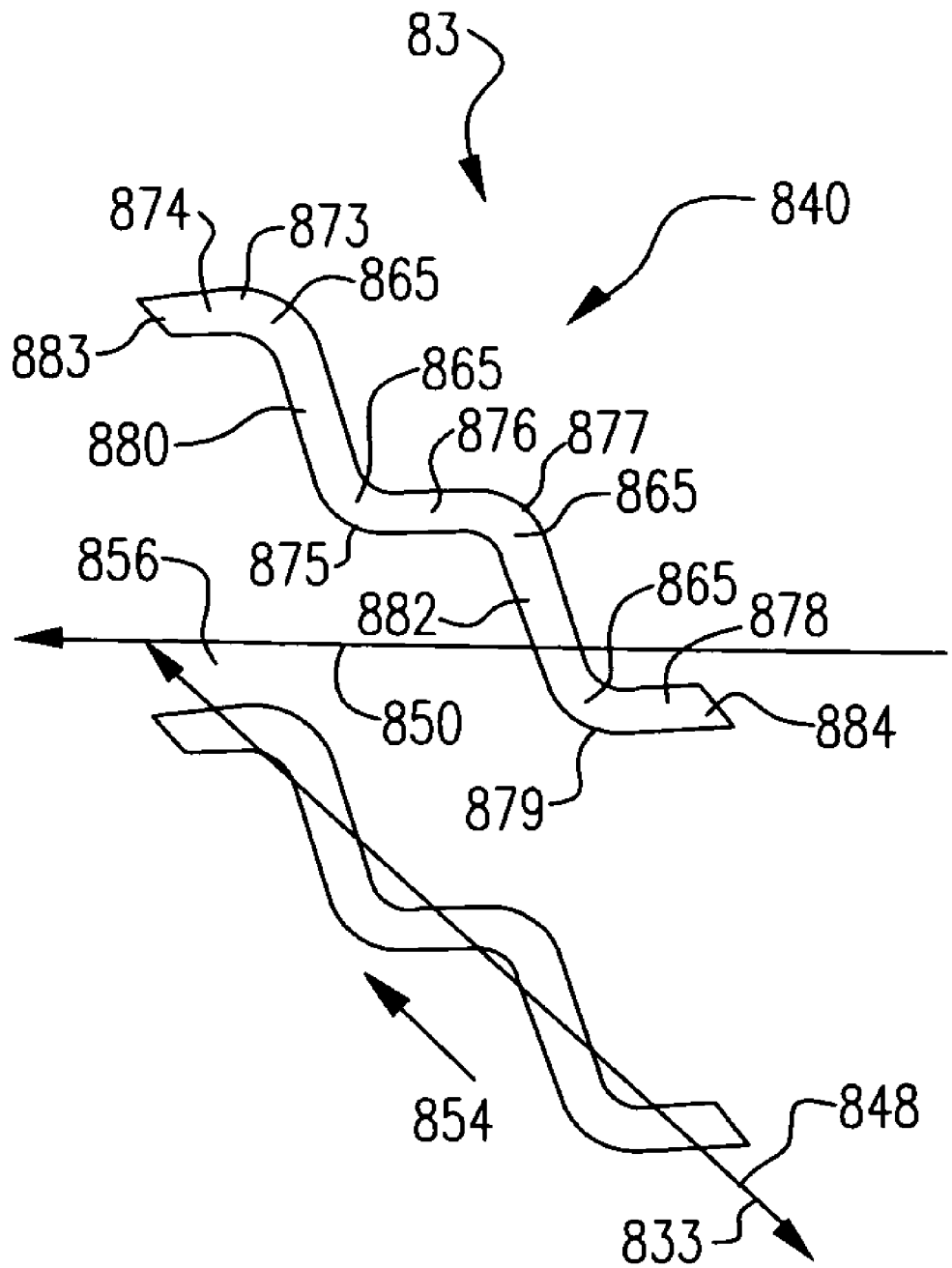
FIG. 31 illustrates one embodiment of the connecting struts that form the second connecting strut column, connector struts joining the expansion struts of FIG. 29.

In the FIGS. 30 and 31 embodiments, expansion struts 814 and 822 have double stair-step patterns with multiple angled pivot points 865. Pivot points 865 also enhance the flexibility of stent 810. Additionally, linking first and second expansion columns 812 and 820 in a diagonally manner relative to longitudianl axis 850 provides further flexibility to stent 810.

Figure 32:
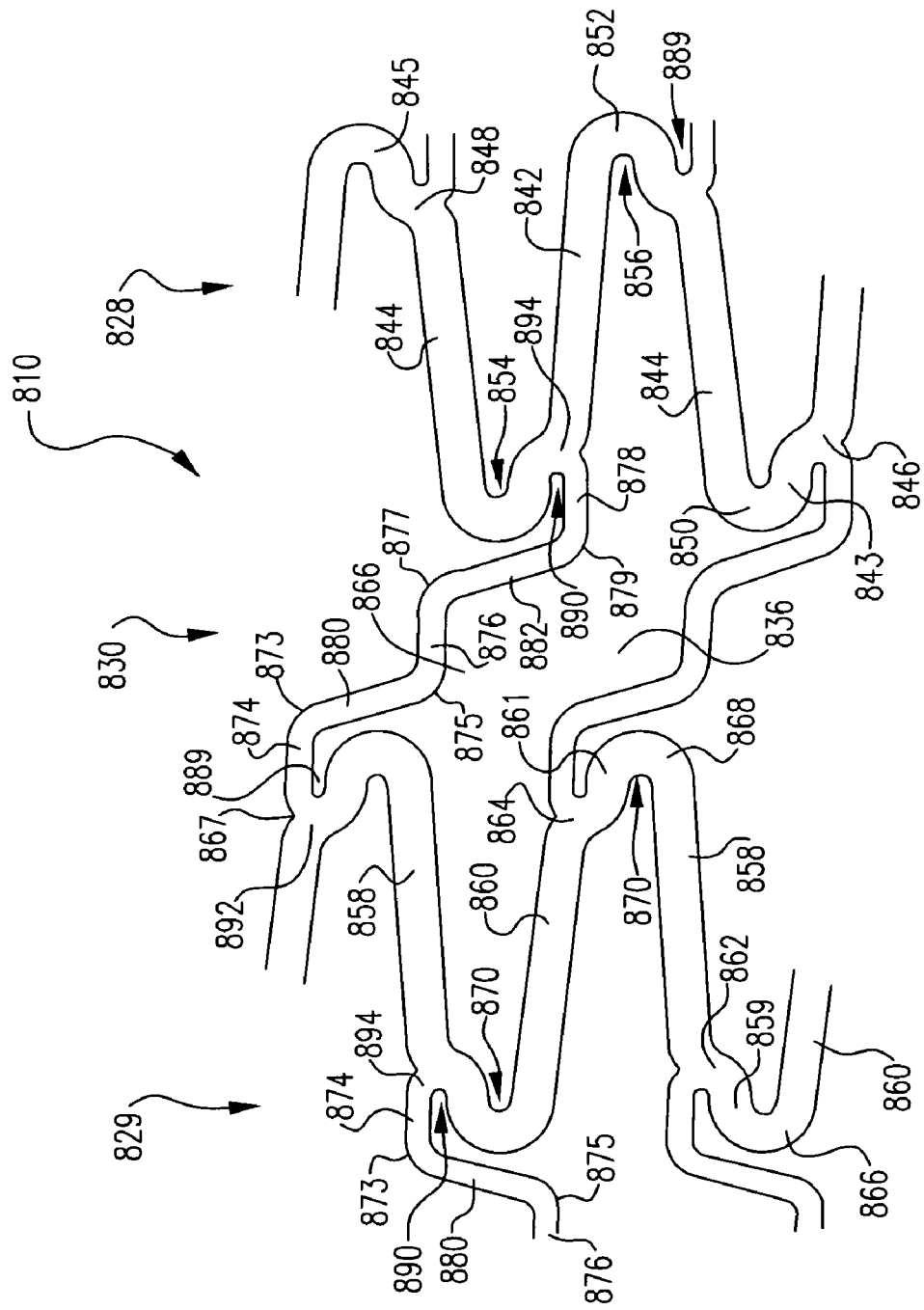
FIG. 32 is a close up view of closed cells created by adjacent expansion columns and their associated connecting strut columns.

Adjacent expansion columns and their associated connecting strut columns define a plurality of cells 866 that are illustrated in FIG. 32. Cells 866 have asymmetrical or symmetrical geometries. Cells 866 can have evenly spaced geometric shapes throughout stent 810. In one embodiment, cells 866 have substantially six sides when stent 810 is in a nominally expanded state. In another embodiment, cells 866 have substantially hexagonal geometric configurations when stent 810 is in a nominally expanded state. Optionally included are strain relief notches 867 that relieve the strain caused by metal deformation when stent 810 is expanded in the deployment phase.

Figure 33:
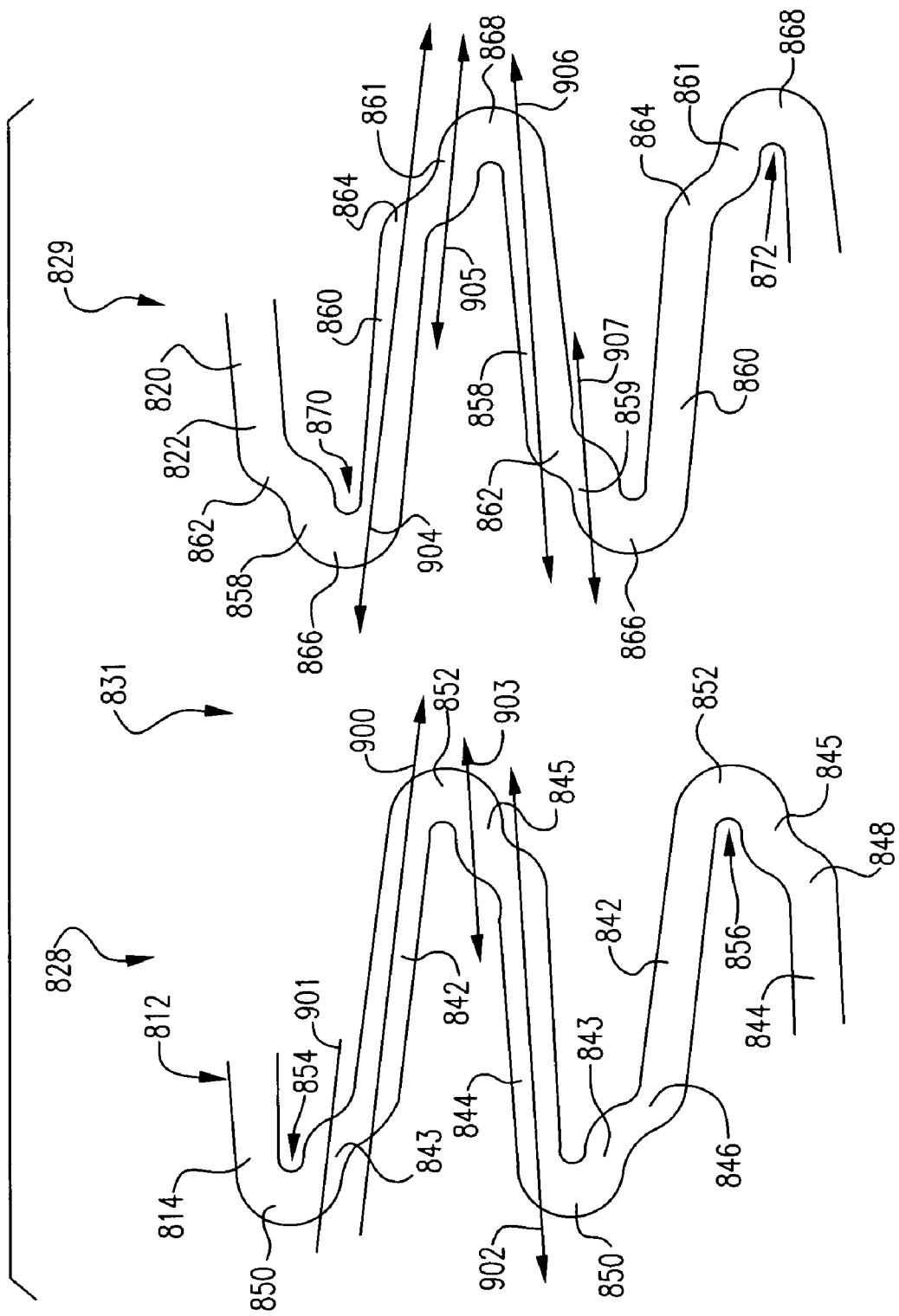
FIG. 33 illustrates the alignment of two adjacent expansion columns.

FIG. 33 illustrates one embodiment of the spacing and alignment characteristics of expansion columns 812 and 820 without illustrating first connecting strut column 826. In this embodiment, the width of first connecting strut column 826 is narrower than the width of expansion columns 812 and 820. However, the width of first connecting strut column 826 can be narrower, the same as or wider than the width of expansion columns 812 and 820. Additionally, the width of any connecting strut column in stent 810 can be variable and different from one or more of the other connecting strut columns of stent 810. Further, the width of any expansion column in stent 810 can be different and variable from one or more other expansion columns in stent 810.

First, second and third expansion columns 812, 820 and 834 can each form a corrugated expansion ring.

In another embodiment, expansion strut pair 816 loops and expansion strut pair 824 loops form first and second bifurcated expansion strut arms 868 at expansion strut bifurcation points.

It should also be further noted that the various embodiments of the stent shown in FIGS. 1-33 may be a standard "single vessel", the stent may also be configured to include a trunk and one or more branches or a single branch with a secondary passage opening in the manner of a bifurcated stent.

In at least one embodiment, any of the various stent configurations shown in FIGS. 1-33, may be configured to deliver one or more therapeutic agents to a delivery site within a vessel. In some embodiments at least a portion of the stent is coated with one or more therapeutic agents. In at least one embodiment the coating includes at least one therapeutic agent and at least one polymer.

In some embodiments one or more stent expansion struts, connecting struts or other portion(s) of a stent, maybe configured to include one or more holes, notches, or other surface features to which one or more therapeutic agents may be placed for delivery to the aneurysm site.

A therapeutic agent may be a drug, a non-genetic agent, a genetic agent, etc. Some examples of suitable non-genetic therapeutic agents include but a re not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are Lin$^-$, Sca-1$^+$, c-Kit$^+$, CD43$^+$, CD45$^+$, CD34$^-$ Lin$^-$—(lineage negative cells) This group of cells is isolated from the bone marrow and all cells which have differentiated to a specific lineage (e.g. red blood cells) have been removed. Therefore leaving all of the stem and progenitor cells. This is beneficial because all primitive cells remain, but may reduce efficiency by including irrelevant, primitive cell types.

Lin$^-$CD34$^-$—Although CD34$^+$ cells have received much attention, many articles have been published lately which suggest the most primitive bone marrow derived stem cells are CD34$^-$ Lin$^-$CD34$^+$—Presence of the cell surface protein CD34 has been used to identify hematopoietic stem cells. However, the marker is also present on progenitor cells and white blood cells of various levels of maturity.

Lin$^-$cKit$^+$—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population. D. Prockop from Tulane U. is publishing in this area.

Cord Blood Cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) Isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the 6$^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult Cardiomyocytes

Fibroblasts—Easily obtained from adult tissues, fibroblasts may provide growth factors or participate in the would healing response. Fibroblast play a critical role in wound healing; the synthesis and deposition of extracellular matrix. Fibroblasts commonly become contractile in wound healing environments.

Smooth muscle cells—Isolated from arteries, these cells may participate or encourage angiogenesis and/or beneficial cardiac remodeling following MI.

MSCs+5-aza—Culture of mesenchymal stem cells with 5-aza forces differentiation into cardiomyocytes. These cells beat spontaneously after treatment.

Adult cardiac fibroblasts+5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In at least one embodiment an example of a suitable polymer agent or coating comprises block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Preferred polyolefinic blocks include polymeric blocks of isobutylene,

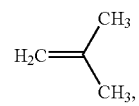

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

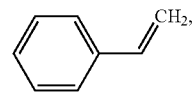

styrene derivatives (e.g., cc-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as star-shaped block copolymers. Other examples of block polymers include branched block copolymers such as dendritic block copolymers, wherein at least one of the A and B blocks is branched, for instance, where the A blocks are branched and are capped by the B blocks.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A stent in a non-expanded state, comprising:
a first expansion column including individual first expansion struts forming a plurality of first expansion strut pairs, each first expansion strut pair including a first expansion strut having a stair-step region at distal end thereof and a stair-step region at a proximal end thereof, two adjacent first expansion strut pairs sharing a common strut;
a second expansion column including individual second expansion struts forming a plurality of second expansion strut pairs, each second expansion strut pair including a second expansion strut having a stair-step region at distal end thereof and a stair-step region at a proximal end thereof, two adjacent second expansion strut pairs sharing a common strut;
a first connecting strut column including a plurality of non-intersecting individual first connecting struts that couple only the first and second expansion columns, wherein each of an individual first connecting strut includes a proximal section and a distal section, the proximal section extending from the stair-step region at the distal end of one of the first expansion struts, the distal section extending from the stair-step region at the proximal end of one of the second expansion struts,
each of the proximal sections having a longitudinal axis and each of the distal sections having a longitudinal axis, at least one of the longitudinal axis of each of the proximal sections and the longitudinal axis of each of the distal sections being parallel with at least one of a longitudinal axis of each first expansion strut and a longitudinal axis of each second expansion strut; wherein
each first and second expansion strut includes a straight segment between the stair-step region at distal end thereof and the stair-step region at proximal end thereof.

2. The stent of claim 1, wherein each first connecting strut of the first connecting strut column has a stair-step configuration.

3. The stent of claim 1, wherein each first expansion strut pair of the first expansion column includes a straight strut.

4. The stent of claim 3, wherein each second expansion strut pair of the second expansion column includes a straight strut.

5. The stent of claim 1, wherein the proximal section of each first connecting strut has an edge that is a linear extension of an edge of an expansion strut in the first expansion column, and the distal section of each first connecting strut has an edge that is a linear extension of an edge of an expansion strut in the second expansion column.

6. The stent of claim 5, wherein a strain relief notch is formed where the edge of the proximal section of each first connecting strut in the first connecting strut column is conjoined with the edge of the expansion strut of the first expansion column, and a strain relief notch is formed where the edge of the distal section of each first connecting strut in the first connecting strut column is conjoined with edge of the expansion strut of the second expansion column.

7. The stent of claim 1, wherein the distal section of each first connecting strut of the first connecting strut column has a greater length than its proximal section.

8. The stent of claim 1, wherein each first connecting strut of the first connecting column is ipsilaterally conjoined to the first and second expansion columns.

9. The stent of claim 1, wherein the longitudinal axis of the proximal section of each first connecting strut of the first connecting strut column is non-parallel to the longitudinal axis of its distal section.

10. The stent of claim 1, wherein each first connecting strut of the first connecting strut column includes an intermediate section coupled to the proximal and distal sections of the first connecting strut.

11. The stent of claim 10, wherein the intermediate section of each first connecting strut of the first connecting strut column has a greater length than a length of its proximal section.

12. The stent of claim 10, wherein at least a portion of the intermediate section of each first connecting strut of the first connecting strut column has a curvilinear geometric configuration.

13. The stent of claim 12, wherein at least a portion of the proximal and distal sections of each first connecting strut of the first connecting strut column have a curvilinear geometric configuration.

14. The stent of claim 10, wherein the intermediate section of each first connecting strut of the first connecting strut column has a longitudinal axis that is nonparallel to a longitudinal axis of the stent.

15. The stent of claim 10, wherein the intermediate section of each first connecting strut of the first connecting strut column has a longitudinal axis that is positioned diagonally relative to a longitudinal axis of the stent.

16. The stent of claim 10, wherein the intermediate section of each first connecting strut of the first connecting strut column has a longitudinal axis that extends in a vertically diagonal direction relative to a longitudinal axis of the stent.

17. The stent of claim 10, wherein at least a portion of the intermediate section of each first connecting strut of the first connecting strut column is in close proximity to an expansion strut pair of the first expansion column.

18. The stent of claim 1, wherein a width of the proximal section of each first connecting strut in the first connecting strut column is less than a width of the expansion strut of the first expansion column, and a width of the distal section of each first connecting strut of the first connecting strut column is less than a width of the expansion strut of the second expansion column.

19. The stent of claim 1, further comprising:
a plurality of expansion columns coupled by a plurality of connecting strut columns.

20. The stent of claim 1, further comprising:
a third expansion column including individual expansion struts forming a plurality of expansion strut pairs, wherein two adjacent expansion strut pairs share a common strut;
a second connecting strut column including a plurality of non-intersecting individual second connecting struts that couple only the second and third expansion columns, wherein each of an individual second connecting strut of the second connecting strut column includes a proximal section with a longitudinal axis that is parallel with a longitudinal axis of an expansion strut in the second expansion column, and a distal section with a longitudinal axis that is parallel with a longitudinal axis of an expansion strut of the third expansion column.

\* \* \* \* \*